US010973843B2

(12) United States Patent
Younis

(10) Patent No.: US 10,973,843 B2
(45) Date of Patent: Apr. 13, 2021

(54) METHOD FOR MONITORING CANCER AND FOR REGULATION OF SEMAPHORIN 4D TO IMPROVE CANCER IMMUNOTHERAPY REGIMENS

(71) Applicant: University of Maryland, Baltimore, Baltimore, MD (US)

(72) Inventor: Rania H. Younis, Ellicott City, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 130 days.

(21) Appl. No.: 16/071,133

(22) PCT Filed: Jan. 27, 2017

(86) PCT No.: PCT/US2017/015395
§ 371 (c)(1),
(2) Date: Jul. 19, 2018

(87) PCT Pub. No.: WO2017/132541
PCT Pub. Date: Aug. 3, 2017

(65) Prior Publication Data

US 2019/0030060 A1 Jan. 31, 2019

Related U.S. Application Data

(60) Provisional application No. 62/287,622, filed on Jan. 27, 2016.

(51) Int. Cl.

*A61K 31/713* (2006.01)
*A61P 35/00* (2006.01)
*A61K 31/7105* (2006.01)
*A61K 31/711* (2006.01)
*C12N 15/864* (2006.01)
*G01N 33/574* (2006.01)

(52) U.S. Cl.

CPC .......... *A61K 31/713* (2013.01); *A61K 31/711* (2013.01); *A61K 31/7105* (2013.01); *A61P 35/00* (2018.01); *C12N 15/8645* (2013.01); *G01N 33/57484* (2013.01); *C12N 2310/531* (2013.01); *G01N 2333/715* (2013.01); *G01N 2800/56* (2013.01)

(58) Field of Classification Search

None
See application file for complete search history.

(56) References Cited

U.S. PATENT DOCUMENTS

2008/0293053 A1* 11/2008 Keller ................ C12N 15/1135 435/6.17
2009/0104193 A1 4/2009 Lai
2015/0044219 A1 2/2015 Evans et al.
2015/0204887 A1 7/2015 Epstein

OTHER PUBLICATIONS

Basile et al., Semaphorin 4D provides a link between axon guidance preocess and tumor-induced angiogenesis, PNAS, 103:9017-9022 (2006).
International Search Report from International Appl. No. PCT/US17/15395, dated Jun. 5, 2017.
Capparuccia et al., Semaphorin signaling in cancer cells and in cells of the tumor microenvironment—two sides of a coin, J Cell Sci, 122:1723-1736 (2009).
Ch'Ng, et al., Prognostic Significance of CD100 Expression in Soft Tissue Sarcoma, Cancer, 110:164-172 (2007).
Ch'Ng et al., Roles of Sema4D and Plexin-B1 in tumor progression, Mol Cancer, 9:251 (2010).
Chouaib et al., Hypoxia promotes tumor growth in linking angiogenesis to immune escape, Front Immunol, 3:1-10 (2012).
Delaire et al., CD100 is a leukocyte semaphorin, Cell Mol Life Sci, 54:1265-1276 (1998).
Hanahan et al., Hallmarks of Cancer: The Next Generation, Cell, 144:646-674 (2011).
Ishida et al., Involvement of CD100, a lymphocyte semaphorin, in the activation of the human immune system via CD72: implications for the regulation of immune and inflammatory responses, International Immunology, 15:1027-1034 (2003).
Kumanogoh et al., Immune semaphorins: a new area of semaphorin research, Journal of Cell Science, 116:3463-3470 (2003).
Lechner et al., Characterization of Cytokine-Induced Myeloid-Derived Suppressor Cells from Normal Human Peripheral Blood Mononuclear Cells, J Immunol, 185:2273-2284 (2010).
Lechner et al., Functional characterization of human Cd33+ and Cd11b+ myeloid-derived suppressor cell subsets induced from peripheral blood mononuclear cells co-cultured with a diverse set of human tumor cell lines, J Transl Med, 9:1-20 (2011).
Madore et al., PD-L1 Negative Status is Associated with Lower Mutation Burden, Differential Expression of Immune-Related Genes, and Worse Survival in Stage III Melanoma, Clin Cancer Res, 22:3915-3923 (2016).
Pietras et al., Hallmarks of cancer: Interactions with the tumor stroma, Exp Cell Res, 316:1324-1331 (2010).
Roth et al., The many faces of semaphorins: from development to pathology, Cell. Mol. Life Sci., 66:649-666 (2009).
Shi et al., The Class IV Semaphorin CD100 Plays Nonredundant Roles in the Immune System: Defective B and T Cell Activation in CD100-Deficient Mice, Immunity, 13:633-642 (2000).
Sierra et al., Tumor angiogenesis and progression are enhanced by Sema4D produced by tumor-associated macrophages, J Exp Med, 205:1673-1685 (2008).
Tamagnone et al., To move or not to move?, EMBO Rep 5:356-361 (2004).

(Continued)

*Primary Examiner* — Tracy Vivlemore
(74) *Attorney, Agent, or Firm* — Nevrivy Patent Law Group P.L.L.C.

(57) ABSTRACT

The present invention provides a method of inhibiting tumor-mediated immunosuppression in a subject, comprising administering to the subject a therapeutically effective amount of an agent that inhibits the activity of Semaphorin 4D.

13 Claims, 37 Drawing Sheets

Specification includes a Sequence Listing.

(56) References Cited

OTHER PUBLICATIONS

Wang et al., Semaphorin 4D and hypoxia-inducible factor-1α overexpression is related to prognosis in colorectal carcinoma, World J Gastroenterol, 21:2191-2198 (2015).
Younis et al., Human Head and Neck Squamous Cell Carcinoma—Associated Semaphorin 4D Induces Expansion of Myeloid-Derived Suppressor CellsJ Immunol, 196:1419-1429 (2016).
Thou et al., The hypoxia-induciblefactor-responsiveproteins semaphorin 4Dandvascularendothelialgrowthfactor promote tumorgrowthandangiogenesisinoralsquamous cell carcinoma, Exp Cell Res, 318:1685-1698 (2012).

* cited by examiner

A.
M:T 1:4
M:T 1:1
M:T 1:2
M:T 2:1
Ctl-shRNA
Sema4D-shRNA
Ctl-shRNA
Sema4D-shRNA
Count A.
HN6 CM
89.8
P3
HN6 CM Sema4D IP
68.4
P3
HN6 CM GM-CSF IP
60.3
P3
count
HLA-DR
B.
HN6 CM
P2
HN6 CM Sema4D IP
39.8
P2
HN6 CM GM-CSF IP
46.7
P2
count HN- Head and Neck Cancer
HD- pooled serum AB type from healthy male donors Sema4D can be detected in lymphoma patient sera HD- Healthy Donor
MCL- Mantle Cell Lymphoma
CLL- Chronic Lymphocytic Leukemia
DLBCL- Diffuse Large B cell lymphoma pooled- Human AB serum pooled from healthy male donors

METHOD FOR MONITORING CANCER AND FOR REGULATION OF SEMAPHORIN 4D TO IMPROVE CANCER IMMUNOTHERAPY REGIMENS

CROSS-REFERENCE TO RELATED APPLICATIONS

This application claims the benefit of U.S. Provisional Appl. No. 62/287,622 filed on Jan. 27, 2016, the contents of which are hereby incorporated by reference in their entirety.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 25,847 Byte ASCII (Text) file named "Seq_listing_ST25.txt," created on Jan. 27, 2017.

FIELD OF THE INVENTION

The field of the invention relates generally to the field of medicine and cancer biology.

BACKGROUND OF THE INVENTION

Head and Neck squamous cell carcinoma (HNSCC) is a malignancy of high morbidity and mortality, with 45,780 new cases and 8,650 estimated deaths of oral and pharyngeal cancer estimated to occur in the United States in the year 2015 (Siegel et al., 2015. *CA Cancer J Clin* 65: 5-29). There is accumulating evidence indicating the immune-modulatory effects of HNSCC by which it can escape and/or suppress the immune system (Hadden et al., 1994. *Arch Otolaryngol Head Neck Surg* 120: 395-403; Katz, A. E. 1993. *Med Clin North Am* 77: 625-631; Vlock, D. R. 1991. *Hematol Oncol Clin North Am* 5: 797-820; Russell et al., 2011. *Oral Oncol* 47: 810-817; Gildener-Leapman et al., 2013. *Oral Oncol* 49: 1089-1096).

Myeloid Derived Suppressor cells (MDSC) have been described in peripheral blood, draining lymphoid tissue and tumor tissue of several malignancies (Russell et al., 2011. *Oral Oncol* 47: 810-817; Lechner et al., 2011. *J Transl Med* 9: 90; Vasquez-Dunddel et al., 2013. *J Clin Invest* 123: 1580-1589; Gabitass et al., 2011. *Cancer Immunol Immunother* 60: 1419-1430; Filipazzi et al., 2012. *Cancer Immunol Immunother* 61: 255-263). Circulating MDSC correlated with advanced stages of HNSCC (stages III and IV) as well as in other carcinomas (Vasquez-Dunddel et al., 2013. *J Clin Invest* 123: 1580-1589; Filipazzi et al., 2012. *Cancer Immunol Immunother* 61: 255-263; Vuk-Pavlovic et al., 2010. *Prostate* 70: 443-455). MDSC represent a key player in immune regulation in the tumor microenvironment. It is generally agreed that they comprise a heterogeneous population of myeloid progenitor cells and immature myeloid cells that have a suppressive function on T cells (Gabrilovich et al., 2009. *Nat Rev Immunol* 9: 162-174; Talmadge et al., 2013. *Nat Rev Cancer* 13: 739-752). MDSC described in human malignancies have the phenotype of $CD33^+$, $CD11b^+$, and non-lineage determined ($Lin^-$) with poor antigen presentation abilities ($HLA\text{-}DR^{-/low}$). They can have a pro-granulocytic phenotype expressing CD66b or CD15 (PMNL-MDSC) or monocytic features (M-MDSC) expressing CD14 (Filipazzi et al., 2012. *Cancer Immunol Immunother* 61: 255-263; Lechner et al., 2010. *J Immunol* 185: 2273-2284; Gabrilovich et al., 2012. *Nat Rev Immunol* 12: 253-268). MDSC induce their immune suppressive effect mainly through production of arginase-1 and inducible nitric oxide (iNOS) which consume extracellular arginine and accordingly suppress T cell activation in an antigen non-specific manner in the tumor microenvironment. While they mediated antigen specific suppression by NADPH oxidase (NOX2) production of reactive oxygen and nitrogen species, particularly in peripheral lymphoid tissue, as well as by other mechanisms (Gabrilovich et al., 2009. *Nat Rev Immunol* 9: 162-174; Gabrilovich et al., 2012. *Nat Rev Immunol* 12: 253-268; Condamine et al., 2011. *Trends Immunol* 32: 19-25; Corzo et al., 2010. *J Exp Med* 207: 2439-2453). In addition to direct T cell suppression, recent evidence suggests a role for MDSC in the expansion of $CD4^+CD25^+$ $FoxP3^+$, regulatory T cells (Tregs) in the tumor microenvironment through both TGF-β dependent and independent pathways (Vuk-Pavlovic et al., 2010. *Prostate* 70: 443-455; Capparuccia et al., 2009. *J Cell Sci* 122: 1723-1736). While several mechanisms have been described by which tumor cells induce MDSC, the specific pathways by which HNSCC recruit, expand, and activate MDSC remain to be investigated (Gabrilovich et al., 2012. *Nat Rev Immunol* 12: 253-268; Pak et al., 1995. *Clin Cancer Res* 1: 95-103; Young et al., 1997. *Int J Cancer* 74: 69-74).

Tumor cells overexpress several cytokines in order to manipulate their own microenvironment, among which are multiple Semaphorins, that have the potential to act on different stromal cells (Capparuccia et al., 2009. *J Cell Sci* 122: 1723-1736). Semaphorin 4D (Sema4D; CD100) is a transmembrane glycoprotein belonging to the fourth group of the Semaphorin family that can also be found in a soluble form following proteolytic cleavage. It was initially identified as an evolutionarily conserved chemo-repellant protein that regulates axonal guidance in the developing nervous system (Kolodkin et al., 1993. *Cell* 75: 1389-1399). Later on, its interactions in other systems were emphasized, including the cardiovascular system and immune system. In the immune system, Sema4D is described to be expressed abundantly on resting T cells and weakly on resting B cells and APCs (Delaire et al., 1998. *Cell Mol Life Sci* 54: 1265-1276; Roth et al., 2009. *Cell Mol Life Sci* 66: 649-666; Bismuth et al., 2002. *Sci STKE* 2002: re4; Shi et al., 2000. *Immunity* 13: 633-642; Tamagnone et al., 2004. *EMBO Rep* 5: 356-361). Two opposing roles of Sema4D have been described in the immune system. One role is a pro-inflammatory response; where for example in the humoral and cell mediated immune system, Sema4D acts on B cells and dendritic cells, respectively, promoting pro-inflammatory cytokines (Shi et al., 2000. *Immunity* 13: 633-642; Tamagnone et al., 2004. *EMBO Rep* 5: 356-361; Ishida et al., 2003. *Int Immunol* 15: 1027-1034). Sema4D expressed by T cells and NK cells has also been implicated in their activation through a Sema4D associated tyrosine kinase (Elhabazi et al., 1997. *J Blot Chem* 272: 23515-23520), and has been shown to play a role in T cell priming and accordingly in the pathogenesis of autoimmune diseases (Okuno et al., 2010. *J Immunol* 184: 1499-1506). While on the other hand, an anti-inflammatory role of Sema4D in the immune system has also been described. On monocytes and immature dendritic cells, Sema4D can act on Plexin C1 and Plexin B1, respectively, inhibiting their migration, but not that of mature dendritic cells, which can provide more interaction between immature myeloid cells and T cells (Chabbert-de Ponnat et al., 2005. *Int Immunol* 17: 439-447; Delaire et al., 2001. *J Immunol* 166: 4348-4354). Furthermore, in vitro studies have shown that Sema4D can modulate cytokine production by monocytes and dendritic cells, and can induce a significant increase in the anti-inflammatory cytokine IL-10 and a decrease in the pro-inflammatory cytokines IL-6, IL-8 and TNF-α (Tamagnone et al., 2004. *EMBO Rep* 5: 356-361; Chabbert-de Ponnat et al., 2005. *Int Immunol* 17: 439-447; Delaire et al., 2001. *J Immunol* 166: 4348-4354).

The role of Sema4D produced by tumor cells in inducing tumor angiogenesis, invasiveness and progression has been demonstrated in several malignancies, both in human and animal models, and correlates with poor prognosis (Basile et al., 2006. *Proc Natl Acad Sci USA* 103: 9017-9022; Zhou et al., 2012. *Exp Cell Res* 318: 1685-1698; Zhou et al., 2012. *Angiogenesis*; Mu et al., 2014. *Zhonghua Wei Chang Wai Ke Za Zhi* 17: 388-392; Liu et al., 2014. *Microvasc Res* 93: 1-8; Ch'ng, et al., 2010. *Mol Cancer* 9: 251; Chen et al., 2012. *Int J Mot Sci* 13: 13264-13274). Sema4D overexpression has been described in a large number of human HNSCC tumor tissue samples and in a panel of primary and metastatic cell lines (Basile et al., 2006. *Proc Natl Acad Sci USA* 103: 9017-9022). In the tumor microenvironment, tumor associated macrophages (TAMs) were reported to be the main producers of Sema4D in a mouse breast cancer model (Sierra et al., 2008. *J Exp Med* 205: 1673-1685).

There is a need to develop new methods for enhancing the effectiveness of immunotherapeutic approaches and for treating cancer. The present invention satisfies this need and provides additional advantages as well.

This background information is provided for informational purposes only. No admission is necessarily intended, nor should it be construed, that any of the preceding information constitutes prior art against the present invention.

SUMMARY OF THE INVENTION

It is to be understood that both the foregoing general description of the embodiments and the following detailed description are exemplary, and thus do not restrict the scope of the embodiments.

The hypothesis tested in the current study was that the net inflammatory profile orchestrated by Sema4D in the tumor microenvironment is pro-tumorigenic through induction of immune suppressive cells. Herein, it is investigated whether HNSCC derived Sema4D plays a role in inducing MDSC and its effects were examined on T cell phenotype and function. It was found that Sema4D produced by the HNSCC HN6 and HN13 cell lines polarized myeloid cells into MDSC phenotype, which corresponded with a reduction in T cell proliferation and IFN-γ production. Furthermore, shRNA inhibition of Sema4D in HN6 resulted in a decrease in the production of the immunosuppressive factors; arginase-1, TGF-β1, and IL-10 by myeloid cells and the recovery of autologous T cell proliferation, IFN-γ production, specifically leading to an increase in the effector T cell population and decrease in Tregs. These findings describe HNSCC-associated Sema4D production as one of the mechanisms by which the tumors induce MDSC, that subsequently mediate their immunosuppression effects on T cells.

In one aspect, the invention relates to a rapid and sensitive method for monitoring certain cancers such as head and neck squamous cell carcinoma and lymphomas.

In another aspect, the invention relates to methods for improving certain cancer immunotherapy treatment regimens based on the cytokine Semaphorin 4D.

In another aspect, the invention provides a method of inhibiting tumor-mediated immunosuppression in a subject, comprising administering to the subject a therapeutically effective amount of an agent that inhibits the activity of Semaphorin 4D.

In another aspect, the invention provides a method of inhibiting tumor-mediated immunosuppression in a subject undergoing immunotherapy, comprising administering to the subject a therapeutically effective amount of an agent that inhibits the activity of Semaphorin 4D. In some embodiments, the immunotherapeutic agent comprises T cells.

In another aspect, the invention provides a method of screening for an agent that has anti-cancer activity, comprising i) contacting a cell culture medium comprising Semaphorin 4D and/or cells comprising Semaphorin 4D with the agent; and ii) assaying whether Semaphorin 4D activity is reduced, wherein if Semaphorin 4D activity is reduced, the agent has anti-cancer activity. In some embodiments, the assaying of part ii) comprises culturing a cell population comprising myeloid cells in the cell culture medium and detecting the presence or absence of myeloid-derived suppressor cells, wherein if the level of myeloid-derived suppressor cells is reduced relative to a control sample lacking the agent, then the agent has anti-cancer activity.

In another aspect, the invention provides a method of monitoring progression of cancer in a subject, comprising i) obtaining a tissue sample from the subject; and ii) assaying the sample for the presence of Semaphorin 4D, wherein elevated levels of Semaphorin 4D compared to a tissue sample from a healthy donor indicate progression of the cancer in the subject.

In another aspect, the invention provides a composition for inhibiting tumor-mediated immunosuppression in a subject and thereby treating cancer, comprising a nucleic acid that comprises a nucleotide sequence that binds to at least a portion of a nucleotide sequence of Semaphorin 4D and a pharmaceutically acceptable carrier.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION OF THE INVENTION

Figure 1A:
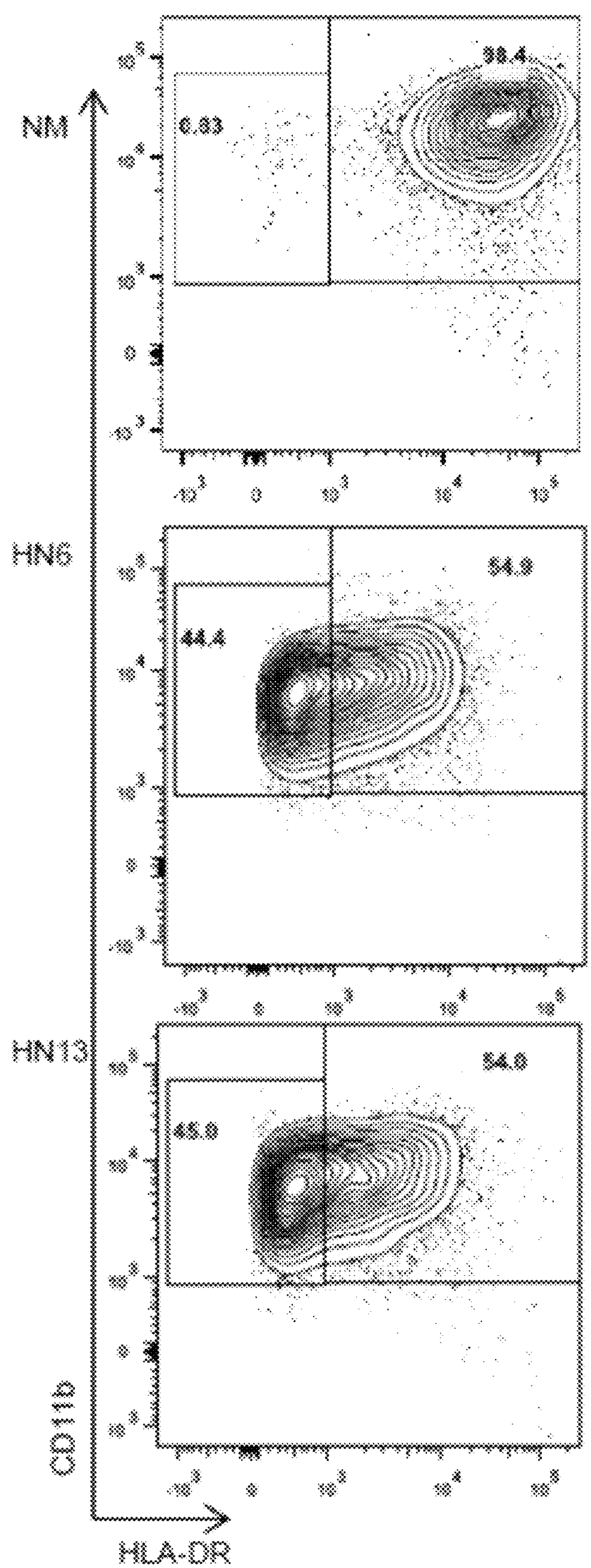
FIG. 1. HNSCC conditioned media polarizes myeloid cells towards a MDSC phenotype. (A) $CD33^+$ cells were cultured in normal media (NM) or HNSCC conditioned media (HN6, HN13) for 72 hrs, and then analyzed by flow cytometry. (B) Dose dependent induction of MDSC following culture in HNSCC condition media. $CD33^+$ cells were cultured in serial dilutions of HN6 CM and (C) HN13 CM. Cells were first gated for $CD33^+$ then for $CD11b^+$, followed by a third gate for $CD11b^+$ $HLA\text{-}DR^{-/low}$. CD33 cells were isolated using magnetic cell sorting (MACS), from PBMC separated by centrifugation gradient of peripheral blood. All samples were run in duplicates. NM; Normal media, CM; Conditioned medium.

One of the mechanisms by which malignancies can induce immune suppression is through the production of cytokines that affect the maturation and differentiation of inflammatory cells in the tumor microenvironment. The inventor has surprisingly discovered that inhibition of Semaphorin 4D inhibits tumor-mediated immunosuppression, and that inhibiting Semaphorin 4D can be employed in methods useful for treating cancer. The inventor has also discovered methods which can be used in monitoring cancer progression involving monitoring detection of Semaphorin 4D.

Semaphorin 4D (Sema4D) is a pro-angiogenic cytokine produced by several malignancies, which has been described in the regulation of the immune system. Described herein are studies which examined the role of human Head and Neck Squamous Cell Carcinoma (HNSCC) secreted Sema4D on myeloid cell differentiation. CD33$^+$ cells cultured in HNSCC cell line derived-conditioned medium differentiated into myeloid derived suppressor cells (MDSC) (CD33$^+$ CD11b$^+$ HLA-DR$^{-/low}$). The addition of anti-Sema4D antibody to HNSCC conditioned medium significantly reduced the expansion of the MDSC population. Similarly, knockdown of Sema4D in a HNSCC cell line resulted in a loss of MDSC function as shown by a decrease in the production of the immune suppressive cytokines, arginase-1, TGF-β, and IL-10 by MDSC, concomitant with recovery of T cell proliferation and IFN-γ production following stimulation of CD3/CD28. Importantly, CD33$^+$ myeloid and T cells cultured in conditioned medium of HNSCC cells in which Sema4D was knocked down, promoted anti-tumor inflammatory profile, through recovery of the effector T cells (CD4$^+$Tbet$^+$ and CD8$^+$Tbet$^+$), as well as a decrease in Tregs (CD4$^+$CD25$^+$FoxP3$^+$) cell. It is also shown herein that Sema4D was comparative to GM-CSF in its induction of MDSC. Collectively, this work describes a novel immunosuppressive role for Sema4D in HNSCC through induction of MDSC, and highlights it as a therapeutic target to enhance the antitumorigenic inflammatory response in HNSCC and other epithelial malignancies.

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. See, e.g., Sambrook et al. *Molecular Cloning: A Laboratory Manual, 2nd edition* (1989); *Current Protocols in Molecular Biology* (F. M. Ausubel et al. eds. (1987)); the series *Methods in Enzymology* (Academic Press, Inc.); *PCR: A Practical Approach* (M. MacPherson et al. IRL Press at Oxford University Press (1991)); *PCR* 2: *A Practical Approach* (M. J. MacPherson, B. D. Hames and G. R. Taylor eds. (1995)); *Antibodies, A Laboratory Manual* (Harlow and Lane eds. (1988)); *Using Antibodies, A Laboratory Manual* (Harlow and Lane eds. (1999)); and *Animal Cell Culture* (R. I. Freshney ed. (1987)).

Definitions of common terms in molecular biology may be found, for example, in Benjamin Lewin, *Genes VII, published by Oxford University Press,* 2000 (ISBN 019879276X); Kendrew et al. (eds.); *The Encyclopedia of*

*Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "a cell" includes a plurality of cells, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" means plus or minus 10% of the numerical value of the number with which it is being used.

In one embodiment, the invention provides a method of inhibiting tumor-mediated immunosuppression in a subject, comprising administering to the subject a therapeutically effective amount of an agent that inhibits the activity of Semaphorin 4D.

Semaphorin 4D, also known as CD100, is a transmembrane protein that belongs to the semaphorin gene family. Semaphorin 4D is expressed on the cell surface as a homodimer, but upon cell activation Semaphorin 4D can be released from the cell surface via proteolytic cleavage to generate sSEMA4D, a soluble form of the protein, which is also biologically active. See Suzuki et al., *Nature Rev. Immunol.* 3:159-167 (2003); Kikutani et al., *Nature Immunol.* 9:17-23 (2008). In some embodiments, the human Semaphorin 4D amino acid sequence is SEQ ID NO:1 and the nucleotide sequence is SEQ ID NO:2. Information about Semaphorin 4D gene sequences and variants can also be found in the NCBI gene database. See, e.g., https://www.ncbi.nlm.nih-.gov/gene/(gene ID: 10507).

In certain embodiments, Semaphorin 4D is expressed on the surface of or secreted by a cell. In another embodiment, Semaphorin 4D is membrane bound. In another embodiment, Semaphorin 4D is soluble. In another embodiment, Semaphorin 4D may include a full-sized Semaphorin 4D or a fragment thereof, or a Semaphorin 4D variant polypeptide, wherein the fragment of Semaphorin 4D or Semaphorin 4D variant polypeptide retains some or all functional properties of the full-sized Semaphorin 4D.

The full-sized human Semaphorin 4D protein is a homodimeric transmembrane protein consisting of two polypeptide chains of 150 kDa. Semaphorin 4D belongs to the semaphorin family of cell surface receptors and is also referred to as CD100. Both human and mouse Semaphorin 4D are proteolytically cleaved from their transmembrane form to generate 120-kDa soluble forms, indicating the existence of two Semaphorin 4D isoforms (Kumanogoh et al., *Cell Science* 116(7):3464 (2003)). Semaphorins consist of soluble and membrane-bound proteins that were originally defined as axonal-guidance factors which play an important role in establishing precise connections between neurons and their appropriate target. Structurally considered a class IV semaphorin, Semaphorin 4D consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

In one embodiment, the invention provides a method of inhibiting tumor-mediated immunosuppression in a subject undergoing immunotherapy, comprising administering to the subject a therapeutically effective amount of an agent that inhibits the activity of Semaphorin 4D. In some embodiments, the immunotherapeutic agent comprises T cells.

In some embodiments, the inhibition of Semaphorin 4D decreases the level of myeloid-derived suppressor cells in the tumor microenvironment. In some embodiments, the myeloid-derived suppressor cells have a phenotype that is $CD33^+$, $CD11b^+$, and $HLA\text{-}DR^{-/low}$. In some embodiments, the inhibition of Semaphorin 4D results in one or more of the following effects:

i) an increase in T cell proliferation;
ii) an increase in IFN-γ levels;
iii) a decrease in IL-4 levels;
iv) a decrease in arginase-1 production by $CD33^+$myeloid cells;
v) a decrease in NO production by $CD33^+$myeloid cells;
vi) a decrease in IL-10 by $CD33^+$myeloid cells;
vii) a decrease in TGF-β1 production by $CD33^+$myeloid cells;
viii) a decrease in TGF-β1 production by tumor cells.
ix) an increase in effector Th1 T cells ($CD4^+Tbet^+$);
x) an increase in cytotoxic T cells ($CD8^+Tbet^+$); and
xi) a decrease in Tregs cells ($CD4^+CD25^+FoxP3^+$).

The term "subject" as used herein is not limiting and is used interchangeably with patient. In some embodiments, the subject refers to animals, such as mammals. For example, mammals contemplated include humans, primates, dogs, cats, sheep, cattle, goats, pigs, horses, chickens, mice, rats, rabbits, guinea pigs, and the like. The terms "subject" and "patient."

As used herein, "treat" and all its forms and tenses (including, for example, treating, treated, and treatment) can refer to therapeutic or prophylactic treatment. In certain aspects of the invention, those in need thereof of treatment include those already with a pathological condition of the invention (including, for example, a cancer), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the pathological condition. In other certain aspects of the invention, those in need thereof of treatment include, those in which a pathological condition is to be prevented, in which case treating refers to administering a therapeutically effective amount of a composition to a subject (including, for example, a human or other mammal in need of treatment) at risk of developing a disease or condition such as cancer.

In accordance with the invention, a "therapeutically effective amount" or "effective amount" is administered to the subject. As used herein a "therapeutically effective amount"

or "effective amount" is an amount sufficient to decrease, suppress, or ameliorate one or more symptoms associated with the disease or condition.

"Cancer" refers to leukemias, lymphomas, carcinomas, and other malignant tumors of potentially unlimited growth that can expand locally by invasion and potentially systemically by metastasis. Examples of cancers include, but are not limited to, cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor. In some embodiments, the cancer is head and neck cancer. In some embodiments, the cancer is lymphoma.

In some embodiments, the subject is administered one or more anti-cancer agents and/or radiotherapy in combination with the agent that inhibits Semaphorin 4D.

In some embodiments, the anti-cancer agent is an immunotherapeutic agent. In some embodiments, administering the agent that inhibits tumor-mediated immunosuppression caused by Semaphorin 4D can bolster the effectiveness of the immunotherapeutic anti-cancer agent administered to the subject.

The cancer immunotherapy is not limiting and can include one or more immunotherapies. There are several different approaches to immunotherapy. For example, immunotherapies can include monoclonal antibodies, checkpoint inhibitors/immune modulators, therapeutic cancer vaccines, oncolytic viruses, adoptive T cell transfer, cytokines, and adjuvant immunotherapy.

In certain embodiments, the combination of therapeutic agents discussed herein may be administered concurrently as a single composition in a pharmaceutically acceptable carrier, or concurrently as separate compositions with each agent in a pharmaceutically acceptable carrier. In another embodiment, the combination of therapeutic agents can be administered sequentially. The duration of time separating administrations in sequential administrations is not necessarily limiting.

In some embodiments, the agent that inhibits Semaphorin 4D is combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28).

The agent that inhibits Semaphorin 4D can be further combined with a vaccination protocol. Many experimental strategies for vaccination against tumors have been devised (see Rosenberg, S. (2000) *Development of Cancer Vaccines, ASCO Educational Book Spring:* 60-62; Logothetis, C., 2000, *ASCO Educational Book Spring:* 300-302; Khayat, D. (2000) *ASCO Educational Book Spring:* 414-428; Foon, K. (2000) *ASCO Educational Book Spring:* 730-738; see also Restifo and Sznol, *Cancer Vaccines*, Ch. 61, pp. 3023-3043 in DeVita et al. (eds.), 1997, *Cancer: Principles and Practice of Oncology. Fifth Edition*). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg (1999) Immunity 10:281-7). In many cases, these tumor specific antigens are differentiation antigens expressed in the tumors and in the cell from which the tumor arose. More importantly, many of these antigens can be shown to be the targets of tumor specific T cells found in the host. In certain embodiments, the agent that inhibits Semaphorin 4D may be used in conjunction with one or more recombinant proteins and/or peptides expressed in a tumor in order to generate an immune response to these proteins. These proteins are normally viewed by the immune system as self-antigens and are, therefore, tolerant to them. The tumor antigen may also include the protein telomerase, which is required for the synthesis of telomeres of chromosomes and which is expressed in more than 85% of human cancers and in only a limited number of somatic tissues (Kim et al. (1994) *Science* 266: 2011-2013). These somatic tissues may be protected from immune attack by various means. Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with Semaphorin 4D blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs may also be transduced by genetic means to express these tumor antigens as well. DCs have also been fused directly to tumor cells for the purposes of immunization (Kugler et al. (2000) *Nature Medicine* 6:332-336). As a method of vaccination, DC immunization may be effectively further combined with the agent that inhibits Semaphorin 4D to activate more potent anti-tumor responses.

Non-limiting examples of tumor vaccines that can also be used include peptides possible head and neck cancer antigens, such as p53, melanoma-associated antigens (MAGEs) such as MAGE-3, NY-ESO-1, cyclin B1, caspase-8, SART-1, carcino-embryonal antigen, and extracellular matrix metalloproteinase inducer (EMMPRIN) (CD147). The peptides can be coupled with antigen presenting cells, such as dendritic cells in some embodiments.

Semaphorin 4D inhibiting agents can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor specific responses. The T cell arm of these responses could be augmented by the use of a Semaphorin 4D inhibiting agents. In some embodiments, antigen may be delivered directly to DCs by the use of bispecific antibodies which bind to tumor antigen and a dendritic cell specific cell surface marker.

In another embodiment, a Semaphorin 4D inhibiting agent can be used in conjunction with anti-neoplastic antibodies, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), Kadcyla® (ado-trastuzumab emtansine), Perjeta® (pertuzumab), Adcetris® (brentuximab vedotin), Erbitux® (cetuximab), Vectibix® (panitumumab), Gazyva® (obinutuzumab), Arzerra® (ofatumumab), Cyramza® (ramucirumab), Blincyto® (blinatumomab) nimotuzumab, panitumumab, zalutumumab, cetuximab, matuzumab, figitumumab, bavituximab, Ch14.18, and rilotumumab. In some embodiments, the antibody can be bound to a toxin. By way of example and not wishing to be bound by theory, treatment with an anti-cancer antibody or an anti-cancer antibody conjugated to a toxin can lead to cancer cell death (e.g., tumor cells) which would potentiate an immune response mediated by Semaphorin 4D inhibiting agents. In an exemplary embodiment, a treatment of a hyperproliferative disease (e.g., a cancer tumor) may include an anti-cancer antibody in combination with a Semaphorin 4D inhibiting agent, concurrently or sequentially or any combination thereof, which may potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl, J. et al. (1986) *J Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). In another example, antibodies to each of these entities may be further combined with Semaphorin 4D inhibiting agents to counteract the effects of immunosuppressive agents and favor anti-tumor immune responses by the host.

In another embodiment, a Semaphorin 4D inhibiting agent can be used in conjunction with one or more checkpoint inhibitors or immune modulators. Checkpoint inhibitors/immune modulators can make cancer cells more susceptible to attack by the immune system. Checkpoint inhibitors and immune modulators include CTLA-4 inhibitors such as Yervoy® and tremelimumab, PD-1/PD-L1 inhibitors such as Keytruda®, Opdivo®, MPDL3280A and MEDI4736, LAG-3 inhibitors and KIR inhibitors. In some embodiments, the immune modulator is selected from CD27 inhibitors and GITR inhibitors.

Other antibodies that may be used to activate host immune responsiveness can be further used in combination with Semaphorin 4D inhibiting agents. These include molecules on the surface of dendritic cells that activate DC function and antigen presentation. Anti-CD40 antibodies are able to substitute effectively for T cell helper activity (Ridge, J. et al. (1998) *Nature* 393: 474-478) and can be used in conjunction with Semaphorin 4D inhibiting agents (Ito, N. et al. (2000) *Immunobiology* 201 (5) 527-40). Activating antibodies to T cell costimulatory molecules, such as OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. In some embodiments, combined Semaphorin 4D blockade can be used to increase the effectiveness of the donor engrafted tumor specific T cells.

In some embodiments, the subject is administered Semaphorin 4D inhibiting agents in combination with T cells. There are also several treatment protocols that involve ex vivo activation and expansion of antigen specific T cells and adoptive transfer of these cells into recipients in order to generate antigen-specific T cells against tumor. Adoptive T cell transfer is an anti-cancer approach that enhances the natural cancer-fighting ability of the body's T cells by removing immune system cells, growing and/or making changes to them outside of the body, and then re-infusing them back into the patient. In some embodiments, T cells can be collected from a sample of a patient's tumor and multiplied in a laboratory. In some embodiments, T cells can be taken out of the body and genetically modified to attack antigens on cancer cells. In some embodiments, T cells can be taken out of the body and equipped with special receptors called chimeric antigen receptors (CARs); when given back to the patient, these "CAR T cells" recognize and attack cancer cells.

In some embodiments, the Semaphorin 4D inhibiting agent can be used in conjunction with oncolytic virus immununotherapy. An oncolytic virus is virus that can activate a greater immune response.

In some embodiments, the Semaphorin 4D inhibiting agent can be used in conjunction with one or more cytokines. In some embodiments, the cytokine is selected from IL-2 and IFN-alpha.

The agent that inhibits Semaphorin 4D may also be combined with standard cancer treatments. For example, Semaphorin 4D blockade may be effectively combined with chemotherapeutic regimes. In these instances, it may be possible to reduce the dose of other chemotherapeutic reagent administered (Mokyr et al. (1998) *Cancer Research* 58: 5301-5304). In some embodiments, chemotherapeutic compounds should result in increased levels of tumor antigen in the antigen presentation pathway as a result of increased cell death. Other combination therapies that may result in synergy with Semaphorin 4D blockade through cell death include radiation, surgery, or hormone deprivation. Each of these protocols creates a source of tumor antigen in the host. Angiogenesis inhibitors may also be combined with Semaphorin 4D blockade.

In some embodiments, the anti-cancer agent is selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cab ozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Carmubris (Carmustine), Carmustine, Carmustine Implant, Casodex (Bicalutamide), CeeNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Margibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

In some embodiments, the anti-cancer agent is selected from gefitinib, erlotinib or cilengitide.

In some embodiments, the therapeutically effective amount of an agent that inhibits the activity of Semaphorin 4D is an antibody. The term "antibody" is used to refer to any antibody like molecule that has an antigen binding region, and includes full length antibody molecules, antibody fragments such as Fab', Fab, F(ab')2, single domain antibodies (DABs), Fv, scFv (single chain Fv), and the like. The techniques for preparing and using various antibody based constructs and fragments are well known in the art. Means for preparing and characterizing antibodies are also well known in the art (see, e.g., *Antibodies: A Laboratory Manual*, Cold Spring Harbor Laboratory, 1988; incorporated herein by reference).

Monoclonal antibodies (mAbs) as used herein also include sequences corresponding to human antibodies, animal antibodies, and combinations thereof. The term "chimeric antibody," as used herein, includes antibodies that have variable regions derived from an animal antibody, such as a rat or mouse antibody, fused to another molecule, for example, the constant domains derived from a human antibody. One type of chimeric antibodies, "humanized antibodies," have had the variable regions altered (through mutagenesis or CDR grafting) to match (as much as possible) the known sequence of human variable regions. CDR grafting involves grafting the CDRs from an antibody with desired specificity onto the FRs of a human antibody, thereby replacing much of the non-human sequence with human sequence. Humanized antibodies, therefore, more closely match (in amino acid sequence) the sequence of known human antibodies. By humanizing mouse monoclonal antibodies, the severity of the human anti-mouse antibody, or HAMA, response is diminished.

Antibodies that bind Semaphorin 4D have been described in the art. See, for example, US Publ. Nos. 2008/0219971 A1, US 2010/0285036 A1, and US 2006/0233793 A1, International Patent Applications WO 93/14125, WO 2008/100995, and WO 2010/129917, and Herold et al., *Int. Immunol.* 7(1): 1-8 (1995), each of which is herein incorporated in its entirety by reference. Such antibodies can be used in the methods of the present invention. In some embodiments, the antibody is a monoclonal antibody. In some embodiments, the antibody is a mouse monoclonal antibody. In some embodiments, the antibody is clone 30/CD100 (Cat #610670) (BD Biosciences PharMingen, San Diego, Calif.). In some embodiments, the antibody is clone eBio133-1C6 (Cat #14-1009) (eBioscience, San Diego, Calif.). In some embodiments, the antibody comprises one or more complementarity determining regions (CDRs) identical to the CDRs of clone 30/CD100. In some embodiments, the antibody comprises one or more complementarity determining regions (CDRs) identical to the CDRs of clone eBio133-1C6.

In certain embodiments, an anti-Semaphorin 4D antibody for use in the methods provided herein binds human, murine, or both human and murine Semaphorin 4D. Also useful are antibodies which bind to the same epitope as any of the aforementioned antibodies and/or antibodies which competitively inhibit binding or activity of any of the aforementioned antibodies.

In some embodiments, it may be desirable to "humanize" the antibody in order to attenuate any adverse immune reaction. Humanized antibodies can be produced, for example by replacing an immunogenic portion of an antibody with a corresponding, but non-immunogenic portion (i.e., chimeric antibodies). See, e.g., Robinson et al., WO/1987/002671; Akira et al., EP Application 184,187; Taniguchi, EP Application 171,496; Morrison et al., EP Application 173,494; Neuberger et al., WO 86/01533; Cabilly et al., EP Application 125,023, all of which are incorporated herein by reference. In some embodiments, the agent that inhibits Semaphorin 4D is a humanized antibody. In some embodiments, the antibody is a humanized antibody of antibody clone 30/CD100. In some embodiments, the antibody is a humanized antibody of antibody clone eBio133-1C6 In some embodiments, the antibody is a fully human antibody.

In some embodiments, the Semaphorin 4D inhibitory agent useful in the methods of the invention comprises a nucleic acid molecule that comprises a nucleotide sequence that binds to at least a portion of a nucleotide sequence of Semaphorin 4D. The nucleic acid molecule can be of any length, so long as at least part of the molecule hybridizes sufficiently to Semaphorin 4D mRNA. The nucleic acid molecule can bind to any region of Semaphorin 4D mRNA. In some embodiments, the nucleic acid molecule binds to a particular domain of Semaphorin 4D mRNA. In some embodiments, the nucleotide sequence of human Semaphorin 4D is shown in SEQ ID NO:2 (GenBank Accession No. U60800.1). In some embodiments, a region of the nucleic acid molecule is at least 70%, 75%, 80%, 85%, 90%, 91%, 92%, 93%, 94%, 95%, 96%, 97%, 98% or 99% complementary to at least a portion of SEQ ID NO:2. In some embodiments, the portion of SEQ ID NO:2 comprises SEQ ID NO:4 (5'-GGCCTGAGGACCTTGCAGAAGA-3'), corresponding to a portion of Homo sapiens semaphorin 41) (SEMA4D), Homo sapiens semaphorin 4D (SEMA4D), transcript variant 1, mRNA NCBI Reference Sequence: NM_006378.3 (SEQ ID NO:5) and transcript variant 2, mRNA NCBI Reference Sequence: NM_001142287.1 (SEQ ID NO:6). In some embodiments, a region of the nucleic acid molecule is 100% complementary to SEQ ID NO:4.

In some embodiments, the composition can comprise a DNA molecule, such as an antisense DNA molecule. In some embodiments, the composition can comprise an RNA molecule, such as an anti-sense RNA molecule, a small interfering RNA (siRNA) molecule, or small hairpin RNA (shRNA) molecule, which may or may not be comprised on a vector, including a viral vector (such as an adeno-associated viral vector, an adenoviral vector, a retroviral vector, or a lentiviral vector) or a non-viral vector. In some embodiments, the expression of the DNA or RNA molecule may be regulated by a regulatory region specific to one or more types of cancer.

A target sequence on a target mRNA can be selected from a given cDNA sequence corresponding to the Semaphorin 4D, in some embodiments, beginning 50 to 100 nt downstream (i.e., in the 3' direction) from the start codon. The target sequence can, however, be located in the 5' or 3' untranslated regions, or in the region nearby the start codon.

In one embodiment, the Semaphorin 4D inhibitory agent comprises a nucleic acid molecule that comprises a nucleotide sequence that binds to at least a portion of a nucleotide sequence of Semaphorin 4D mRNA. In some embodiments, the nucleic acid molecule is a DNA. In some embodiments, the nucleic acid molecule is an RNA.

In some embodiments, the composition comprises an anti-sense DNA. Anti-sense DNA binds with mRNA and prevents translation of the mRNA. The anti-sense DNA can be complementary to a portion of Semaphorin 4D mRNA. In some embodiments, the anti-sense DNA is complementary to the entire reading frame of Semaphorin 4D. In some embodiments, the anti-sense DNA is complementary to the entire reading frame of SEQ ID NO:2. In some embodiments, the antisense DNA is complementary to a portion of SEQ ID NO:2. In some embodiments, the antisense DNA is at least about 15 nucleotides, at least about 20 nucleotides, at least about 25 nucleotides, at least about 30 nucleotides, at least about 35 nucleotides, at least about 40 nucleotides, at least about 50 nucleotides, at least about 75 nucleotides, at least about 100 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1500 nucleotides, at least about 2000 nucleotides, at least about 2500 nucleotides, at least about 3000 nucleotides, at least about 3500 nucleotides, or at least about 4000 nucleotides.

In some embodiments, the composition comprises an anti-sense RNA. Anti-sense RNA binds with mRNA and prevents translation of the mRNA. The anti-sense RNA can be complementary to a portion of Semaphorin 4D mRNA. In some embodiments, the anti-sense RNA is complementary to the entire reading frame of Semaphorin 4D. In some embodiments, the anti-sense RNA is complementary to the entire reading frame of SEQ ID NO:2. In some embodiments, the antisense RNA is complementary to a portion of SEQ ID NO:2. In some embodiments, the antisense RNA is at least about 15 nucleotides, at least about 20 nucleotides, at least about 25 nucleotides, at least about 30 nucleotides, at least about 35 nucleotides, at least about 40 nucleotides, at least about 50 nucleotides, at least about 75 nucleotides, at least about 100 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1500 nucleotides, at least about 2000 nucleotides, at least about 2500 nucleotides, at least about 3000 nucleotides, at least about 3500 nucleotides, or at least about 4000 nucleotides.

In some embodiments, the composition is an siRNA targeting Semaphorin 4D. SiRNAs are small single or dsRNAs that do not significantly induce the antiviral response common among vertebrate cells but that do induce target mRNA degradation via the RNAi pathway. The term siRNA refers to RNA molecules that have either at least one double stranded region or at least one single stranded region and possess the ability to effect RNA interference (RNAi). It is specifically contemplated that siRNA can refer to RNA molecules that have at least one double stranded region and possess the ability to effect RNAi. The dsRNAs (siRNAs) may be generated by various methods including chemical synthesis, enzymatic synthesis of multiple templates, digestion of long dsRNAs by a nuclease with RNAse III domains, and the like. An "siRNA directed to" at least a particular region of Semaphorin 4D means that a particular Semaphorin 4D siRNA includes sequences that result in the reduction or elimination of expression of the target gene, i.e., the siRNA is targeted to the region or gene.

The nucleotide sequence of the siRNA is defined by the nucleotide sequence of its target gene. The Semaphorin 4D siRNA contains a nucleotide sequence that is essentially identical to at least a portion of the target gene. In some embodiments, the siRNA contains a nucleotide sequence that is completely identical to at least a portion of the Semaphorin 4D gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

In some embodiments, a Semaphorin 4D siRNA comprises a double stranded structure, the sequence of which is "substantially identical" to at least a portion of the target gene. "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated by standard practices in the art.

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. In some embodiments, there is 100% sequence identity between the dsRNA for use as siRNA and at least 15 contiguous nucleotides of the target gene, although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

In some embodiments, the invention provides an Semaphorin 4D siRNA that is capable of triggering RNA interference, a process by which a particular RNA sequence is destroyed (also referred to as gene silencing). In specific embodiments, Semaphorin 4D siRNA are dsRNA molecules that are 100 bases or fewer in length (or have 100 base pairs or fewer in its complementarity region). In some embodiments, a dsRNA may be 15, 16, 17, 18, 19, 20, 21, 22, 23, 24, 25, 26, 27, 28, 29, 30, 40, 50, 60, 70, 80, 90, 100 110, 120, 130, 140, 150, 160, 170, 180, 190, 200, 225, 250, 275, 300, 325, 350, 375, 400, 450, 500, 550, 600, 650, 700, 750, 800, 850, 900, 950, or 1000 nucleotides or more in length. In certain embodiments, Semaphorin 4D siRNA may be approximately 21 to 25 nucleotides in length. In some cases, it has a two nucleotide 3' overhang and a 5' phosphate. The particular Semaphorin 4D RNA sequence is targeted as a result of the complementarity between the dsRNA and the particular Semaphorin 4D RNA sequence. It will be understood that dsRNA or siRNA of the disclosure can effect at least a 20, 30, 40, 50, 60, 70, 80, 90 percent or more reduction of expression of a targeted Semaphorin 4D RNA in a cancer cell. dsRNA of the invention (the term "dsRNA" will be understood to include "siRNA" and/or "candidate siRNA") is distinct and distinguishable from antisense and ribozyme molecules by virtue of the ability to trigger RNAi. Structurally, dsRNA molecules for RNAi differ from antisense and ribozyme molecules in that dsRNA has at least one region of complementarity within the RNA molecule. In some embodiments, the complementary (also referred to as "complementarity") region comprises at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 contiguous bases. In some embodiments, long dsRNA are employed in which "long" refers to dsRNA that are 1000 bases or longer (or 1000 base pairs or longer in complementarity region). The term "dsRNA" includes "long dsRNA", "intermediate dsRNA" or "small dsRNA" (lengths of 2 to 100 bases or base pairs in complementarity region) unless otherwise indicated. In some embodiments of the disclosure, dsRNA can exclude the use of siRNA, long dsRNA, and/or "intermediate" dsRNA (lengths of 100 to 1000 bases or base pairs in complementarity region).

It is specifically contemplated that a dsRNA may be a molecule comprising two separate RNA strands in which one strand has at least one region complementary to a region on the other strand. Alternatively, a dsRNA includes a molecule that is single stranded yet has at least one complementarity region as described above (such as when a single strand with a hairpin loop is used as a dsRNA for RNAi). For convenience, lengths of dsRNA may be referred to in terms of bases, which simply refers to the length of a single strand or in terms of base pairs, which refers to the length of the complementarity region. It is specifically contemplated that embodiments discussed herein with respect to a dsRNA comprised of two strands are contemplated for use with respect to a dsRNA comprising a single strand, and vice versa. In a two-stranded dsRNA molecule, the strand that has a sequence that is complementary to the targeted mRNA is referred to as the "antisense strand" and the strand with a sequence identical to the targeted mRNA is referred to as the "sense strand." Similarly, with a dsRNA comprising only a single strand, it is contemplated that the "antisense region" has the sequence complementary to the targeted mRNA, while the "sense region" has the sequence identical to the targeted mRNA. Furthermore, it will be understood that sense and antisense region, like sense and antisense strands, are complementary (i.e., can specifically hybridize) to each other.

Strands or regions that are complementary may or may not be 100% complementary ("completely or fully complementary"). It is contemplated that sequences that are "complementary" include sequences that are at least 50% complementary, and may be at least 50%, 60%, 70%, 80%, or 90% complementary. In some embodiments, siRNA generated from sequence based on one organism may be used in a different organism to achieve RNAi of the cognate target gene. In other words, siRNA generated from a dsRNA that corresponds to a human gene may be used in a mouse cell if there is the requisite complementarity, as described above. Ultimately, the requisite threshold level of complementarity to achieve RNAi is dictated by functional capability. It is specifically contemplated that there may be mismatches in the complementary strands or regions. Mismatches may number at most or at least 1, 2, 3, 4, 5, 6, 7, 8, 9, 10, 11, 12, 13, 14, 15, 16, 17, 18, 19, 20, 21, 22, 23, 24, 25 residues or more, depending on the length of the complementarity region.

In some embodiments, the single RNA strand or each of two complementary double strands of a dsRNA molecule may be of at least or at most the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or more (including the full-length of a particular's gene's mRNA without the poly-A tail) bases or base pairs. If the dsRNA is composed of two separate strands, the two strands may be the same length or different lengths. If the dsRNA is a single strand, in addition to the complementarity region, the strand may have 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more bases on either or both ends (5' and/or 3') or as forming a hairpin loop between the complementarity regions.

In some embodiments, the strand or strands of dsRNA are 100 bases (or base pairs) or less. In specific embodiments, the strand or strands of the dsRNA are less than 70 bases in length. With respect to those embodiments, the dsRNA strand or strands may be from 5-70, 10-65, 20-60, 30-55, 40-50 bases or base pairs in length. A dsRNA that has a complementarity region equal to or less than 30 base pairs (such as a single stranded hairpin RNA in which the stem or complementary portion is less than or equal to 30 base pairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 base pairs or fewer. In some cases, a dsRNA may be processed in the cell into siRNA.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the disclosure can comprise a 3' overhang. As used herein, a "3' overhang" refers to at least one unpaired nucleotide extending from the 3'-end of a duplexed RNA strand.

Thus, in some embodiments, the Semaphorin 4D siRNA of the invention comprises at least one 3' overhang of from 1 to about 6 nucleotides (which includes ribonucleotides or deoxynucleotides) in length, from 1 to about 5 nucleotides in length, from 1 to about 4 nucleotides in length, or from about 2 to about 4 nucleotides in length.

In some embodiments in which both strands of the Semaphorin 4D siRNA molecule comprise a 3' overhang, the length of the overhangs can be the same or different for each strand. In some embodiments, the 3' overhang is present on both strands of the siRNA, and is 2 nucleotides in length. For example, each strand of the Semaphorin 4D siRNA of the invention can comprise 3' overhangs of dithymidylic acid ("TT") or diuridylic acid ("uu").

In order to enhance the stability of the present Semaphorin 4D siRNA, the 3' overhangs can be also stabilized against degradation. In some embodiments, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

In some embodiments, the Semaphorin 4D siRNA of the invention comprises the sequence AA(N19)TT or NA(N21), where N is any nucleotide. These Semaphorin 4D siRNA comprise approximately 30-70% GC, and in some embodiments comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the Semaphorin 4D siRNA of the invention comprises the sequence NAR(N17)YNN, where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

In some embodiments, the Semaphorin 4D siRNA of the disclosure can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the worldwide web at a website maintained by Dr. Thomas Tuschl, Department of Cellular Biochemistry, AG 105, Max-Planck-Institute for Biophysical Chemistry, 37077 Gottingen, Germany, and can be found by accessing the web site of the Max Planck Institute and searching with the keyword "siRNA." Thus, in some embodiments, the sense strand of the present siRNA comprises a nucleotide sequence identical to any contiguous stretch of about 19 to about 25 nucleotides in the target mRNA.

In some embodiments of the invention, the Semaphorin 4D siRNA targets the Semaphorin 4D ORF sequence: 5'-CAAGACGCTGCAGTTCGTTAA-3' (SEQ ID NO:7). In some embodiments, the siRNA molecule is complementary to SEQ ID NO:7.

In some embodiments, the Semaphorin 4D inhibitory agent useful in the methods of the invention comprises an shRNA molecule that targets Semaphorin 4D mRNA (Semaphorin 4D shRNA). shRNA is an artificial RNA molecule with a tight hairpin turn that can be used to silence target gene expression via RNA interference (RNAi). In certain cases, expression of Semaphorin 4D shRNA in cells is achieved through delivery of non-viral vectors (such as plasmids or bacterial vectors) or through viral vectors. shRNA is useful because it has a relatively low rate of degradation and turnover.

In some embodiments, the oligonucleotide used to knockdown Semaphorin 4D protein levels using shRNA is 5'-GGCCTGAGGACCTTGCAGAAGA-3' (SEQ ID NO:3). In order to obtain long-term gene silencing, expression vectors that continually express siRNAs in stably transfected mammalian cells can be used (Brummelkamp et al., *Science* 296: 550-553, 2002; Lee et al., *Nature Biotechnol.* 20:500-505, 2002; Miyagishi, M, and Taira, K. *Nature Biotechnol.* 20:497-500, 2002; Paddison, et al., *Genes & Dev.* 16:948-958, 2002; Paul et al., *Nature Biotechnol.* 20:505-508, 2002; Sui et al., *Proc. Natl. Acad. Sci. USA* 99(6):5515-5520, 2002; Yu et al., *Proc. Natl. Acad. Sci. USA* 99(9):6047-6052, 2002). Many of these plasmids have been engineered to express shRNAs lacking poly (A) tails. Transcription of shRNAs is initiated at a polymerase III (pol III) promoter and is believed to be terminated at position 2 of a 4-5-thymine transcription termination site. Upon expression, shRNAs are thought to fold into a stem-loop structure with 3' UU-overhangs. Subsequently, the ends of these shRNAs are processed, converting the shRNAs into ~21 nt siRNA-like molecules. The siRNA-like molecules can, in turn, bring about gene-specific silencing in the transfected mammalian cells.

The length of the stem and loop of shRNAs can be varied. In some embodiments, stem lengths could range anywhere from 25 to 29 nucleotides and loop size could range between 4 to 23 nucleotides without affecting silencing activity. Moreover, presence of G-U mismatches between the two strands of the shRNA stem does not necessarily lead to a decrease in potency.

In some embodiments, the present invention is directed towards methods of administering subjects with compositions comprising expression vectors and/or chemically synthesized shRNA molecules that target Semaphorin 4D. In some embodiments, the composition comprises a nucleotide sequence expressing a small hairpin RNA (shRNA) molecule. In some embodiments, the shRNA molecule is expressed by an expression vector comprising SEQ ID NO:3. In some embodiments, the expression vector is a lentivirus expression vector.

In some embodiments, it is contemplated that nucleic acids or antibodies of the invention may be labeled. The label may be fluorescent, radioactive, enzymatic, or calorimetric. It is contemplated that a dsRNA may have one label attached to it or it may have more than one label attached to it. When more than one label is attached to a dsRNA, the labels may be the same or be different. If the labels are different, they may appear as different colors when visualized. The label may be on at least one end and/or it may be internal. Furthermore, there may be a label on each end of a single stranded molecule or on each end of a dsRNA made of two separate strands. The end may be the 3' and/or the 5' end of the nucleic acid. A label may be on the sense strand or the sense end of a single strand (end that is closer to sense region as opposed to antisense region), or it may be on the antisense strand or antisense end of a single strand (end that is closer to antisense region as opposed to sense region). In some cases, a strand is labeled on a particular nucleotide (G, A, U, or C). When two or more differentially colored labels are employed, fluorescent resonance energy transfer (FRET) techniques may be employed to characterize the dsRNA.

Labels contemplated for use in several embodiments are non-radioactive. In many embodiments of the invention, the labels are fluorescent, though they may be enzymatic, radioactive, or positron emitters. Fluorescent labels that may be used include, but are not limited to, BODIPY, Alexa Fluor, fluorescein, Oregon Green, tetramethylrhodamine, Texas Red, rhodamine, cyanine dye, or derivatives thereof. The labels may also more specifically be Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, DAPI, 6-FAM, Killer Red, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, TET, Tetramethylrhodamine, and/or Texas Red. A labeling reagent is a composition that comprises a label and that can be incubated with the nucleic acid to effect labeling of the nucleic acid under appropriate conditions. In some embodiments, the labeling reagent comprises an alkylating agent and a dye, such as a fluorescent dye. In some embodiments, a labeling reagent comprises an alkylating agent and a fluorescent dye such as Cy3, Cy5, or fluorescein (FAM). In still further embodiments, the labeling reagent is also incubated with a labeling buffer, which may be any buffer compatible with physiological function (i.e., buffers that is not toxic or harmful to a cell or cell component) (termed "physiological buffer").

In some embodiments, the nucleic acids of the invention can be modified. In some embodiments, the nucleic acids can be modified to include a phosphorothioate (PS) backbone. The modification to the backbone can be throughout the molecule or at one or more defined sites. In some embodiments, the nucleic acids can be modified to encompass peptide nucleic acids (PNA). In some embodiments, the nucleic acids can be modified to encompass phosphorodiamidate morpholino oligomers (PMO).

In some embodiments, the nucleic acid molecules of the invention can include derivatives such as 5-oligonucleotides (phosphorothioate derivatives or S-oligos). S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer et al., *J. Org. Chem.* 55:4693-4698 (1990); and Iyer et al., *J. Am. Chem. Soc.* 112:1253-1254 (1990), the disclosures of which are fully incorporated by reference herein.

In some embodiments of the invention, a dsRNA has one or more non-natural nucleotides, such as a modified residue or a derivative or analog of a natural nucleotide. Any modified residue, derivative or analog may be used to the extent that it does not eliminate or substantially reduce (by at least 50%) RNAi activity of the dsRNA.

A person of ordinary skill in the art is well aware of achieving hybridization of complementary regions or molecules. Such methods typically involve heat and slow cooling of temperature during incubation, for example.

In some embodiments, the nucleic acid molecules of the present methods are encoded by expression vectors. The expression vectors may be obtained and introduced into a cell. Once introduced into the cell the expression vector is transcribed to produce various nucleic acids. Expression vectors include nucleic acids that provide for the transcription of a particular nucleic acid. Expression vectors include plasmid DNA, linear expression elements, circular expression elements, viral expression constructs (including adenoviral, adeno-associated viral, retroviral, lentiviral, and so forth), and the like, all of which are contemplated as being used in the compositions and methods of the present disclosure. In some embodiments one or at least 2, 3, 4, 5, 6, 7, 8, 9, 10 or more nucleic acid molecules binding to Semaphorin 4D RNA are encoded by a single expression construct. Expression of the nucleic acid molecules binding to Semaphorin 4D RNA may be independently controlled by at least 2, 3, 4, 5, 6, 7, 8, 9, 10 or more regulatory elements. In certain embodiments, at least 2, 3, 4, 5, 6, 7, 8, 9, 10 or more expression constructs can be introduced into a cell. Each expression construct can encode 1, 2, 3, 4, 5, 6, 7, 8, 9, 10 or more nucleic acid molecules binding to Semaphorin 4D RNA. In some embodiments, nucleic acid molecules binding to Semaphorin 4D RNA may be encoded as expression domains. Expression domains include a transcription control element, which may or may not be independent of other control or promoter elements; a nucleic acid; and optionally a transcriptional termination element.

Any suitable viral vector can be used in the methods of the invention. For example, vectors derived from adenovirus (AV); adeno-associated virus (AAV; including AAV serotypes); retroviruses (e.g, lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, are within the skill in the art. See, for example, Dornburg R (1995), *Gene Therap.* 2: 301-310; Eglitis M A (1988), *Biotechniques* 6: 608-614; Miller A D (1990), *Hum Gene Therap.* 1: 5-14; and Anderson W F (1998), *Nature* 392: 25-30, the entire disclosures of which are herein incorporated by reference.

The ability of a RNA of the claimed invention to cause RNAi-mediated degradation of the target mRNA can be evaluated using standard techniques for measuring the levels of RNA or protein in cells. For example, Semaphorin 4D siRNA of the invention can be delivered to cultured cells, and the levels of target mRNA can be measured by Northern blot or dot blotting techniques, or by quantitative RT-PCR. Alternatively, the levels of Semaphorin 4D protein in the cultured cells can be measured by ELISA or Western blot. A suitable cell culture system for measuring the effect of the present siRNA on target mRNA or protein levels may be utilized. RNAi-mediated degradation of Semaphorin 4D mRNA by an siRNA containing a given target sequence can also be evaluated with animal models, for example.

In other embodiments, the method comprises administering a composition comprising an antibody that reduces activity of Semaphorin 4D. As used herein, the term "antibody" includes any immunologic binding agent, such as IgG, IgM, IgA, IgD and IgE. Generally, IgG and/or IgM may be utilized because they are the most common antibodies in the physiological situation and because they are most easily made in a laboratory setting. The term "antibody" may be used to refer to any antibody-like molecule that has an antigen binding region, and includes antibody fragments such as Fab', Fab, F(ab')2, single domain antibodies (DABs), Fv, scFv (single chain Fv), and the like. Monoclonal and humanized antibodies are also contemplated in the disclosure.

In some embodiments, the nucleic acids can be administered to the subject either as naked nucleic acid, in conjunction with a delivery reagent, or as a recombinant plasmid or viral vector that expresses the nucleic acids. Delivery of nucleic acids or vectors to an individual may occur by any suitable means, but in specific embodiments it occurs by one of the following: cyclodextrin delivery system; ionizable lipids; DPC conjugates; GalNAc-conjugates; self-assembly of oligonucleotide nanoparticles (DNA tetrahedra carrying multiple siRNAs); or polymeric nanoparticles made of low-molecular-weight polyamines and lipids (see Kanasty et al. *Nature Materials* 12, 967-977 (2013) for review of same).

Suitable delivery reagents for administration in conjunction with the present nucleic acids or vectors include the Minis Transit TKO lipophilic reagent; lipofectin; lipofectamine; cellfectin; or polycations (e.g., polylysine), or liposomes. In specific embodiments, a particular delivery reagent comprises a liposome.

Liposomes can aid in the delivery of the present nucleic acids or vectors to a particular tissue, and can also increase the blood half-life of the nucleic acids. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9: 467; and U.S. Pat. Nos. 4,235,871, 4,501,728, 4,837,028, and 5,019,369, the entire disclosures of which are herein incorporated by reference.

In certain aspects, the liposomes encapsulating the present nucleic acids comprise a ligand molecule that can target the liposome to a particular cell or tissue at or near the site of interest. Ligands that bind to receptors prevalent in the tissues to be targeted, such as monoclonal antibodies that bind to surface antigens, are contemplated. In particular cases, the liposomes are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand. Opsonization-inhibiting moieties for use in preparing the liposomes of the disclosure are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example solid tumors, will efficiently accumulate these liposomes; see Gabizon, et al. (1988), *P.N.A.S., USA,* 18: 6949-53. In addition, the reduced uptake by the RES lowers the toxicity of stealth liposomes by preventing significant accumulation in the liver and spleen. Thus, liposomes of the invention that are modified with opsonization-inhibition moieties can deliver the present nucleic acids to tumor cells.

Opsonization inhibiting moieties suitable for modifying liposomes are preferably water-soluble polymers with a number-average molecular weight from about 500 to about 40,000 Daltons, and more preferably from about 2,000 to about 20,000 Daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

In some embodiments, the opsonization-inhibiting moiety is a PEG, PPG, or derivatives thereof. Liposomes modified with PEG or PEG-derivatives are sometimes called "PEGylated liposomes." The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH 3 and a solvent mixture such as tetrahydrofuran and water in a 30:12 ratio at 60 degrees C.

Recombinant plasmids that express nucleic acids of the invention are discussed above. Such recombinant plasmids can also be administered directly or in conjunction with a suitable delivery reagent, including the Minis Transit LT 1 lipophilic reagent; lipofectin; lipofectamine; cellfectin; polycations (e.g., polylysine) or liposomes.

The nucleic acids reducing the level of Semaphorin 4D of the invention can be administered to the subject by any suitable means. For example, the nucleic acids can be administered by gene gun, electroporation, or by other suitable parenteral or enteral administration routes, or by injection, for example, by intramuscular or intravenous injection.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intratumoral injection, intra-retinal injection or subretinal injection); subcutaneous injection or deposition including subcutaneous infusion (such as by osmotic pumps); direct (e.g., topical) application to the area at or near the site of interest, for example by a catheter or other placement device (e.g., a corneal pellet or a suppository, eye-dropper, or an implant comprising a porous, non-porous, or gelatinous material); and inhalation. In a particular embodiment, injections or infusions of the composition(s) are given at or near the site of disease.

The nucleic acids reducing the level of Semaphorin 4D of the invention can be administered in a single dose or in multiple doses. Where the administration of a composition is by infusion, the infusion can be a single sustained dose or can be delivered by multiple infusions. Injection of the agent directly into the tissue is at or near the site of need. Multiple injections of the agent into the tissue at or near the site of interest are encompassed within this disclosure.

One skilled in the art can also readily determine an appropriate dosage regimen for administering the nucleic acids reducing the level of Semaphorin 4D of the invention to a given subject. For example, the composition(s) can be administered to the subject once, such as by a single injection or deposition at or near the site of interest. In some embodiments, the composition(s) can be administered to a subject once or twice daily to a subject once weekly for a period of from about three to about twenty-eight days, in some embodiments, from about seven to about ten weeks. In some dosage regimens, the composition(s) is injected at or near the site of interest once a day for seven days. Where a dosage regimen comprises multiple administrations, it is understood that the effective amount of composition(s) administered to the subject can comprise the total amount of composition(s) administered over the entire dosage regimen.

In one embodiment, the present invention is directed towards a composition for treating cancer comprising an isolated nucleic acid that decreases the level and/or activity of Semaphorin 4D and a pharmaceutically acceptable carrier. In some embodiments, the nucleic acid comprises SEQ ID NO:3 or a fragment or derivative thereof capable of decreasing the level and/or activity of Semaphorin 4D.

The Semaphorin 4D inhibitory agents of the disclosure may be formulated as pharmaceutical compositions prior to administration to a subject, according to techniques known in the art. See, e.g., *Remington's Pharmaceutical Science,* 17th ed., Mack Publishing Company, Easton, Pa. (1985), the entire disclosure of which is herein incorporated by reference. In some embodiments, pharmaceutical compositions of the present invention are characterized as being at least sterile and pyrogen-free. As used herein, "pharmaceutical formulations" include formulations for human and veterinary use.

Pharmaceutical compositions of the disclosure can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like. For example, a solid pharmaceutical composition for oral administration can comprise any of the carriers and excipients listed above and 10-95%, or 25%-75%, of one or more compositions of the invention. In some embodiments, a pharmaceutical composition for aerosol (inhalational) administration can comprise 0.01-20% by weight or 1%-10% by weight, of one or more compositions of the invention encapsulated in a liposome as described above, and propellant. A carrier can also be included as desired; e.g., lecithin for intranasal delivery.

Methods of Screening for Anti-Cancer Agents

In some embodiments, an assay for Semaphorin 4D activity in cells can be used to determine the functionality of the Semaphorin 4D in the presence of an agent which may act as an inhibitor, and thus, agents that interfere with the activity of Semaphorin 4D can be identified.

In some embodiments, the Semaphorin 4D of the present invention is employed in a screening process for compounds which bind Semaphorin 4D or one of its binding partners or both and which inhibits the biological activity of the Semaphorin 4D interaction. Inhibitors of Semaphorin 4D are particularly advantageous and can be used in methods as therapeutic agents in the treatment of cancer, such as head and neck cancer and lymphoma.

By "inhibitor" is intended naturally occurring and/or synthetic agents capable of inhibiting the biological activity of Semaphorin 4D, which can include inhibiting transcription or translation of Semaphorin 4D mRNA.

In some embodiments, the screening procedures involve producing appropriate cells which produce Semaphorin 4D. Such cells can include cells from mammals, yeast, *Drosophila* or *E. coli*. In some embodiments, the cells express Semaphorin 4D endogenously. In other embodiments, the cells have been transfected or engineered to express Semaphorin 4D. In some embodiments, cells expressing Semaphorin 4D (or extracts or purified preparations from cells)

are contacted with a test compound to observe stimulation or inhibition of a functional response.

In some embodiments, assays can test binding of Semaphorin 4D to its targets or assays can involve competition with a competitor compound, such as a labeled competitor.

Potential antagonists are not limiting and examples include antibodies, peptides, carbohydrates, or small molecules which bind to Semaphorin 4D or its targets. These agents can be selected and screened 1) at random, 2) by a rational selection or 3) by design using for example, ligand modeling techniques (e.g., computer modeling).

For random screening, agents such as antibodies, peptides, carbohydrates, pharmaceutical agents and the like are selected at random and are assayed for their ability to bind to or block the interaction of the Semaphorin 4D to its targets or reduce expression of Semaphorin 4D.

Alternatively, agents may be rationally selected or designed. As used herein, an agent is said to be "rationally selected or designed" when the agent is chosen based on the configuration of the Semaphorin 4D or its targets.

In one aspect, the invention provides a method of screening for an anti-cancer agent which inhibits Semaphorin 4D, comprising: (a) contacting Semaphorin 4D; and (b) assaying the agent's effect on the Semaphorin 4D activity. In some embodiments, the activity to be tested is generation of myeloid-derived suppressor cells.

In one embodiment, the present invention is directed towards methods of screening for anti-cancer agents comprising i) contacting a cell culture medium comprising Semaphorin 4D and/or cells comprising Semaphorin 4D with the agent; ii) and assaying whether Semaphorin 4D activity is reduced, wherein if Semaphorin 4D activity is reduced, the agent has anti-cancer activity.

In some embodiments, the assaying of part ii) comprises culturing a cell population comprising myeloid cells in the cell culture medium and detecting the presence or absence of myeloid-derived suppressor cells, wherein if the level of myeloid-derived suppressor cells is reduced relative to a control sample lacking the agent, then the agent has anti-cancer activity. In some embodiments, the myeloid-derived suppressor cells have a phenotype that is $CD33^+$, $CD11b^+$, and $HLA\text{-}DR^{-/low}$. In some embodiments, the cell culture medium comprising Semaphorin 4D is a conditioned medium from a cancer cell line. In some embodiments, the cell culture medium is from a head and neck squamous cell carcinoma cell line. In some embodiments, the cell line is a human cell line. In some embodiments, the cell line is selected from the group consisting of HN4, HN6, HN13, and SCC-9.

In some embodiments, the cell population comprises total PBMC. In some embodiments, the cell population comprises total myeloid cells ($CD33^+$) isolated from PBMC.

In some embodiments, the candidate anti-cancer agent reduces the level of myeloid-derived suppressor cells by at least about 20%, 30%, 40%, 50%, 60%, 70%, 80%, 90%, or about 95% relative to a control lacking the agent.

In some embodiments, the agent is selected from a nucleic acid or an antibody. In some embodiments, the agent comprises a nucleotide sequence that binds to at least a portion of a nucleotide sequence of Semaphorin 4D, wherein the assaying of part ii) comprises detecting Semaphorin 4D mRNA and/or protein and comparing its level to a control sample lacking the agent.

Diagnostic/Prognostic Screening Assays

In another embodiment, the invention provides a method of monitoring progression of cancer in a subject, comprising obtaining the results of an assay that determines the presence of Semaphorin 4D in a tissue sample from the subject, wherein elevated levels of Semaphorin 4D compared to a tissue sample from a healthy donor indicate progression of the cancer in the subject.

In some embodiments, the cancer is selected from head and neck cancer and hematological malignancies, such as lymphoma. In some embodiments, the cancer is selected from the group consisting of squamous cell carcinoma of the head and neck (HNSCC), salivary gland adenocarcinomas (SGA), metastatic HNSCC, and metastatic SGA. In some embodiments, the subject has stage III or stage IV cancer.

The tissue sample is not particularly limiting. In some embodiments, the tissue sample comprises peripheral blood. In some embodiments, the tissue sample comprises cancer tissue. In some embodiments, the tissue sample comprises cancer tissue from head and neck cancer.

In some embodiments, Semaphorin 4D is detected by an antibody. In some embodiments, the antibody is clone 30/CD100 (Cat #610670) (BD Biosciences PharMingen, San Diego, Calif.). In some embodiments, the antibody is clone eBio133-1C6 (Cat #14-1009) (eBioscience, San Diego, Calif.). In some embodiments, the antibody is clone 133-1C6 (available through Novus Biosciences).

In some embodiments, Semaphorin 4D is detected by an ELISA (enzyme-linked immunosorbent assay) technique. In some embodiments, Semaphorin 4D is detected by immunohistochemistry.

In some embodiments, the method further comprises obtaining the results of an assay that determines the presence of Semaphorin 4D in a second tissue sample from the subject, wherein increasing levels of Semaphorin 4D in the second tissue sample compared to the tissue sample from the subject obtained from an earlier point in time indicate progression of the cancer in the subject. Additional tissue samples can be obtained at later periods of time in order to monitor progression by assaying for the presence of Semaphorin 4D in the tissue sample.

In some embodiments, an elevated level of expression of Semaphorin 4D corresponds to a positive pixel intensity of at least $1.5\times10^5$ by standardized digital analysis as described herein. The pixel intensity can be determined digitally by the Algorithm (Positive Pixel count v9) of the Leica Aperio software. The cut off value $1.5\times10^5$ was determined as the mean between the negative/low expression and the positive/high expression values (see the materials and methods of Example 3, below).

In some embodiments, the subject's tumor has a fibrotic peri-tumoral stroma. For example, stromal analysis for fibrosis can be carried out by a pathologist on H&E and IHC stained sections under light microscopy. For analysis of fibrosis in the tumor stroma, delicately fibrous stroma (+), moderately fibrotic (++) and densely fibrotic (+++) parameters can used. In some embodiments, the subject's tumor has a dense, fibrotic peri-tumoral stroma. In some embodiments, the stroma is analyzed by cell staining. In some embodiments, the stroma is stained with Picrosirius stain.

In some embodiments, the method further comprises obtaining the results of an assay that detects the presence or absence of tumor associated inflammatory cells that have elevated expression of Semaphorin 4D. In some embodiments, there is an inverse correlation between elevated Semaphorin 4D in the tissue and the presence of tumor associated inflammatory cells that have elevated expression of Semaphorin 4D.

In some embodiments, the method further comprises obtaining the results of an assay that detects the presence or absence of immune checkpoint molecules, such as PD-L1, in the tissue sample, wherein the tissue sample is cancer tissue.

In some embodiments, the cancer tissue is PD-L1$^{-ve/low}$. The level of PD-L1 can be assayed and measured relative to its expression in normal oral epithelium. In some embodiments, when the PD-L1 level is negative or low, the method further comprises administering to the subject an agent that inhibits the activity of Semaphorin 4D. In some embodiments, this agent is administered as a monotherapy.

In some embodiments, the tissue is positive for the presence of the immune checkpoint molecule, such as PD-L1. Since PD-L1 is negative in normal epithelium, in some embodiments, the cut off value for elevated PD-L1 (PD-L1$^{+ve/high}$) is strong focal expression ≥1% in tumor cells or in tumor associated inflammatory cells or both, and using a positive pixel intensity of at least $1.5 \times 10^5$ by standardized digital analysis as described above and in the Examples.

In some embodiments where the tissue is both positive for the immune checkpoint molecule and Semaphorin 4D, the method further comprises administering to the subject an agent that inhibits the activity of Semaphorin 4D and an agent that inhibits the immune checkpoint molecule. In one embodiment, the inhibitor is a PD-L1 inhibitor.

Sample Embodiments

This section describes exemplary compositions and methods of the invention, presented without limitation, as a series of paragraphs, some or all of which may be alphanumerically designated for clarity and efficiency. Each of these paragraphs can be combined with one or more other paragraphs, and/or with disclosure from elsewhere in this application, including the materials incorporated by reference, in any suitable manner. Some of the paragraphs below expressly refer to and further limit other paragraphs, providing without limitation examples of some of the suitable combinations.

1. A method of inhibiting tumor-mediated immunosuppression in a subject, comprising administering to the subject a therapeutically effective amount of an agent that inhibits the activity of Semaphorin 4D.

2. The method of paragraph 1, wherein the agent decreases the expression level of Semaphorin 4D.

3. The method of any of paragraphs 1-2, wherein the cancer is selected from head and neck cancer and lymphoma.

4. The method of any of paragraphs 1-3, wherein the inhibition of Semaphorin 4D decreases the level of myeloid-derived suppressor cells in the tumor microenvironment.

5. The method of any of paragraphs 1-4, wherein the myeloid-derived suppressor cells have a phenotype that is $CD33^+$, $CD11b^+$, and HLA-DR$^{-/low}$.

6. The method of any of paragraphs 1-5, wherein the inhibition of Semaphorin 4D results in one or more of the following effects:

i) an increase in T cell proliferation;

ii) an increase in IFN-γ levels;

iii) a decrease in IL-4 levels;

iv) a decrease in arginase-1 production by $CD33^+$myeloid cells;

v) a decrease in NO production by $CD33^+$myeloid cells;

vi) a decrease in IL-10 by $CD33^+$myeloid cells;

vii) a decrease in TGF-β1 production by $CD33^+$myeloid cells;

viii) a decrease in TGF-β1 production by tumor cells.

ix) an increase in effector Th1 T cells ($CD4^+Tbet^+$);

x) an increase in cytotoxic T cells ($CD8^+Tbet^+$); and xi) a decrease in Tregs cells ($CD4^+CD25^+FoxP3^+$).

7. The method of any of paragraphs 1-6, wherein the agent comprises a nucleic acid molecule that comprises a nucleotide sequence that binds to at least a portion of a nucleotide sequence of Semaphorin 4D.

8. The method of any of paragraphs 1-7, wherein the nucleotide sequence of Semaphorin 4D is SEQ ID NO:2.

9. The method of any of paragraphs 1-8, wherein a portion of the nucleic acid molecule is at least 70%, 75%, 80%, 85%, 90%, 91%, 92%, 93%, 94%, 95%, 96% 97%, 97%, 98% or 99% complementary to at least a portion of SEQ ID NO:2.

10. The method of any of paragraphs 1-9, wherein a portion of the nucleic acid molecule is 100% complementary to SEQ ID NO:4.

11. The method of any of paragraphs 1-10, wherein the agent comprises a DNA molecule or an RNA molecule.

12. The method of any of paragraphs 1-11, wherein the agent comprises an anti-sense DNA molecule or an anti-sense RNA molecule.

13. The method of any of paragraphs 1-12, wherein the agent comprises a small interfering RNA (siRNA) molecule.

14. The method of any of paragraphs 1-13, wherein the siRNA molecule targets the sequence CAAGACGCTGCAGTTCGTTAA (SEQ ID NO:7).

15. The method of any of paragraphs 1-14, wherein the agent comprises a small hairpin RNA (shRNA) molecule.

16. The method of any of paragraphs 1-15, wherein the agent comprises an expression vector comprising SEQ ID NO:3.

17. The method of any of paragraphs 1-16, wherein the expression vector is a lentivirus vector.

18. The method of any of paragraphs 1-17, wherein the agent comprises an antibody specifically binding to Semaphorin 4D.

19. The method of any of paragraphs 1-18, wherein the method further comprises administering to the subject an effective amount of an additional anti-cancer therapeutic agent.

20. The method of any of paragraphs 1-19, wherein the anti-cancer agent comprises an immunotherapeutic agent.

21. The method of any of paragraphs 1-20, wherein the immunotherapeutic agent comprises T cells.

22. A method of screening for an agent that has anti-cancer activity, comprising i) contacting a cell culture medium comprising Semaphorin 4D and/or cells comprising Semaphorin 4D with the agent; and ii) assaying whether Semaphorin 4D activity is reduced, wherein if Semaphorin 4D activity is reduced, the agent has anti-cancer activity.

23. The method of paragraph 22, wherein the assaying of part ii) comprises culturing a cell population comprising myeloid cells in the cell culture medium and detecting the presence or absence of myeloid-derived suppressor cells, wherein if the level of myeloid-derived suppressor cells is reduced relative to a control sample lacking the agent, then the agent has anti-cancer activity.

24. The method of paragraph 23, wherein the myeloid-derived suppressor cells have a phenotype that is $CD33^+$, $CD11b^+$, and HLA-DR$^{-/low}$.

25. The method of any of paragraphs 22-24, wherein the cell population comprises total PBMC.

26. The method of any of paragraphs 22-25, wherein the cell population comprises total myeloid cells ($CD33^+$) isolated from PBMC.

27. The method of any of paragraphs 22-26, wherein the cell culture medium comprising Semaphorin 4D is a conditioned medium from a head and neck squamous cell carcinoma cell line.

28. The method of paragraph 27, wherein the cell line is a human cell line. 29. The method of paragraph 28, wherein the cell line is selected from the group consisting of HN4, HN6, HN13, and SCC-9.

30. The method of paragraph 23, wherein the level of myeloid-derived suppressor cells is reduced at least about 50% relative to a control lacking the agent.

31. The method of any of paragraphs 22-30, wherein the agent is a nucleic acid molecule that comprises a nucleotide sequence that binds to at least a portion of a nucleotide sequence of Semaphorin 4D, wherein the assaying of part ii) comprises detecting Semaphorin 4D mRNA and/or protein and comparing its level to a control sample lacking the agent.

32. A method of monitoring progression of cancer in a subject, comprising obtaining the results of an assay that determines the presence of Semaphorin 4D in a tissue sample from the subject, wherein elevated levels of Semaphorin 4D compared to a tissue sample from a healthy donor indicate progression of the cancer in the subject.

33. The method of paragraph 32, wherein the tissue sample comprises peripheral blood.

34. The method of paragraph 32, wherein the tissue sample comprises cancer tissue.

35. The method of any of paragraphs 32-34, wherein the presence of Semaphorin 4D is detected by an antibody.

36. The method of any of paragraphs 32-35, wherein the Semaphorin 4D is detected by an ELISA (enzyme-linked immunosorbent assay) technique.

37. The method of any of paragraphs 32-35, wherein the Semaphorin 4D is detected by immunohistochemistry.

38. The method of any of paragraphs 32-37, wherein the method further comprises obtaining the results of an assay that determines the presence of Semaphorin 4D in a second tissue sample from the subject, wherein increasing levels of Semaphorin 4D in the second tissue sample compared to the tissue sample from the subject obtained from an earlier point in time indicate progression of the cancer in the subject.

39. The method of any of paragraphs 32-38, wherein the cancer is selected from head and neck cancer and lymphoma. 40. The method of any of paragraphs 32-39, wherein the cancer is head and neck cancer.

41. The method of any of paragraphs 32-40, wherein the cancer is selected from the group consisting of squamous cell carcinoma of the head and neck (HNSCC), salivary gland adenocarcinomas (SGA), metastatic HNSCC, and metastatic SGA.

42. The method of any of paragraphs 32-41, wherein the elevated level of expression of Semaphorin 4D corresponds to a positive pixel intensity of at least $1.5\times10^5$ by standardized digital analysis.

43. The method of any of paragraphs 32-42, wherein the subject has stage III or IV cancer.

44. The method of any of paragraphs 32-43, wherein the subject's tumor has a dense, fibrotic peri-tumoral stroma.

45. The method of any of paragraphs 32-44, wherein the dense, fibrotic peri-tumoral stroma is detected by cell staining.

46. The method of any of paragraphs 32-45, further comprising obtaining the results of an assay that detects the presence or absence of tumor associated inflammatory cells that have elevated expression of Semaphorin 4D.

47. The method of any of paragraphs 32-46, wherein there is an inverse correlation between elevated Semaphorin 4D in the tissue and the presence of tumor associated inflammatory cells that have elevated expression of Semaphorin 4D.

48. The method of any of paragraphs 32-47, further comprising obtaining the results of an assay that detects the presence or absence of an immune checkpoint molecule such as PD-L1 in the tissue sample, wherein the tissue sample is cancer tissue.

49. The method of any of paragraphs 32-48, wherein the cancer tissue is PD-L1$^{-ve/low}$.

50. The method of any of paragraphs 32-49, further comprising administering to the subject an agent that inhibits the activity of Semaphorin 4D.

51. The method of any of paragraphs 32-50, wherein the tissue is positive for the presence of the checkpoint molecule, such as PD-L1, wherein the cut off value for elevated PD-L1 (PD-L1$^{+ve/high}$) is strong focal expression ≥1% in tumor cells or in tumor associated inflammatory cells or both, and using a positive pixel intensity of at least $1.5\times10^5$ by standardized digital analysis.

52. The method of any of paragraphs 32-51, further comprising administering to the subject an agent that inhibits the activity of Semaphorin 4D and an agent that inhibits the checkpoint molecule.

53. The method of paragraph 52, wherein the checkpoint molecule is PD-L1.

In some embodiments, the methods of the present invention are combined with one or more other known treatments. For the treatment of cancer, one or more other known treatments can include radiation, surgery, chemotherapy or administration of other anti-cancer agents and combinations thereof.

Application of the teachings of the present invention to a specific problem is within the capabilities of one having ordinary skill in the art in light of the teaching contained herein. Examples of the compositions and methods of the invention appear in the following non-limiting Examples.

EXAMPLES

Example 1

Human Head and Neck Squamous Cell Carcinoma Associated Semaphorin 4D Induces Expansion of Myeloid Derived Suppressor Cells The present example investigated whether HNSCC derived Sema4D plays a role in inducing MDSC and examined its effect on T cell phenotype and function. It was found that Sema4D produced by the HNSCC HN6 and HN13 cell lines polarized myeloid cells into MDSC phenotype, which corresponded with a reduction in T cell proliferation and IFN-γ production. Furthermore, shRNA inhibition of Sema4D in HN6 resulted in a decrease in the production of the immunosuppressive factors; arginase-1, TGF-β, and IL-10 by myeloid cells and the recovery of autologous T cell proliferation, IFN-γ production, specifically leading to an increase in the effector T cell population and decrease in Tregs. These findings describe HNSCC-associated Sema4D production as one of the mechanisms by which the tumors induce MDSC, that subsequently mediate their immunosuppression effects on T cells.

Results

Figure 1B:
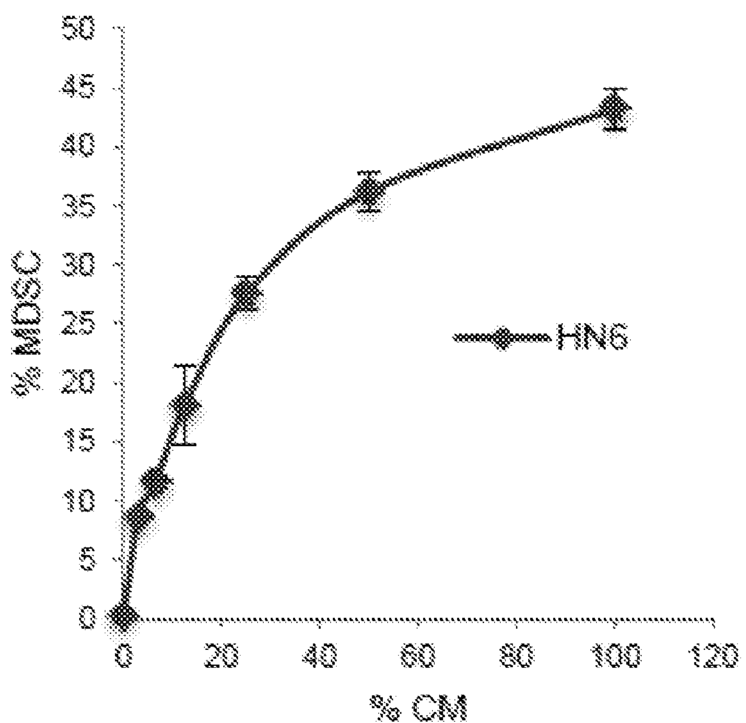
Figure 1C:
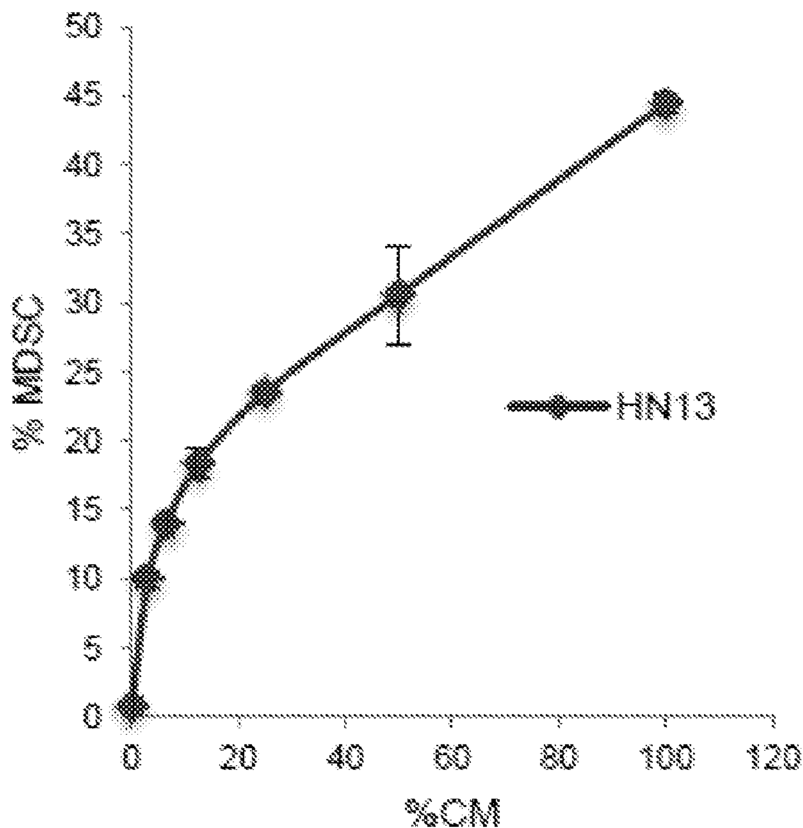
Figure 7A:
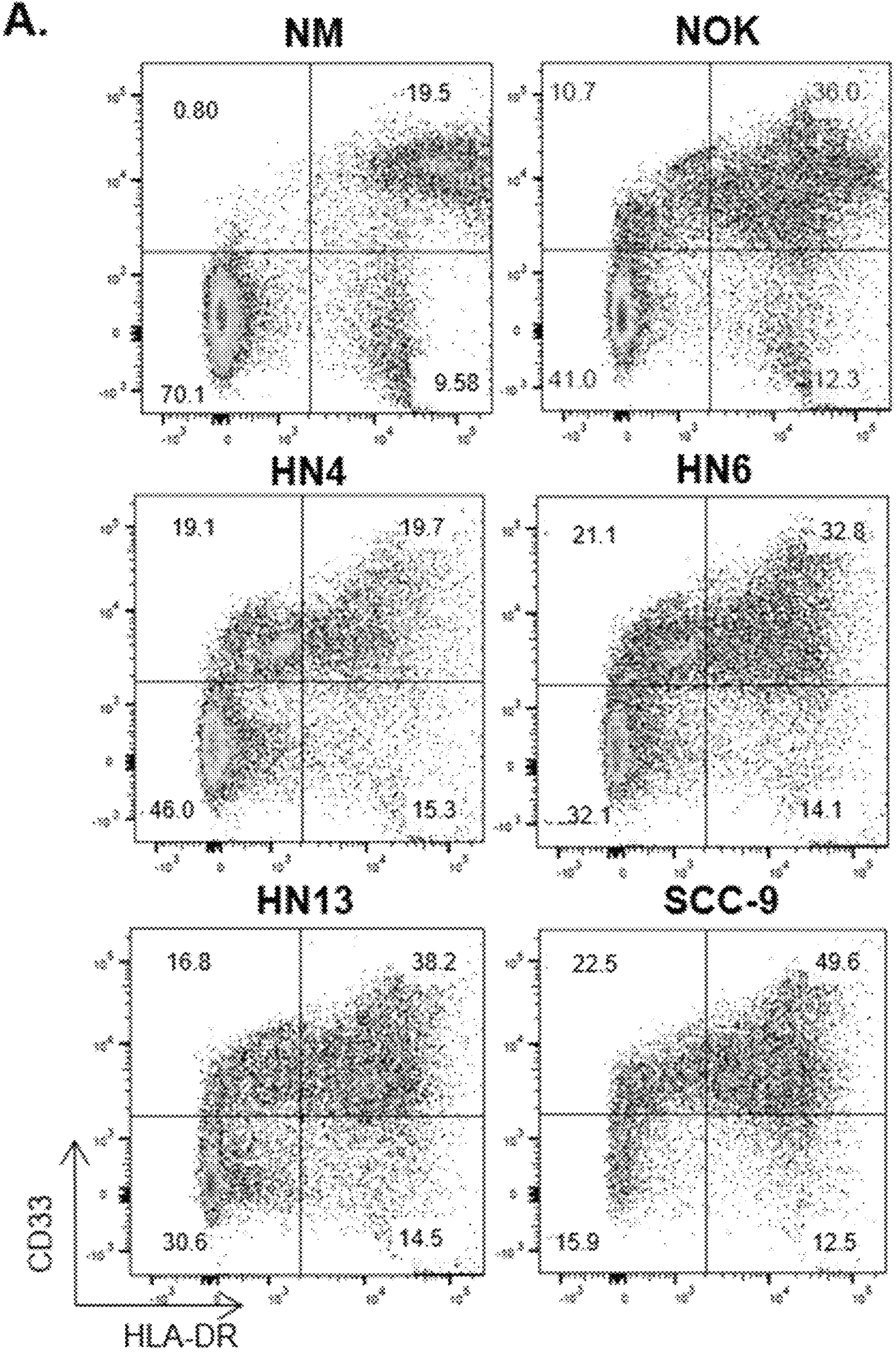
FIG. 7. HNSCC CM induces MDSC from total PBMC or myeloid cells of healthy donors and anti-Sema4D Ab treatment reduces its induction. (A) HNSCC CM induces MDSC from total PBMC. PBMC were separated by density gradient centrifugation then plated for 72 hrs in NM or CM from NOK versus CM of HN4, HN6, HN13 and SCC-9 cell lines. The average MDSC generation from PBMC was ~20%. For flow cytometry analysis total PBMC were gated followed by a $CD33^+$ HLA-$DR^{-/lo}$ gate. (B) Induction of MDSC from total $CD33^+$ cells by HNSCC cell line CM is decreased by anti-Sema4D Ab treatment. Total $CD33^+$ cells separated from PBMC using CD33 microbeads magnetic cell sorting (MACS), were cultured for 72 hrs in HNSCC HN4 and SCC-9 CM only (−), CM with IgG Isotype, or CM with anti-Sema4D antibody (10 ug/ml). Total myeloid cells were gated for $CD33^+$ $CD11b^+$ followed by a $CD11b^+$ HLA-$DR^{-/low}$ gate. For both experiments initial plating cell density was 1 ml of $2.5\times10^5$ in 24 well plate. NM: Normal media. CM: conditioned media.
Figure 7B:
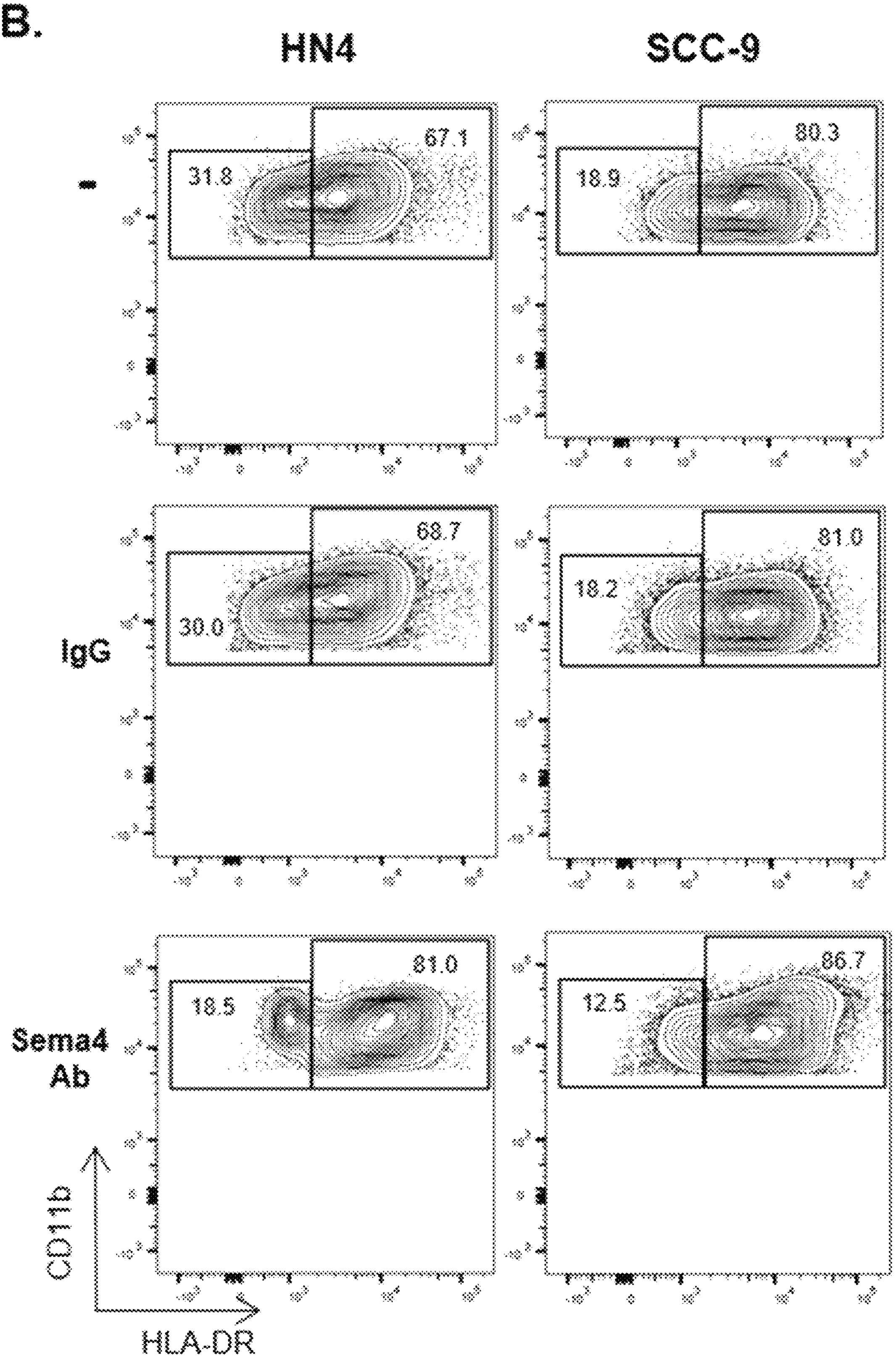

Sema4D Expressed by HNSCC Cell Lines Induces $CD33^+$, $CD11b^+$, HLA-$DR^{-/low}$ Cells To examine the effects of HNSCC-derived condition medium on myeloid differentiation, total human PBMC or total myeloid cells ($CD33^+$) isolated from PBMC were plated in conditioned medium from HNSCC cell lines HN4, HN6, HN13 and SCC-9. Total PBMC or separated myeloid cells cultured in HNSCC conditioned medium displayed markers characteristic of MDSC, namely $CD33^+$ $CD11b^+$ HLA-$DR^{-/low}$ compared to cells cultured in normal medium (NM) or NOK conditioned medium. The percentage of MDSC developed from total PBMC were ~20% (FIG. 7A), while that generated from $CD33^+$ myeloid cells averaged 30% depending on the HNSCC cell line and density used (FIG. 1A) (FIG. 7B). Moreover, titration of HN6 and HN13 derived conditioned medium with normal medium corresponded with a dose-dependent decrease in the MDSC population (FIG. 1B, 1C).

Figure 2A:
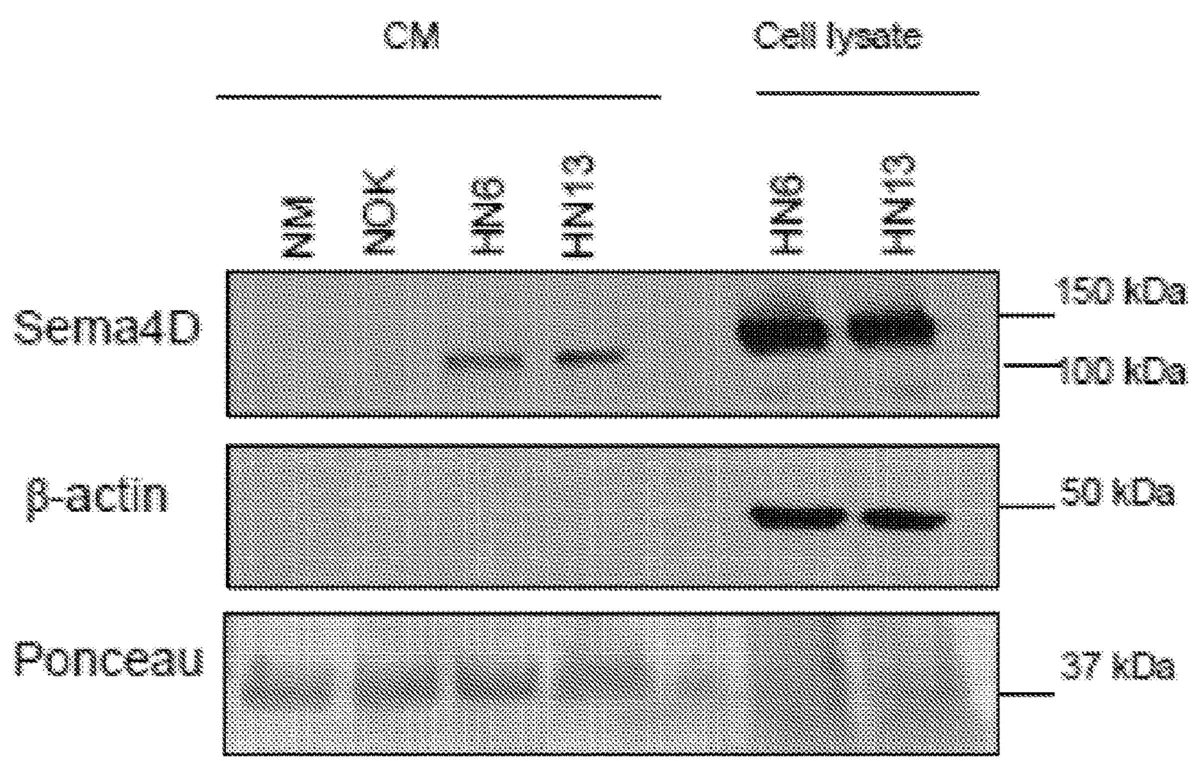
FIG. 2. Sema4D produced by HNSCC plays a role in MDSC induction. (A) Sema4D is secreted by HN6 and HN13 cell lines. CM and total cell lysates from HN6 and HN13 HNSCC cell lines were analyzed by Western blot. Ponceau staining was used as a control for protein loading prior to immunoblotting. β-actin served as control for cell lysates. (B) Anti-sema4D antibody treatment downregulates MDSC induction by HNSCC cells. $CD33^+$ cells were cultured in NM, NOK, HN6 and HN13 CM in the presence or absence of anti-Sema4D mAb (10 ug/ml) or isotype control mAb for 72 hrs. Cells were analyzed by flow cytometry by gating on $CD33^+CD11b^+$, then analyzed for $CD11b^+$ HLA-$DR^{-/low}$. The experiment was independently repeated twice. (C) Graphical presentation of 2 combined experiments, showing MDSC reduction ($CD33^+$ $CD11b^+$ HLA-$DR^{-/low}$) upon anti-Sema4D Ab treatment of HN6 and HN13 CM. Data normalized to MDSC in NM treated with IgG isotype.
Figure 2B:
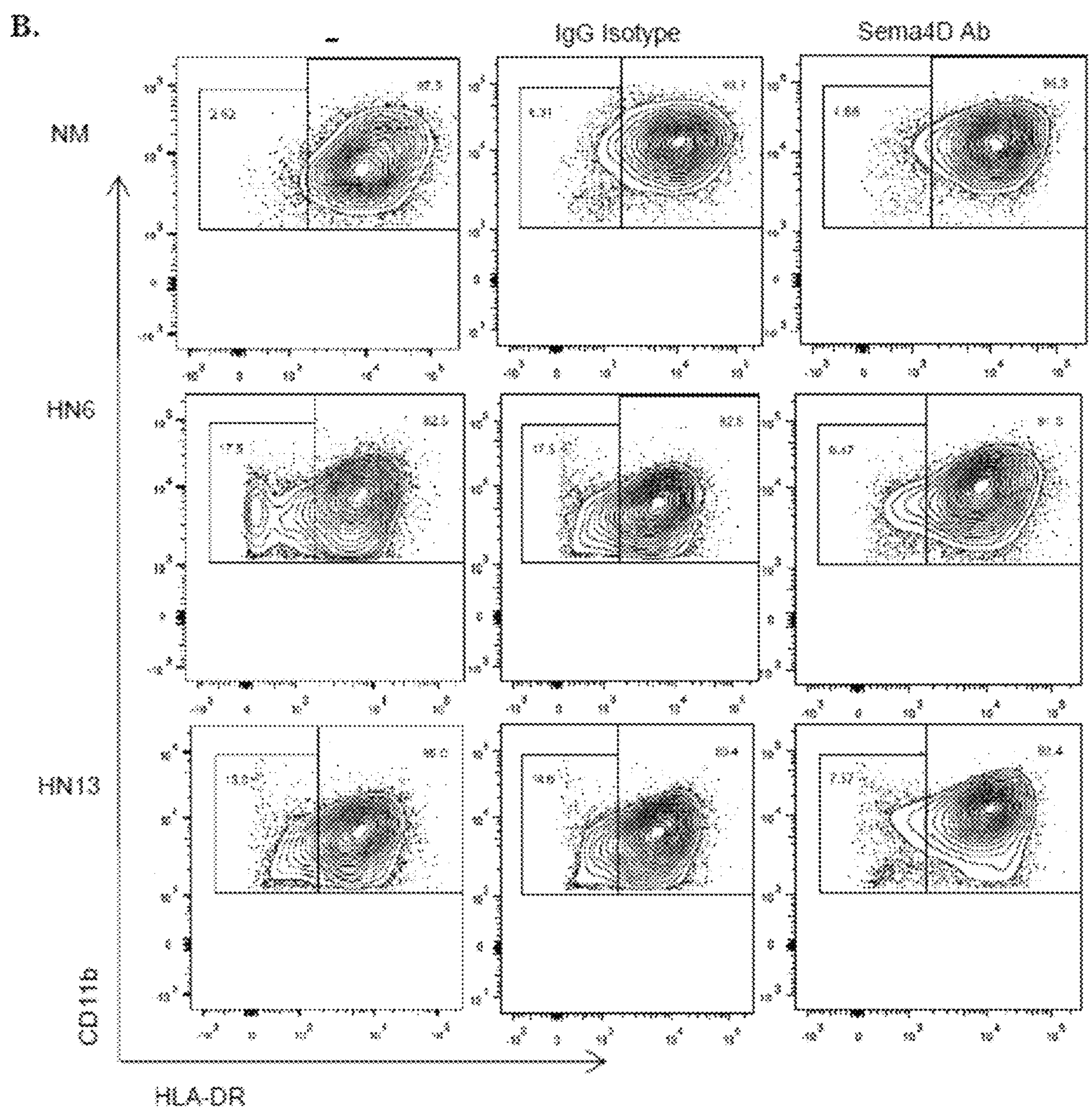
Figure 2C:
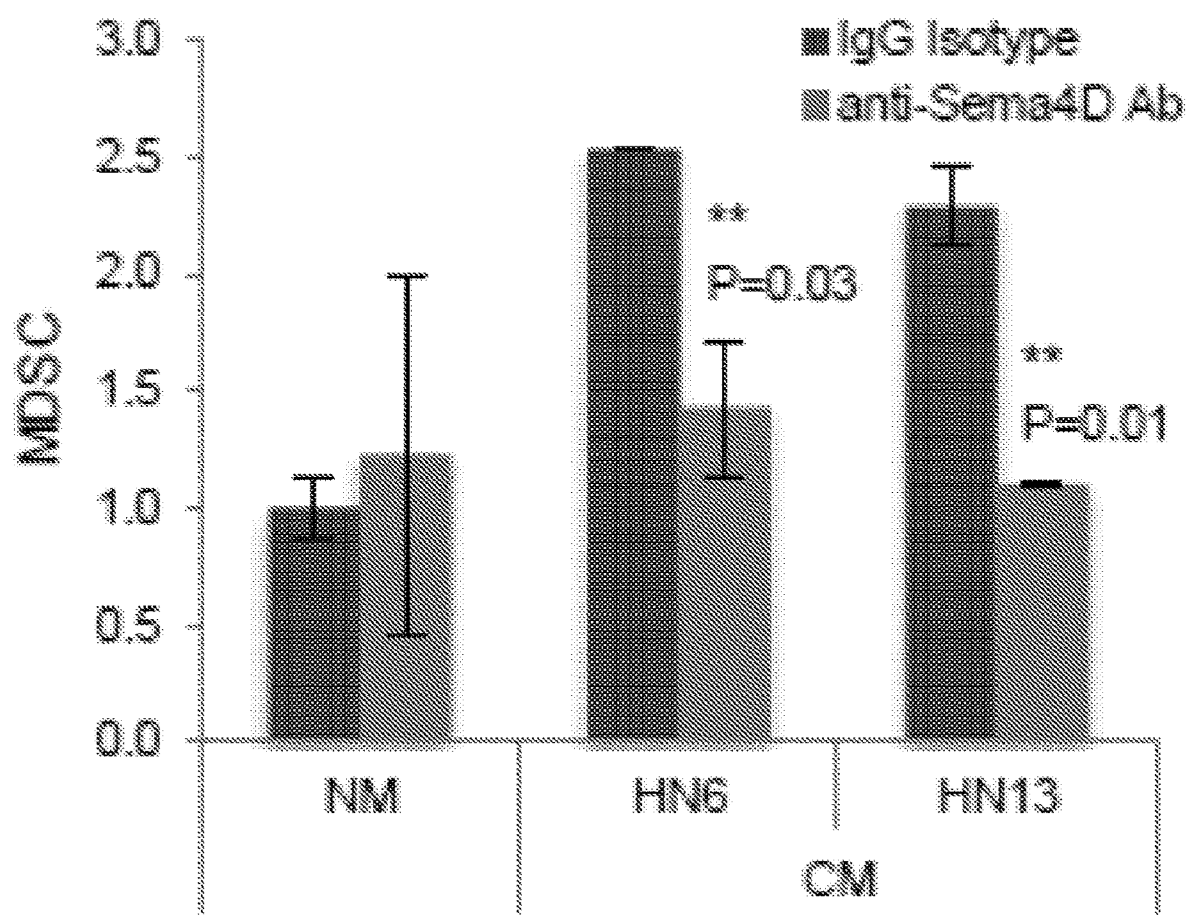

Several groups have recently described an immunomodulatory role for tumor produced pro-angiogenic factors (Chouaib et al. 2012. *Front Immunol* 3: 21). Given the immune modulatory role previously described for Sema4D in the immune system (Ishida et al. 2003. *Int Immunol* 15: 1027-1034; Chabbert-de Ponnat et al. 2005. *Int Immunol* 17: 439-447), we sought to investigate if the pro-angiogenic factor, Sema4D secreted by HNSCC (Basile et al. 2006. *Proc Natl Acad Sci USA* 103: 9017-9022), plays a role in the induction of $CD33^+$ $CD11^+$ HLA-$DR^{1/low}$ myeloid cells. Immunoblotting was performed on conditioned medium from HN6 and HN13 HNSCC cell lines and their cellular lysates as served as controls. We detected the cleaved form of Sema4D in the medium at ~120 KDa (FIG. 2A) as previously reported (Kumanogoh et al., 2003. *J Cell Sci* 116: 3463-3470). We then neutralized Sema4D in the HN4, HN6, HN13 and SCC-9 conditioned medium using anti-Sema4D antibody (clone 30/CD100), then used the medium to culture myeloid cells. Blocking Sema4D in HNSCC conditioned medium resulted in ~50% reduction in the MDSC population compared to cells growing in HNSCC conditioned medium pretreated with the isotype control mAb (FIG. 2B, 2C) (FIG. 7B).

Sema4D Inhibition Rescues MDSC Induced T Cell Suppression

Figure 3A:
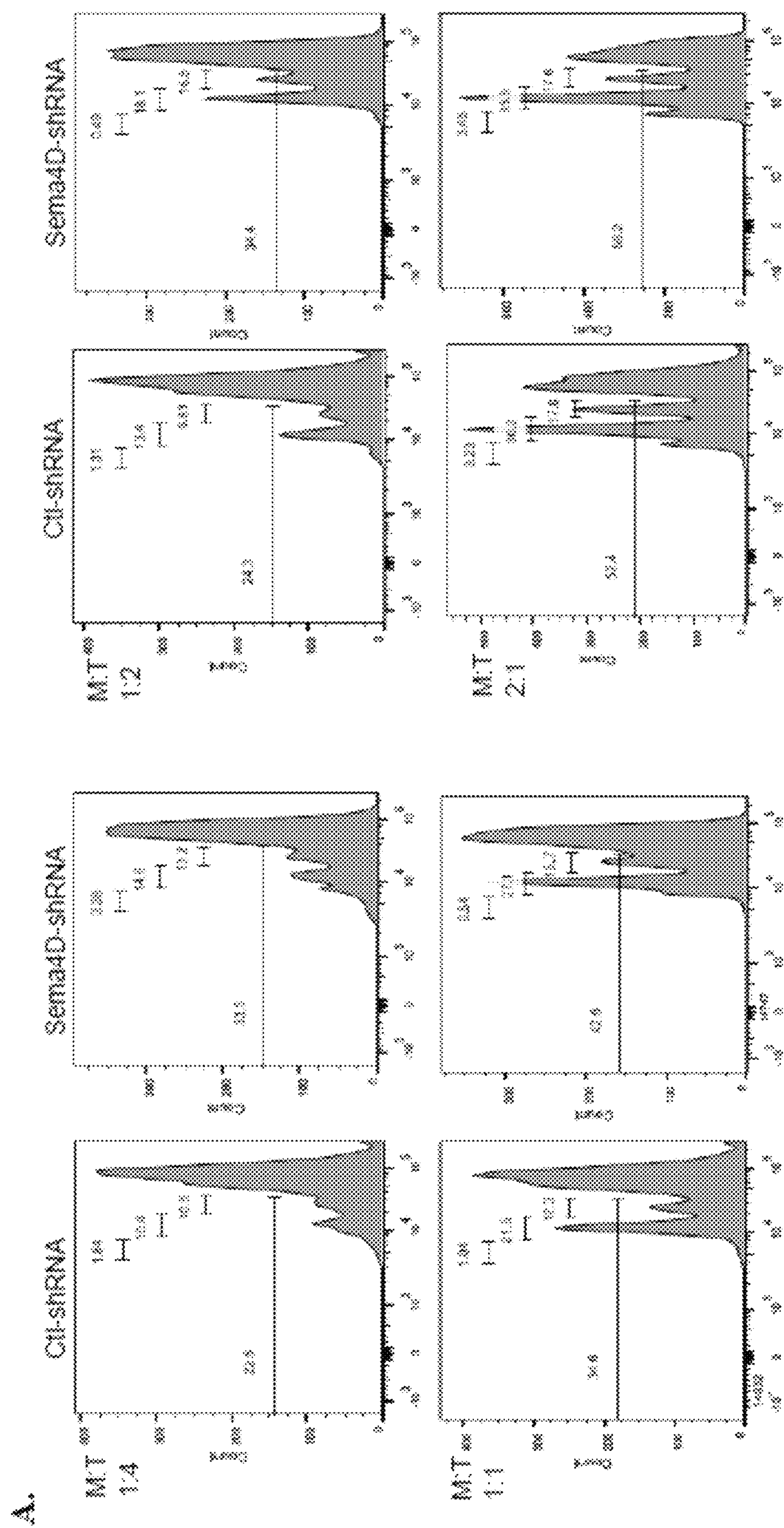
FIG. 3. Inhibition of Sema4D produced by HN6 rescues MDSC mediated T cell suppression. (A) Recovery of T cell proliferation following inhibition of Sema4D in HN6 cell line using lentivirus shRNA. T cells stained with CFSE and myeloid cells were added at the indicated ratios (M:T). Cells were co-cultured in CM from HN6 Sema4D-shRNA or HN6 Ctl-shRNA, and activated by anti-CD3/CD28 microbeads for 72 hrs. CFSE dilution in T cells was analyzed by FACS. (B) Graphical representation of flow cytometry data shown in A. Data normalized to activated T cells cultured alone in NM. The supernatants were collected to assess IFN-γ (C) and IL-4 (D) production using ELISA. Error bars indicate S.D. of triplicate assays.
Figure 3D:
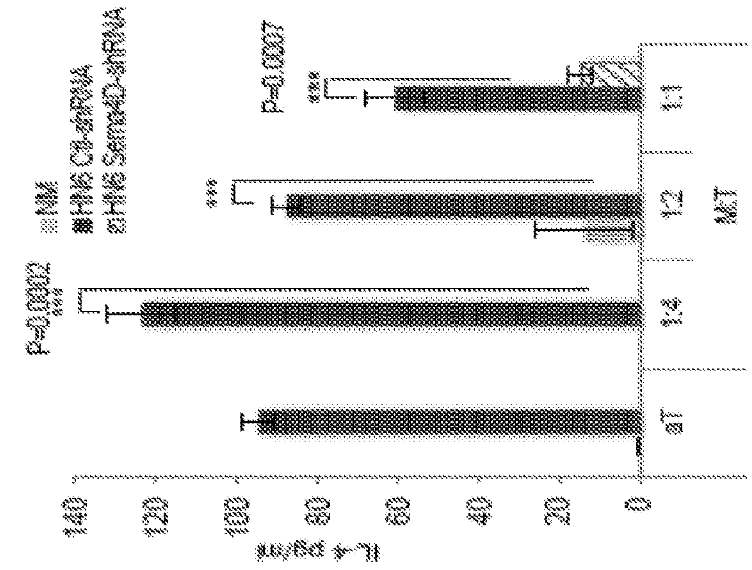
Figure 3C:
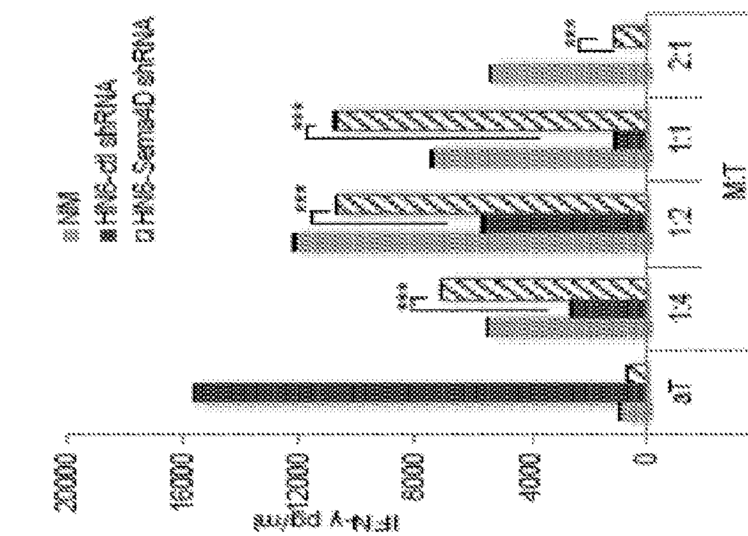
Figure 3B:
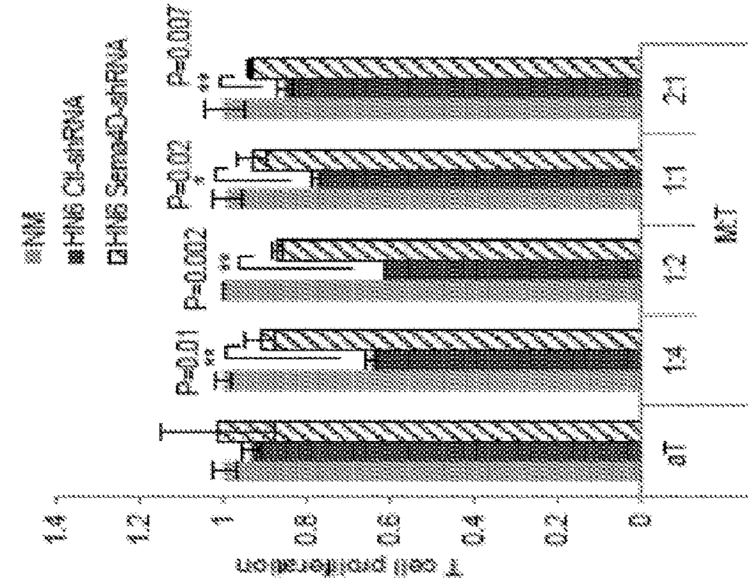
Figure 4A:
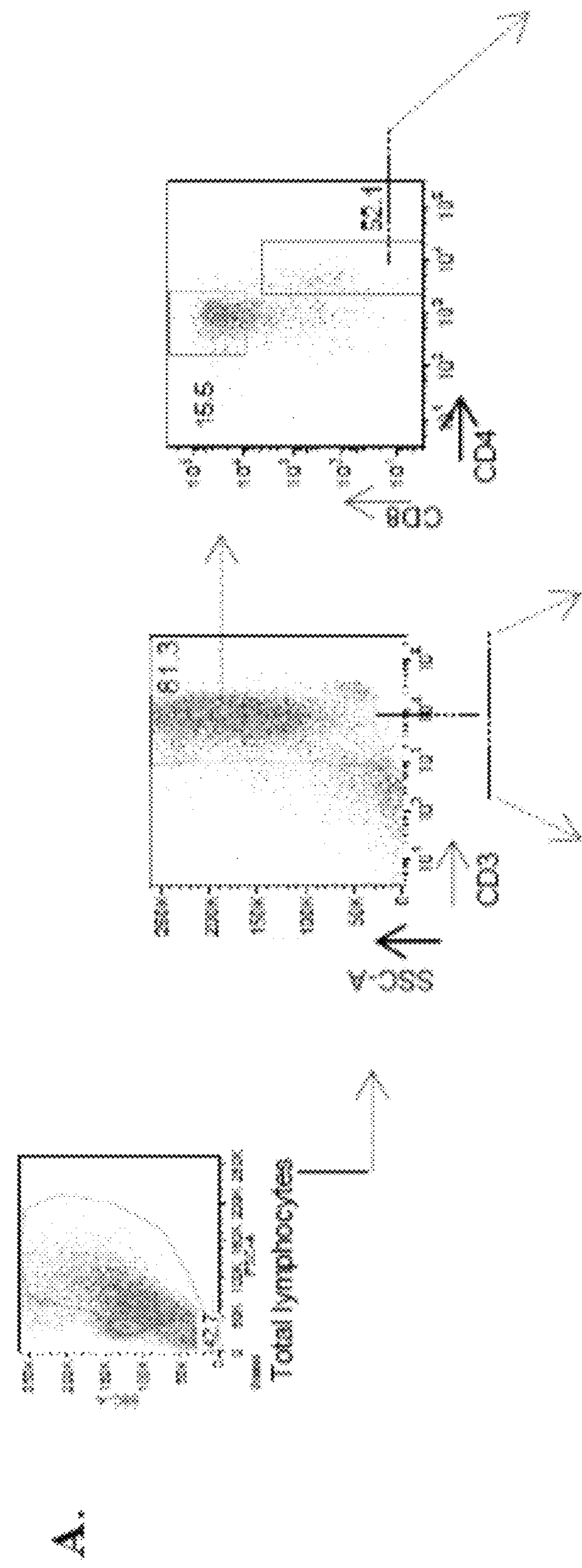
FIG. 4. Sema4D produced by HN6 induces an immune suppressive T cell phenotype. (A) T cells were co-cultured with myeloid cells at the indicated ratios, followed by CD3/CD28 activation for 72 hrs. Then cells were analyzed by flow cytometry. (A) The cells were gated on the myeloid and T cell subpopulations, followed by a second gate on $CD3^+$ cells. $CD3^+$ cells were then gated on (B) $CD4^+$T-$bet^+$ and (C) $CD8^+$T-$bet^+$. The $CD4^+$ population was gated on $CD25^+FoxP3^+$. Representative flow cytometry plots displaying percentage of recovery of (B) $CD3^+$ $CD4^+$ $Tbet^+$ effector cells (C) $CD3^+$ $CD8^+$ $Tbet^+$ effector cells and (D) decrease in $CD4^+$ $CD25^+$ $FoxP3^+$ Tregs in HN6 CM of Sema4D-shRNA versus Ctl-shRNA.
Figure 4B:
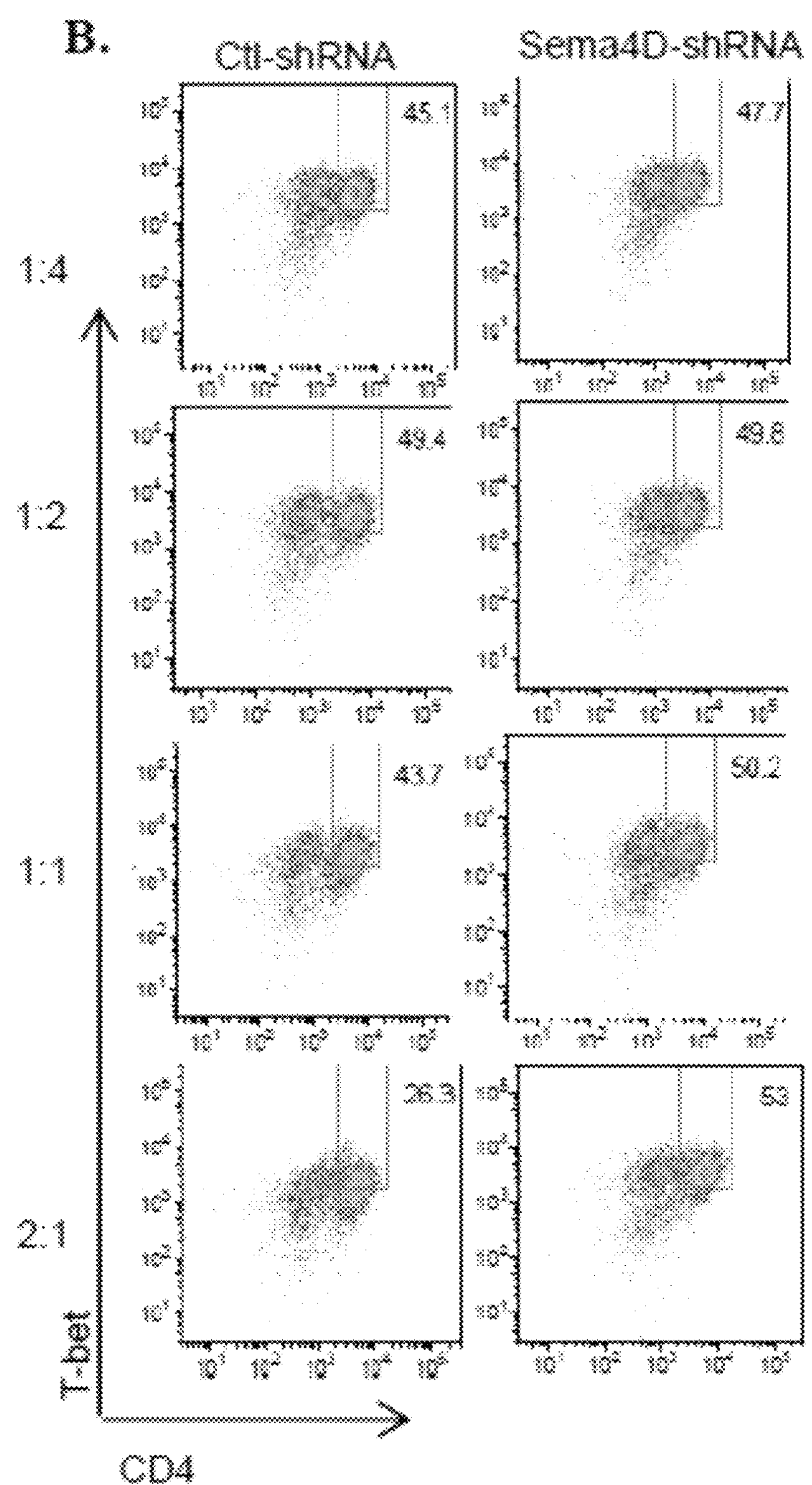
Figure 4C:
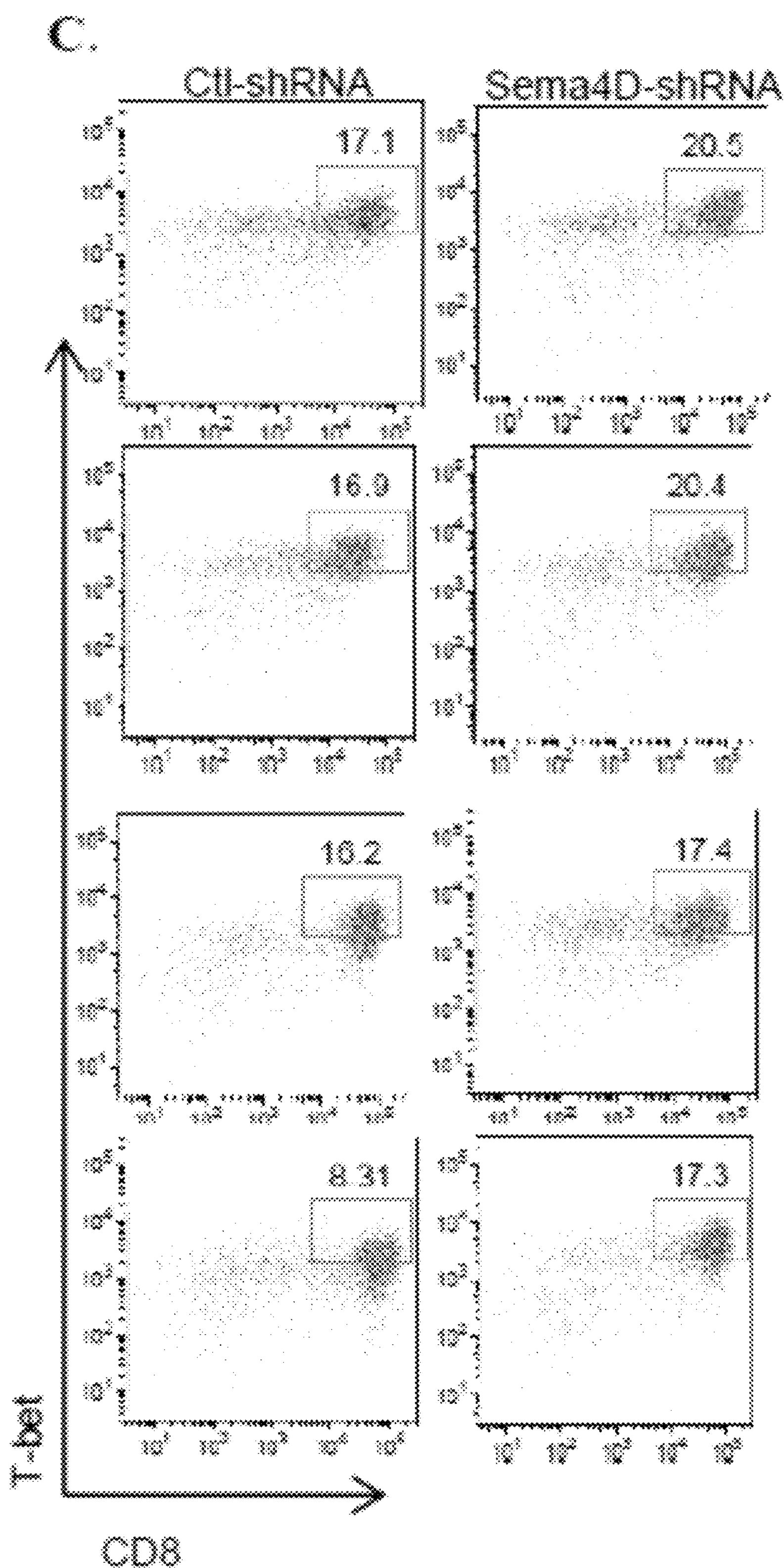
Figure 4D:
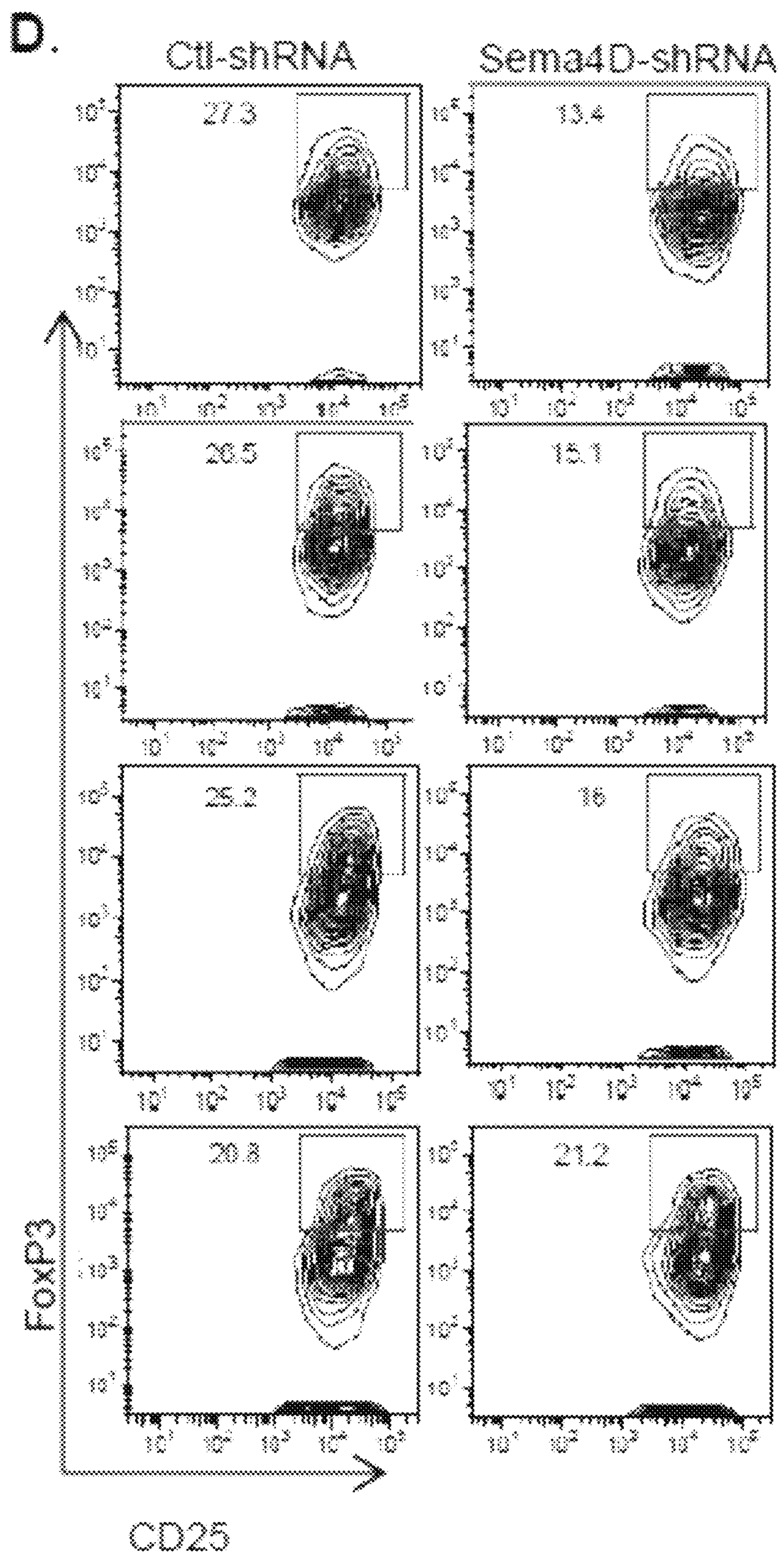
Figure 8:
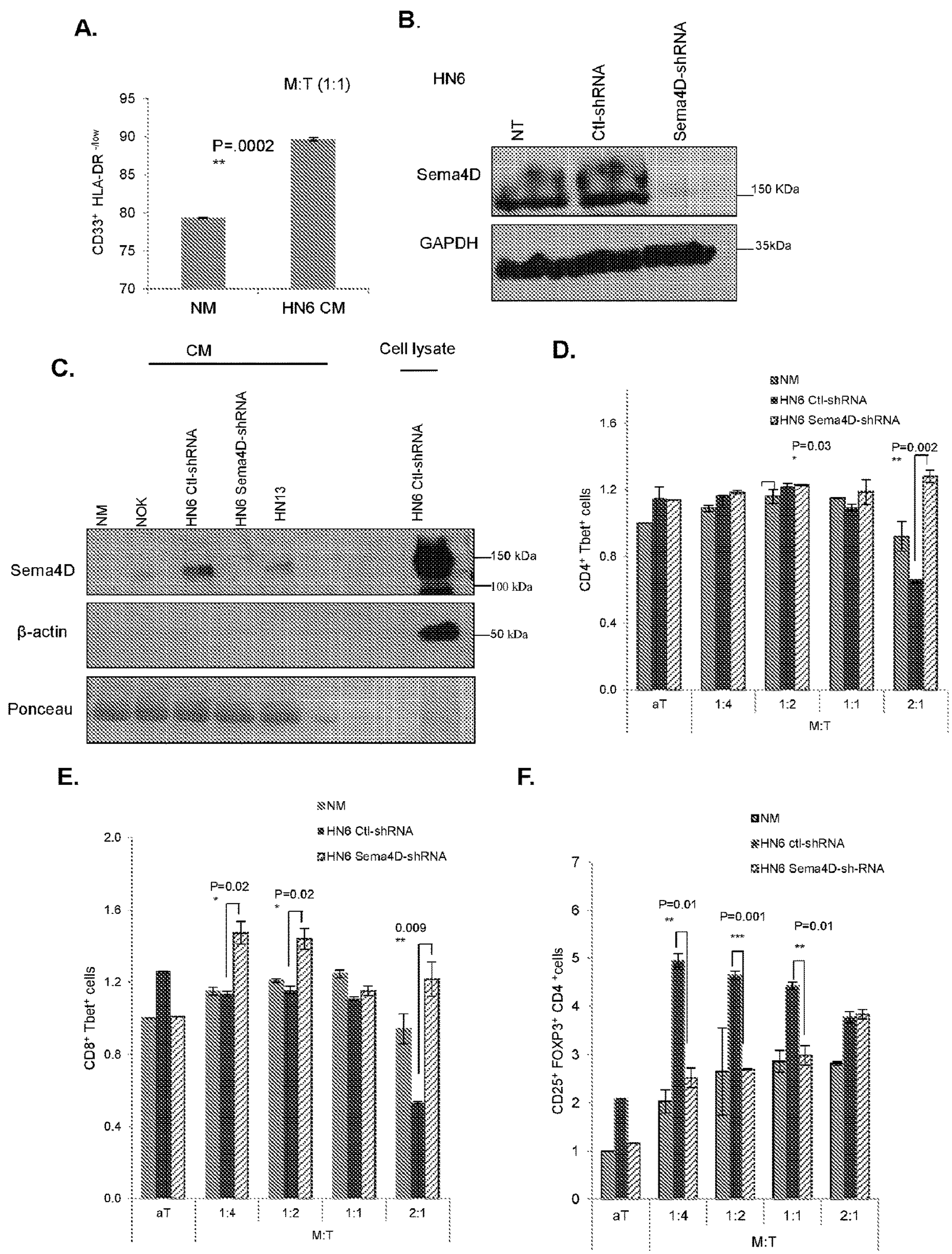
FIG. 8. HN6 produced Sema4D induces MDSC and suppressive T cells in myeloid and T cell co-culture. (A) HN6 CM induces $CD3^+$ $CD11b^+$ HLA-$DR^{-/low}$ upon co-culture of total $CD33^+$ cells with T cells. (B) Inhibition of Sema4D production in HN6 using lentivirus Sema4D-shRNA (cell lysates). (C) and in the supernatant CM. (D) Graphical presentation of accumulative data of frequency for $CD3^+$ $CD4^+$ $Tbet^+$ (E) $CD3^+$ $CD8^+$ $Tbet^+$ effector cells and (F) $CD4^+$ $CD25^+$ $FOXP3^+$ Tregs in HN6 CM of Sema4D-shRNA versus Ctl-shRNA. For D, E, and F, T cells at $2.5\times10^5$ cell density were co-cultured with myeloid cells at the indicated M:T ratios, followed by CD3/CD28 activation. Cells were collected for flow cytometry analysis after 72 hrs. CD3 positive cells were gated for $CD4^+$ $Tbet^+$ and $CD8^+$ $Tbet^+$, then CD3+ were gated for $CD4^+$ then for a CD25$^+$FOXP3$^+$. Samples were run in duplicates. Graphical presentation is normalized to activated T cells growing alone in NM.

We next sought to ascertain whether HNSCC-derived Sema4D mediated its suppressive effects when myeloid cells were cultured with primary T cells. The induction of HLA-$DR^{-/low}$ cells by HN6 conditioned media was still observed upon co-culture of the $CD33^+$ cells with autologous T cells (FIG. 8A). To determine if Sema4D induction of MDSC induces T cell suppression, we constructed Sema4D-shRNA to knock down Sema4D in HN6 cells and accordingly in the conditioned medium (FIG. 8B-C). Significant recovery of T cell proliferation was observed upon co-culture of myeloid and T cells, in the HN6 Sema4D-shRNA compared to the Ctl-shRNA medium (FIG. 3A, 3B). T cells grown in HN6 Ctl-shRNA medium were suppressed upon co-culture with the myeloid cells, but not when cultured in NM, indicating that the suppression is mediated by the induction of MDSC (FIG. 3B). Notably, the knock down of Sema4D produced by HN6, resulted in significant recovery of the T cells at different M:T cell ratios (FIG. 3A, 3B). This was paralleled with recovery of IFN-γ production (FIG. 3C) as well as inhibition of IL-4 in the supernatant (FIG. 3D).

HN6 Secreted Sema4D Induces an Immunosuppressive T Cell Phenotype

To investigate which T cell subset is rescued following blockade of Sema4D, a phenotypic analysis of the T cells was performed. We found that inhibition of Sema4D restored effector Th1 cells ($CD4^+Tbet^+$) and cytotoxic T cells ($CD8^+Tbet^+$) cells, and significantly decreased Tregs ($CD4^+CD25^+FoxP3^+$) at different myeloid to T cell ratios (FIGS. 4A-4D) (FIGS. 8D-F). These findings indicate that inhibition of Sema4D can rescue effector T cells, while suppressing the Treg population in the presence of myeloid cells.

Sema4D Enhances GM-CSF-IL-6 Mediated Induction of MDSC

Figure 5:
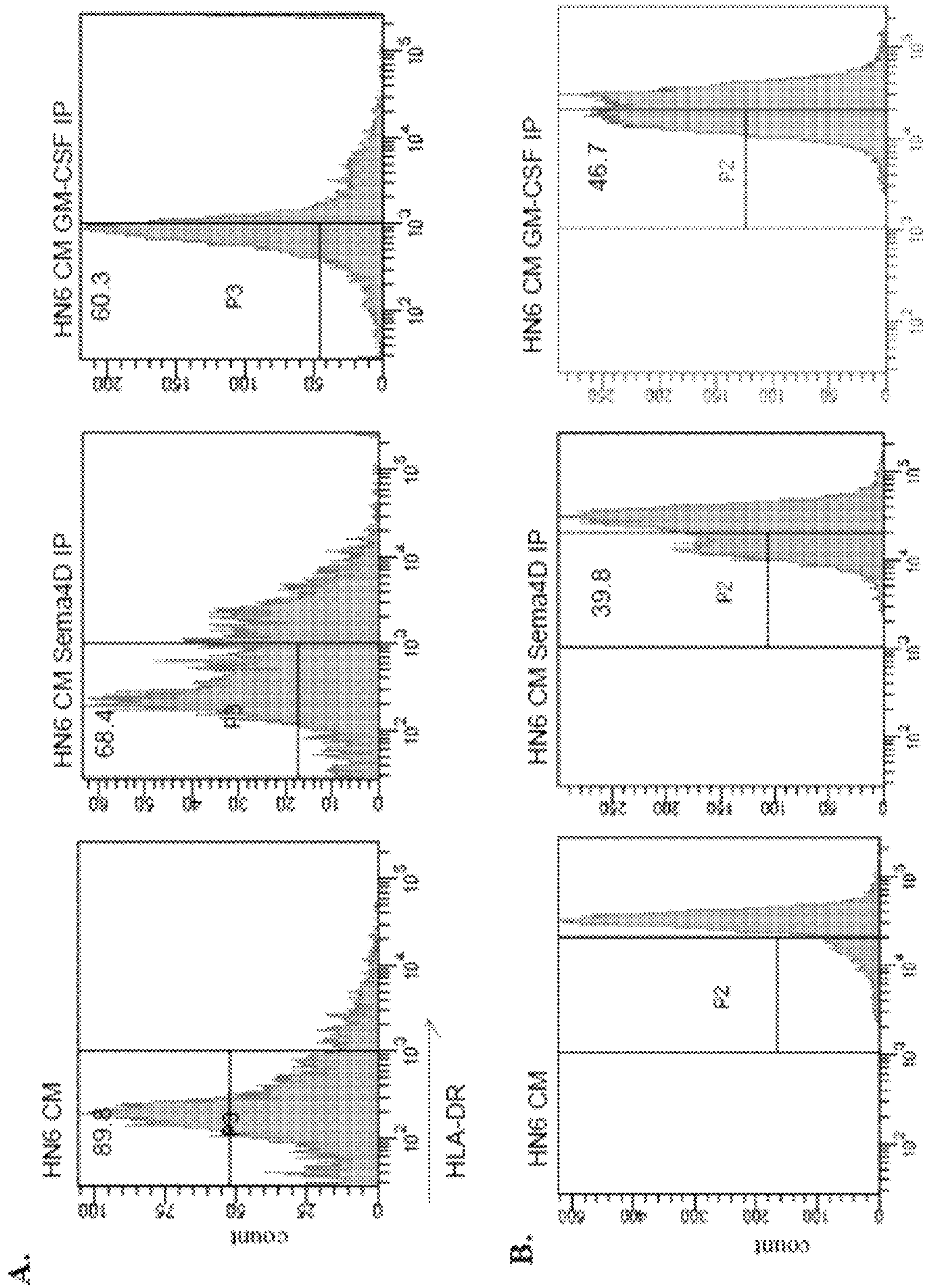
FIG. 5. Sema4D enhances GM-CSF+IL-6 mediated induction of MDSC. (A) The percentage of $CD33^+$ HLA-$DR^{-/low}$ MDSC induced by culture in HN6 CM is reduced following Sema4D or GM-CSF immune precipitation (IP) HN6 CM. (B) Graph shows comparable decrease in the $CD33^+$ HLA-$DR^{-/low}$ population following immune depletion of Sema4D or GM-CSF, compared to the control HN6 CM. (C) HN6 CM was depleted of Sema4D or GM-CSF by immune precipitation (IP), then used to culture myeloid cells and T cells, followed by anti-CD3/CD28 stimulation. After 72 hrs, the cells were analysed by flow cytometry analysis, and the supernatants were collected for ELISA. CFSE dilution in T cells was analyzed by flow cytometry. (D) Graph shows comparable recovery of T cell proliferation upon immune depletion of Sema4D or GM-CSF in HN6 CM. (E) IFN-γ production following immune depletion of Sema4D is comparable to GM-CSF depleted CM. (F) Sema4D is synergistic to GM-CSF+IL-6 in MDSC induction. $CD33^+$ cells separated from PBMC of normal donors were cultured in NM with the recombinant protein GM-CSF alone, or GM-CSF+ IL-6 or the cytokine induction mixture of GM-CSF+IL-6+Sema4D. (G) $CD33^+$ HLA-$DR^{-/low}$ induction in response to treatment with Sema4D, IL-6, GM-CSF alone or combination. (F, G) Each of the recombinant proteins was used at a concentration of 10 ng/ml.
Figure 5:
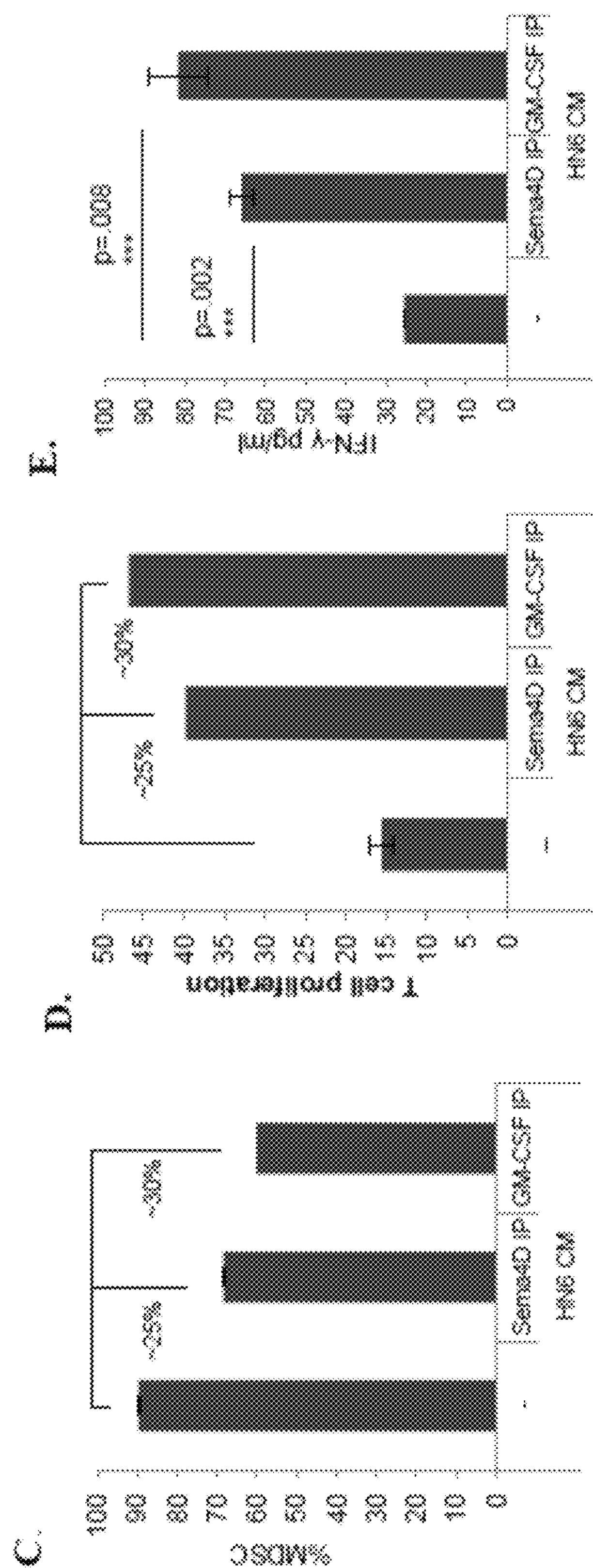

In order to better assess the role of HNSCC-derived Sema4D on myeloid differentiation, we compared Sema4D with another well-described MDSC inducer, GM-CSF (Lechner et al. 2010. *J Immunol* 185: 2273-2284). GM-CSF has been shown to be produced by several MDSC inducing human solid tumors including HNSCC and to best induce human $CD33^+$ suppressive cells upon combination with IL-6 (Lechner et al. 2010. *J Immunol* 185: 2273-2284; Condamine et al., 2011. *Trends Immunol* 32: 19-25; Pak et al., 1995. *Clin Cancer Res* 1: 95-103; Young et al., 1997. *Int J Cancer* 74: 69-74). In fact, we tested the HN6 HNSCC cell line using ELISA and it showed to produce both GM-CSF and IL-6 (data not shown). To compare the effect of tumor secreted Sema4D on the induction of MDSC to GM-CSF-mediated induction, $CD33^+$ cells were co-cultured with T cells in HN6 medium with immune depletion of Sema4D versus immune depletion of GM-CSF. Immune depletion of Sema4D resulted in a significant reduction in the MDSC population that was comparable to that observed upon depletion of GM-CSF in HN6 conditioned medium (FIG. 5A, 5B). The reduction in MDSC cells corresponded with a significant increase in T cell proliferation (FIGS. 5C, 5D) and IFN-γ production (FIG. 5E). These data strongly support a role for Sema4D produced by HN6 cells in the induction of MDSC and its subsequent T cell suppression. To further study the role of Sema4D in conjunction with other tumor produced cytokines in MDSC induction, we grew $CD33^+$ cells in NM to which the three recombinant proteins Sema4D, IL-6 and GM-CSF were added. The three cytokines induction mixture of Sema4D+ GM-CSF+ IL-6 resulted in 30% increase in MDSC induction compared to the GM-CSF+ IL-6 mixture. This indicated that Sema4D acts synergistically with GM-CSF+IL-6 to increase the repertoire of the MDSC cells in the HNSCC tumor microenvironment (FIG. 5F, 5G)

Sema4D Promotes the Production of Immunosuppressive Mediators by MDSC

Figure 6:
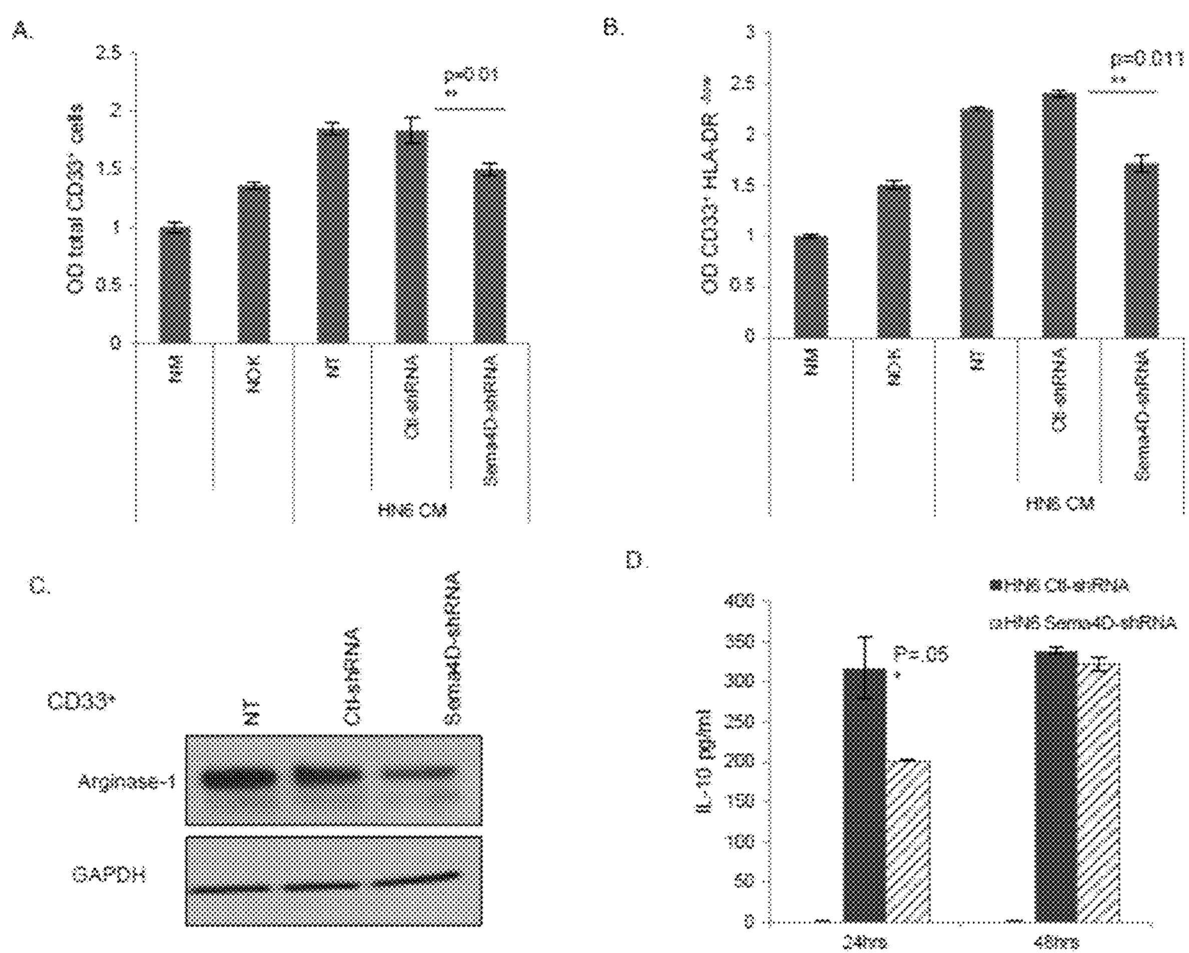
FIG. 6. HN6 secreted Sema4D induces production of immune-suppressive mediators by MDSC. (A) Sema4D promotes proliferation of total myeloid cells. Bulk $CD33^+$ cells cultured in HN6 control or Sema4D-shRNA CM for 24 hrs were analyzed using the WST-1 proliferation assay. (B) Sema4D promotes proliferation of $CD33^+$ HLA-$DR^{-/low}$ cells. $CD33^+$ HLA-$DR^{-/low}$ cells were sorted using magnetic beads and analyzed by WST-1 proliferation assay. All readings were normalized to cells growing in NM. NT; non-transfected. (C) Reconstitution of HN6 Sema4D-shRNA CM with human recombinant Sema4D rescues $CD33^+$ HLA-$DR^{-/low}$ MDSC proliferation. $CD33^+$ HLA-$DR^{-/low}$ labeled with CF SE were analyzed by FACS. (D) Sema4D inhibition in HN6 decreases arginase-1 expression in myeloid cells. $CD33^+$ cells were cultured in NT, Ctl-shRNA or Sema4D-shRNA HN6 CM for 24 hrs, and then analyzed by Western blot for arginase-1 expression. GAPDH served as a loading control. Densitometric analysis included for Western blot data were determined using Image J. (E) Sema4D inhibition in HN6 decreases NO production by myeloid cells. HN6 Sema4D-shRNA CM inhibits nitrite production by myeloid cells. Total $CD33^+$ cells were cultured in CM from HN6 Ctl-shRNA or HN6 Sema4D-shRNA for 72 hrs, then the media was collected to detect the nitrite concentration using Griess reagent. (F) $CD33^+$ cells were cultured in HN6 Sema4D-shRNA or Ctl-shRNA CM and cytokine production was assessed by ELISA. Knockdown of Sema4D results in a decrease in IL-10 production by $CD33^+$ cells. (G) A reduction in Sema4D results in a concomitant decrease in TGF-β production by $CD33^+$ cells. Data are shown with background levels of cytokine subtracted to demonstrate myeloid cell-specific cytokine production.
Figure 6:
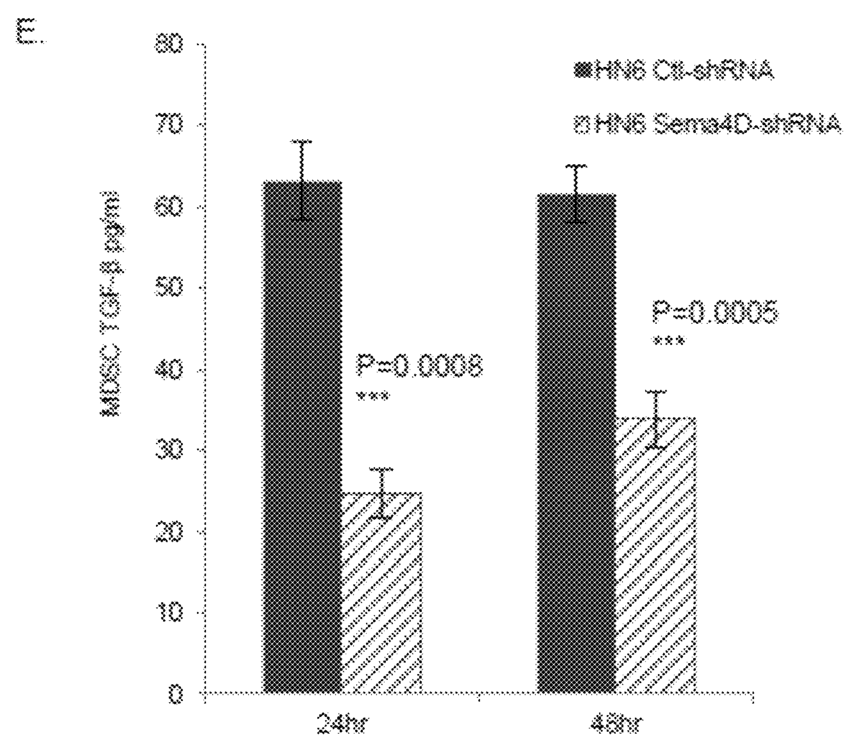

To investigate whether HNSCC associated-Sema4D has an effect on MDSC viability, a WST cell proliferation assay and a CFSE proliferation tracking experiment, were performed using $CD33^+$ cells grown in conditioned medium from the HN6 cells in which Sema4D has been knocked down using shRNA. The loss of Sema4D resulted in a significant decrease in the proliferation of total $CD33^+$ cells, as well as that of the $CD33^+$ HLA-$DR^{-/low}$ population compared to conditioned medium from controls (FIGS. 6A, 6B). Interestingly, reconstitution of the Sema4D-shRNA HN6 conditioned media with human recombinant Sema4D protein recovered the $CD33^+$ HLA-$DR^{-/low}$ proliferation as seen upon CFSE analysis (FIG. 6C). Taken together these findings showed that Sema4D produced by HNSCC plays a significant role in the proliferation and viability of MDSC.

The myeloid cells mediate their suppressive effects by various mechanisms. Among these arginase-1 and nitric oxide (NO) play a major role in MDSC suppressive effect. To investigate whether Sema4D produced by HNSCC-HN6 can affect arginase-1 production, $CD33^+$ enriched myeloid cells were grown in conditioned media from Sema4D-shRNA HN6, and then checked for arginase-1 expression. A significant reduction in arginase-1 production by the $CD33^+$ cells was observed when grown in Sema4D-shRNA HN6 conditioned media (FIG. 6D). While to check for the effect of Sema4D knock down on NO production by myeloid cells, $CD33^+$ cells were grown in HN6 Sema4D-shRNA versus Ctl-shRNA conditioned media, then the media was collected after 72 hrs to check for nitrite concentration. Interestingly there was a significant reduction in nitrite concentration produced by the myeloid cells in the media upon Sema4D knock down in HN6 (FIG. 6E).

MDSC can also indirectly induce its suppressive effect, through production of other immune suppressive cytokines like IL-10 and expansion of Tregs in a TGF-β dependent pathway (Vuk-Pavlovic et al., 2010. *Prostate* 70: 443-455; Capparuccia et al., 2009. *J Cell Sci* 122: 1723-1736). These cytokines were assessed by ELISA, specifically to measure IL-10 and TGF-β produced by MDSC (Cuenca et al., 2011. *Mol Med* 17: 281-292). Interestingly, there was a significant reduction in both IL-10 and TGF-β production by $CD33^+$ cells upon inhibition of Sema4D in HN6 (FIGS. 6F, 6G).

Material and Methods

Cell Lines and Tissue Culture

Human normal oral keratinocytes (NOK), human derived HNSCC cell lines WSU-HN6, and WSU-HN13 underwent DNA authentication (Johns Hopkins genetic resources core facility, Baltimore, Md.) to ensure consistency in cell identity in comparison with their source (Martin et al. 2014. *Oncotarget* 5: 8906-8923). SCC-9 was obtained from American Type Culture Collection (ATCC) (Manassas, Va.). The WSU-HN4 cell line was a generous gift from Dr. Silvio Gutkind (NIDCR, Bethesda, Md.). All HNSCC cell lines used were derived from primary carcinomas of the Tongue. All cell lines were grown and maintained in DMEM supplemented with 10% FBS, 100 units/ml penicillin, 100 µg/ml streptomycin, and 250 ng/ml amphotericin B (Sigma, St. Louis, Mo.) at 37° C. in humidified air with 5% $CO_2$. For treatment with conditioned medium, culture medium was collected from confluent HNSCC cells grown in 5 ml DMEM for 24 hrs. For myeloid and T cell co-culture experiments, conditioned medium supplemented with 5% FBS was used.

Separation of Myeloid and T Cells from Human Peripheral Blood

Mononuclear cell suspension was prepared from peripheral blood of healthy donors obtained from commercial vendors, Biological Speciality Corp (Colmar, Pa.) or New York Blood Center (New York, N.Y.) using Ficoll-Paque Plus density-gradient centrifugation (GE Healthcare Life Sciences, Pittsburgh, Pa.). $CD33^+$ myeloid cells were separated from the PBMC using Magnetic Cell Sorting (MACS) CD33 microbeads (Cat #130-045-501), HLA-DR positive cells were separated using anti-HLA-DR microbeads (Cat #130-046-100) (Miltenyi Biotec Inc, Auburn, Calif.). Autologous T cells were enriched by negative selection with the Human Pan T cell isolation kit (Cat #19051, STEMCELL Technologies Inc., Vancouver, BC, Canada).

Flow Cytometry Characterization of MDSC and T Cells

MDSC were characterized using multicolor staining fluorochrome-labeled anti-human CD33-PerCP/Cy5.5 (Cat #303414), HLA-DR-APC (Cat #307610), CD11b-PE (Cat #301306), CD14-FITC (Cat #325604) (Biolegend, San Diego, Calif.). For T cell analysis CD3-APC/Cy7 (Cat #300317) (Biolegend), CD8a PE-Cy7 (cat #25-0088-42), CD25-APC (Cat #17-0259-42), Foxp3-PE (Cat #12-4776-42), T-bet PerCP-Cyanine5.5 (Cat #45-5825-82) (eBioscience, Inc., San Diego, Calif.). For anti-FoxP3-PE and anti-Tbet-PerCP/Cy5.5, fixation and permeabilization buffer (Cat #00-8333) eBiosciences was used. For T cell proliferation, T cells were stained with CF SE (Cat #C34554) (Life Technologies, Grand Island, N.Y.), prior to plating. Dynabeads human T-activator CD3/CD28 (Life Technologies) were used at a 1:3 (T cell: bead) ratio after coculture with myeloid cells for at least 4 hrs. Data was acquired using a BD LSR II Flow cytometer, FlowJo software (Tree Star, Ashland, Oreg.) and analyzed using BD FACSDiva™ software (BD Biosciences, San Jose, Calif.).

Immunoblot, Antibodies and Reagents

Cells were harvested in cell lysis buffer (20 mM Tris-HCL (pH7.5), 150 mM NaCl, 1 mM $Na_2EDTA$, 1 mM EGTA, 1% Triton, 2.5 mM sodium pyrophosphate, 1 mM β-glycerophosphate, 1 mM $Na_3VO_4$, 1 ug/ml leupeptin) (Cat #9803) (Cell Signaling Tech., Danvers, Mass.) with the addition of 1× protease inhibitor Complete Mini, EDTA-Free (cat #11836170001) (Roche Diagnostics Corporation, Indianapolis, Ind.). Whole-cell lysate was separated using SDS-PAGE. The primary antibodies Sema4D (30/CD100, Cat #610670) (BD Biosciences PharMingen, San Diego, Calif.), Arginase-1 (A-2: sc-365547), GAPDH (8C2: sc-81545), and β-actin (Cat #sc-2301), (Santa Cruz Biotechnology, Inc., Dallas, Tex.), were used. The secondary antibodies used were anti-rabbit IgG (Cat #sc-2301) and anti-mouse IgG (Cat #sc-2302) (Santa Cruz Biotechnology, Inc.). For Arginase-1 detection 15 µg of protein were loaded, while for Sema4D detection 70-100 µg were loaded. For detection of Sema4D in the tumor conditioned medium, equal aliquots of the medium or of a concentrate of the medium using Millipore amicon Ultra centrifugal filter units were loaded after adding the sample buffer. Cell viability was measured using the cell proliferation reagent, WST-1 (Roche Diagnostics Corporation). The plate was read at 450 nm on BioTek Epoch microplate spectrophotometer (BioTek, Winooski, Vt.). The recombinant human Sema4D (sCD100) (Cat #310-29) was obtained from (Peprotech, Rocky Hill, N.J.). Recombinant human GM-CSF (Cat #215-GM-010) (R&D Systems, Inc. Minneapolis, Minn.), and Il-6 recombinant human (Cat #11395) from (Sigma-Aldrich, St. Louis, Mo.) were also used. Griess reagent (Cat #G2930) (Promega corporation, Madison, Wis.) was used to measure the Nitrite ($NO_2$—) concentration as a stable nonvolatile byproduct of nitric oxide (NO) in the media, read at absorbance of 520 nm using BioTek Epoch microplate spectrophotometer (BioTek).

Anti-Sema4D Treatment and Immune Depletion

For target protein inhibition in the conditioned medium anti-Sema4D (Cat #610670) (BD Biosciences) was used at concentration (10 µg/ml). For immune-depletion, immunoprecipitation of Sema4D or GM-CSF, was carried out by overnight incubation of the conditioned media with Sema4D (Cat #ab39710) (Abcam, Cambridge, Mass.) or GM-CSF (clone: BVD2-21C11) (Cat #502301) (Biolegend) (10 µg/ml) mAbs using protein A beads, followed by precipitation.

Sema4D shRNA and Lentivirus Infections

The lentivirus and short-hairpin RNA (shRNA) system were a kind gift of Dr. John R. Basile, UMB (Basile et al. 2006. *Proc Natl Acad Sci USA* 103: 9017-9022). In brief, the shRNA sequences for human Sema4D were obtained from Cold Spring Harbor Laboratory's RNAi library (RNAi Codex; http:katandin.csh1.org: 9331_homepage_portal_scripts_main2.pl). The oligonucleotides (Invitrogen, Grand Island, N.Y.) used to knockdown Sema4D protein levels were: 5-GGCCTGAGGACCTTGCAGAAGA-3 (SEQ ID NO:3). The Sema4D shRNA oligonucleotides were cloned into lentiviral expression vector pWPI GW as previously described (Basile et al. 2006. *Proc Natl Acad Sci USA* 103: 9017-9022). pWPI (empty) vector was used as negative control. Infections were performed using Fugene HD transfection reagent (Cat #E2311, Promega, Madison, Wis.).

ELISA

Human ELISA MAX™ IFN-γ (Cat #430103), TGF-β1 total (Cat #436707), IL-10 (Cat #430601), and IL-4 (Cat #430301) were obtained from Biolegend. Samples were run in triplicates and read using BioTek Epoch microplate spectrophotometer at 450 nm wavelength.

Statistics

Student's paired t tests were performed as appropriate. All data analysis was presented with custom STDEV and p values were annotated as: *p≤0.05; p≤0.01; *p≤0.001.

Example 2

Diagnostic Assays for Sema4D

Herein, it is presented for the first time a rapid and sensitive diagnostic test for head and neck cancer patients, as well as patients with hematologic malignancies using ELISA and IHC to measure Sema4D. The proposed ELISA test can be performed on patient's sera for diagnostic measures, and the IHC on head and neck cancer tissue can indicate the status of the tumor progression.

Material and Methods

ELISA

ELISA performed using specimens from HNSCC patients, lymphoma patients and healthy donor serum. For the standard, human recombinant Semaphorin 4D (Cat #310-29) (PEPROTECH, Rocky Hill, N.J.) was used. Semaphorin 4D (clone eBio133-1C6) (Cat #14-1009) (eBioscience, San Diego, Calif.) was used as the primary detection antibody. The secondary antibody, goat anti-mouse anti-IgM HRP (Caltag Cat #M31507) was applied followed by detection with tetramethybenzidine (TMB) substrate.

ELISA Protocol:

1. Assay Diluent (AD) is 5% FBS in PBS; Plates-Immunlon (Nunc #14-245-153)
2. Coat with protein, dilute standard in PBS (200 ng/ml) and add 50 ul/well (4 C overnight)
3. Block with AD-100 ul/well 2 hr RT
4. Wash w PBST (0.05% Tween20 in 1×PBS)
5. Primary Ab (eBioscience 10 ul/ml from 0.5 mg/ml stock) in AD; incubate 2 hr RT; wash
6. Add 2nd Ab (goat anti mouse IgM HRP; stock lmg/m1) 1:1000 dilution in AD for 1 hr RT
7. Wash, Detect w TMB, stop with 2N sulfuric acid Immunohistochemistry Immunohistochemistry was carried out on paraffin embedded tissue microarray including 124 primary HNSCC, 9 primary adenocarcinomas of the salivary glands, 3 metastatic HNSCC, 4 metastatic adenocarcinomas of the salivary glands to lymph nodes, 12 normal oral mucosa, 3 normal salivary glands and 4 normal epiglottis tissue. The microarray was obtained from US Biomax, Inc. (Rockville, Md.). Citrate buffer (Cat #21545, Millipore, Billerica, Mass.) and EDTA free trypsin (Corning, Manassas, Va.) (Cat #25-050-CI) were used for antigen retrieval. 3% $H_2 0_2$ was used to quench the endogenous peroxidase. Tissue was incubated in the primary antibody Semaphorin 4D (clone 30/CD100) (Cat #610670) (BD Biosciences PharMingen, San Diego, Calif.) at 1:50 dilution in 2% BSA in PBS with 0.1% Tween, overnight in 4 degrees C. The Secondary antibody and the ABC (Vectastain Vector Elite Cat #PK-6102 mouse IgG) (Vector laboratories, Burlingame, Calif.) were used, followed by DAB (Cat #SK-4105) (Vector laboratories). Tissue was scanned and photomics were taken using ScanScope Aperio software.

Results

Sema4D is a Diagnostic Marker in Peripheral Blood of Cancer Patients

Figure 9:
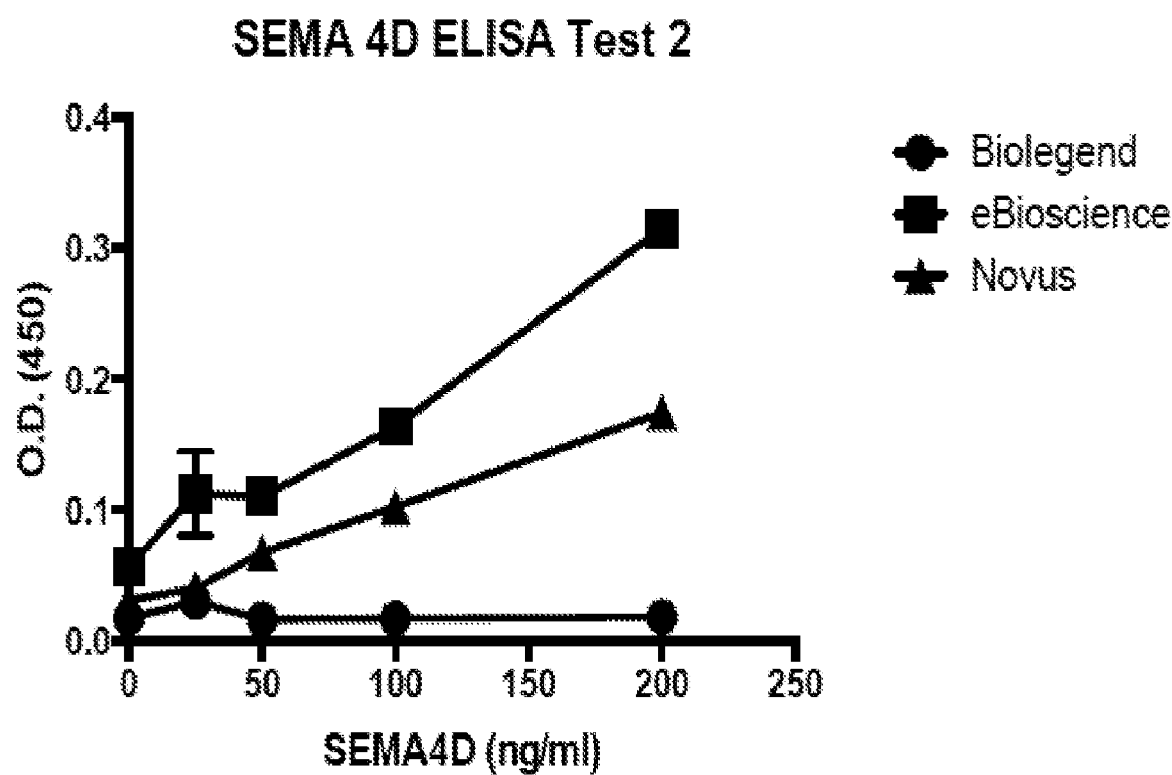
FIG. 9. Characterization of commercially available Sema4D Abs for ELISA. An indirect ELISA was performed in which plates were coated with serial dilutions of Sema4D recombinant protein (Peprotech), then incubated with the indicated Abs to determine which Abs could be used for ELISA. BD—mouse anti-Human (IgGi), eBioscience—mouse anti-Human (IgM), Novus—Ab is biotinylated, avidin peroxidase was used.
Figure 10:
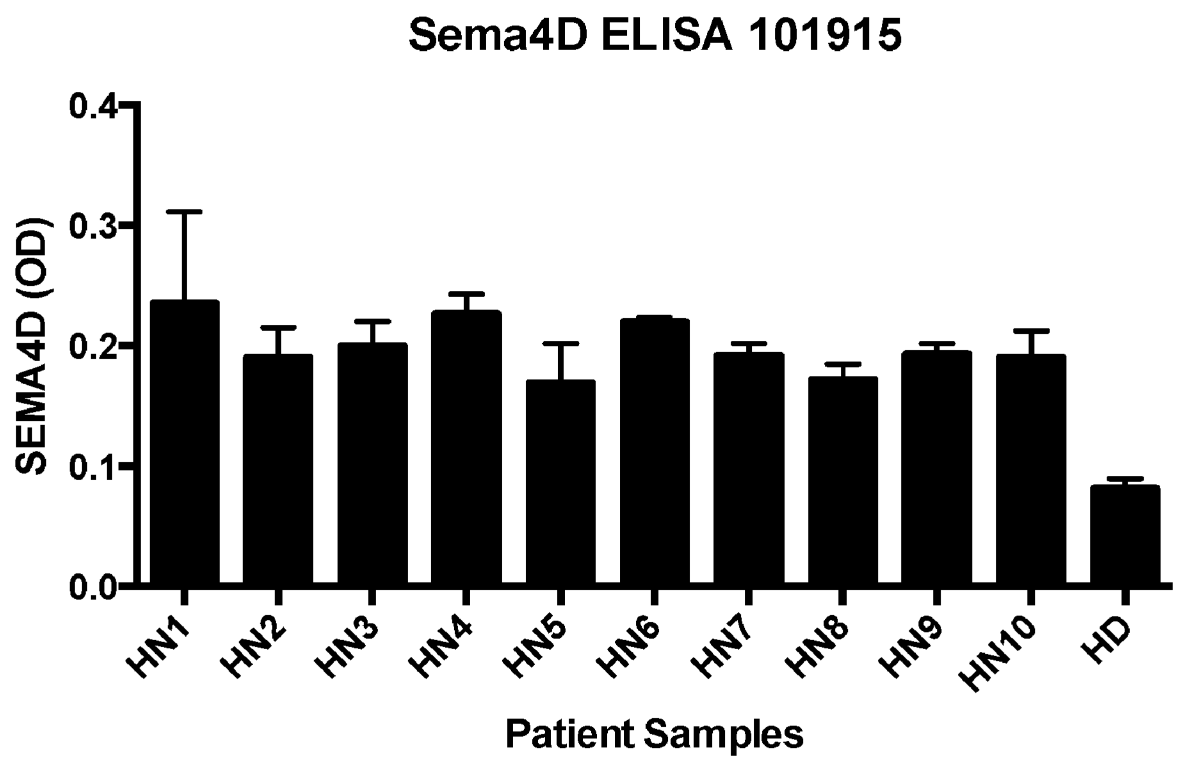
FIG. 10. Sema4D levels are higher in patients with head and neck cancer, compared to sera from healthy donors (HD serum purchased from Atlanta Biologicals).
Figure 11:
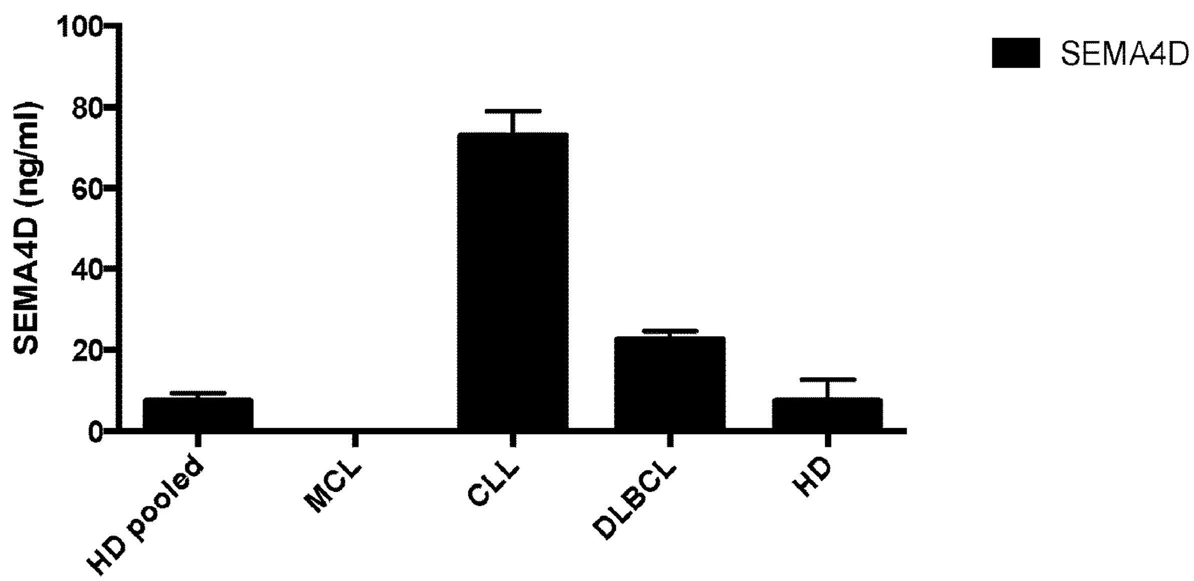
FIG. 11. Sema4D is present in sera from some lymphoma patients.

To investigate if Sema4D is a candidate diagnostic marker for cancer patients in peripheral blood, we carried ELISA on sera from HNSCC patients, lymphoma patients and healthy donors. HNSCC patients showed almost double the expression of Sema4D in their sera compared to healthy donors (p=0.00017). Also high levels of Sema4D were detected in sera of 2 of the lymphoma patients compared to the healthy donors (FIGS. 9-11).

Sema4D Insitu Expression as a Predictive Marker for Disease Progression

To investigate the use of Sema4D as a prognostic marker in HNSCC, we carried out immunohistochemistry on primary HNSCC, primary adenocarcinomas of the salivary gland, metastatic HNSCC and metastatic salivary gland tumors to lymph nodes. Collectively, Stages I and II of the primary HNSCC showed negative to week expression of Sema4D. Stages III and IV showed strong diffuse expression of Sema4D. Metastatic HNSCC and salivary gland metastatic adenocarcinomas to lymph nodes showed strong and diffuse expression. In stages III, and IV HNSCC as well as in the metastatic lesions, increased inflammatory cell infiltrate with strong expression of Sema4D in the tumor stroma was noticed.

The control normal oral epithelium showed week to negative basal and parabasal expression of Sema4D. The normal epiglottis lining showed moderate diffuse expression and the normal salivary gland tissue showed diffuse weak to moderate expression of Sema4D in the acini and ductal structures.

Example 3

Semaphorin 4D in Human Head and Neck Cancer Tissue and Peripheral Blood: A Dense Fibrotic Peri-Tumoral Stromal Phenotype In this study, the immunohistochemical expression of Sema4D by HNC tumor cells in correlation to tumor progression, extent of fibrosis and TAIs infiltration in the peri-tumoral stroma, as well as PD-L1 expression was investigated. It is shown that high levels of Sema4D expression ($Sema4D^{+ve/high}$) by HNC tumor cells significantly correlated with clinical staging, being highest in stage III. It also showed a positive nonsignificant correlation with nodal metastasis. $Sema4D^{+ve/high}$ expression in tumor cells correlated significantly with dense fibrotic noninflamed peri-tumoral stroma and inversely with infiltrating $Sema4D^{+ve/high}$ TAIs. Interestingly, knockdown of Sema4D in stage III HNC cell line, showed inhibition of TGF-β1 production by the tumor cells. Sema4D identified a unique subset of HNC tumors distinct from the PD-L1 positive tumors. Furthermore, high levels of circulating Sema4D were detected in HNC patients' sera compared to healthy donors. These data provide a novel role for Sema4D in the context of fibrosis and inflammation within the tumor microenvironment and demonstrate its value as a novel diagnostic, prognostic and immune monitoring biomarker in HNC.

Results

Sema4D Expression by Tumor Cells Correlates with Tumor Progression

Figure 18:
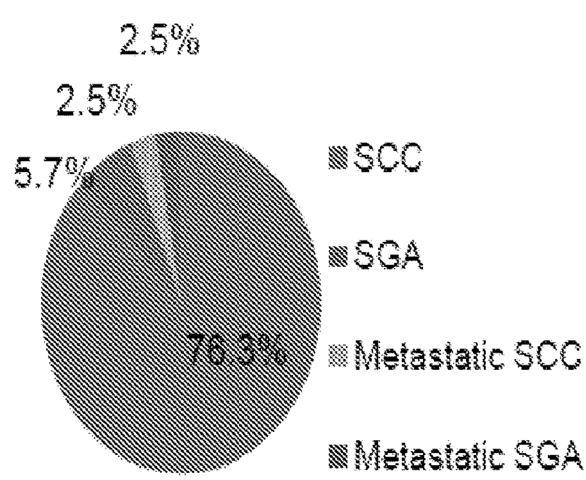
FIG. 18. Graphical presentation of the human HNC tumor samples (A) Pie chart representative of the HNC tumors included in the study. (B) Graphical presentation of the SCC cases included in the study according to tissue of origin. SCC; Squamous cell carcinoma, SGA; Salivary gland adenocarcinoma.
Figure 18:
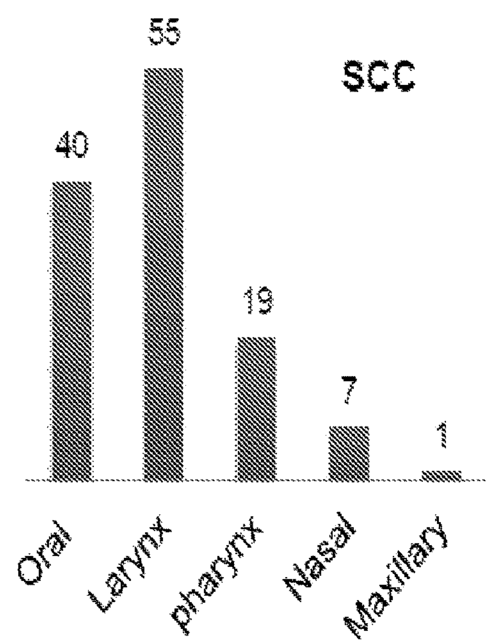

Sema4D expression has been described in several epithelial malignancies, but it is believed that there are no studies investigating whether it correlates with clinical progression in HNC (Ch'ng E et al., *Cancer.* 2007; 110(1):164-172; Wang et al., *World J Gastroenterol.* 2015; 21(7):2191-2198). Immunohistochemical (IHC) analysis was performed on 160 human tissue samples. These included twenty one cases of normal tissue, and one hundred and thirty-nine cases of HNC. The malignancies consisted of 119 primary squamous cell carcinomas of the head and neck (HNSCC), 9 primary salivary gland adenocarcinomas (SGA), 4 metastatic HNSCC and 4 metastatic SGA to the lymph nodes. One normal tongue specimen was excluded due to lack of epithelial tissue and three cases of malignancy were excluded due to lack of tumor tissue for analysis (FIGS. 18A and 12B) (Table 5). The age range for the studied population was from 12 to 90 years old with mean of 53 among which there were 82 (51.25%) females and 78 (48.75%) males. The demographics of the 136 HNC patients in this study are summarized in Table 6.

Figure 19:
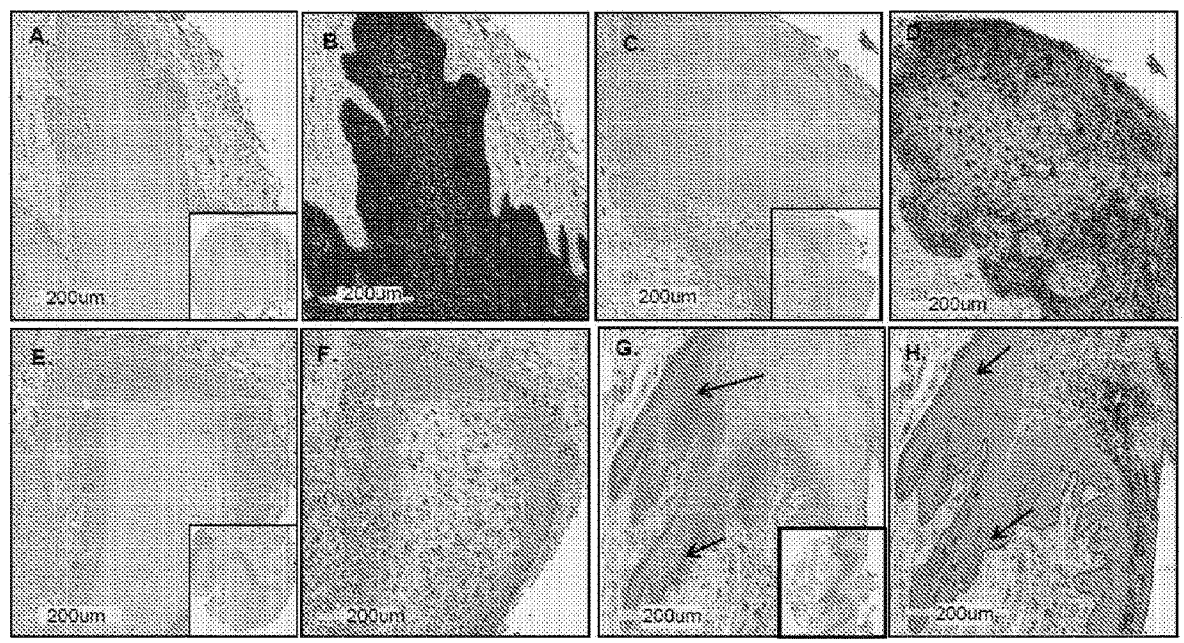
FIG. 19. Sema4D expression in the normal epithelium and epithelial tissue adjacent to tumor margin. (A) Normal parakeratinized stratified squamous epithelium of the tongue is negative for Sema4D expression. (B) Digital analysis of tissue in (A) showing negative Sema4D expression (blue) through the entire thickness with only 6×10$^3$ strong positive pixel intensity. (C) Normal parakeratinized stratified squamous epithelium showing Sema4D$^{-ve/low}$ expression with focal positivity in the prickle cells. (D) Digital analysis of tissue in (C) shows negative (blue) to focal positive (orange) expression of the prickle cell layer with 3.5×10$^4$ of strong positive pixel intensity. (E) Normal tongue epithelium showing focal Sema4D$^{+ve/high}$ expression in the parabasal cell layer. (F) Digital analysis of (E) shows diffuse weak expression (yellow) in the prickle cells, to focal positive (orange) expression in the parabasal layer with 2×10$^5$ mean of strong positive pixel intensity. (G) Sema4D$^{+ve/high}$ in the basal and prickle cell layer of the surface epithelium (arrows). (H) Digital analysis of Sema4D staining in (G) shows high (red) expression in the basal cell layer and diffuse positive expression in the prickle cell layer with 1.3×10$^6$ mean of strong positive pixel intensity. The strong positive pixel intensity presented is the mean of three annotations of each tissue section. (20×; 200 um scale, inset: 40×).
Figure 20:
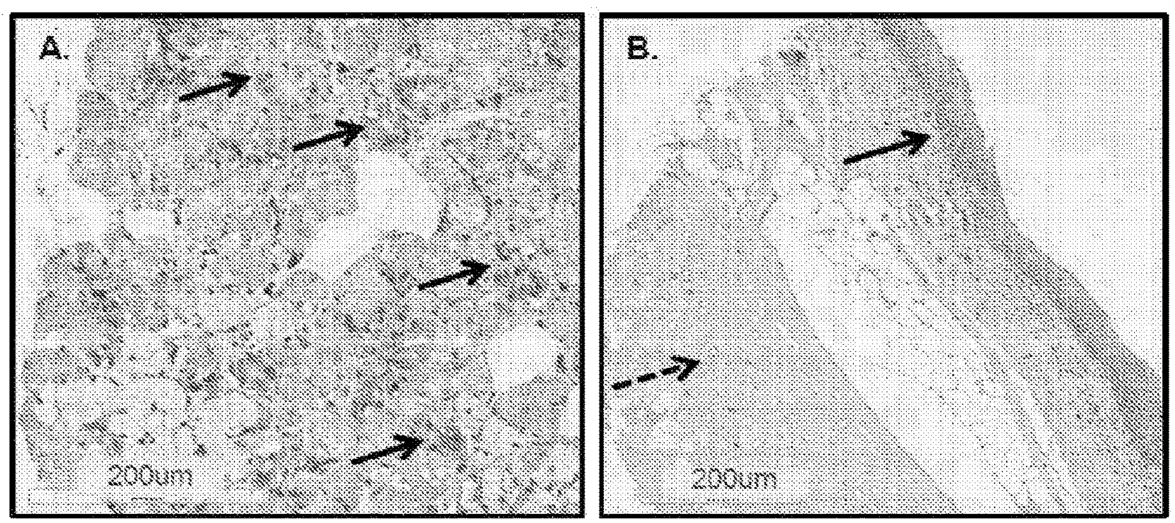
FIG. 20. Sema4D expression in normal salivary glands and epiglottis. (A) Normal salivary gland acini and ducts, shows positive expression in the ductal cells (arrows), mucous and serous acini are negative. (B) Normal epiglottis shows positive Sema4D expression in the lining epithelium (arrow) and focal expression in chondrocytes (dotted arrow) (20×; 200 um scale).

The pattern of expression of Sema4D was generally membranous and cytoplasmic. The normal oral epithelium and salivary acini were negative to low positive (Sema4D$^{-ve/low}$), with mean strong positive pixel intensity ranging from ~$10^4$ to $2\times10^5$ (FIG. 19 A-F), while the salivary ductal epithelium and the normal epiglottis epithelial lining were positive for Sema4D (FIG. 20). The normal tissue adjacent to tumor margin (NAT), was Sema4D positive to strongly positive (Sema4D$^{+ve/high}$) in the basal and prickle cell layer with mean strong positive pixel intensity of up to $10^6$ (FIG. 19 G-H). The scattered inflammatory cells in the normal tissue sections were also positive for Sema4D.

Figure 12:
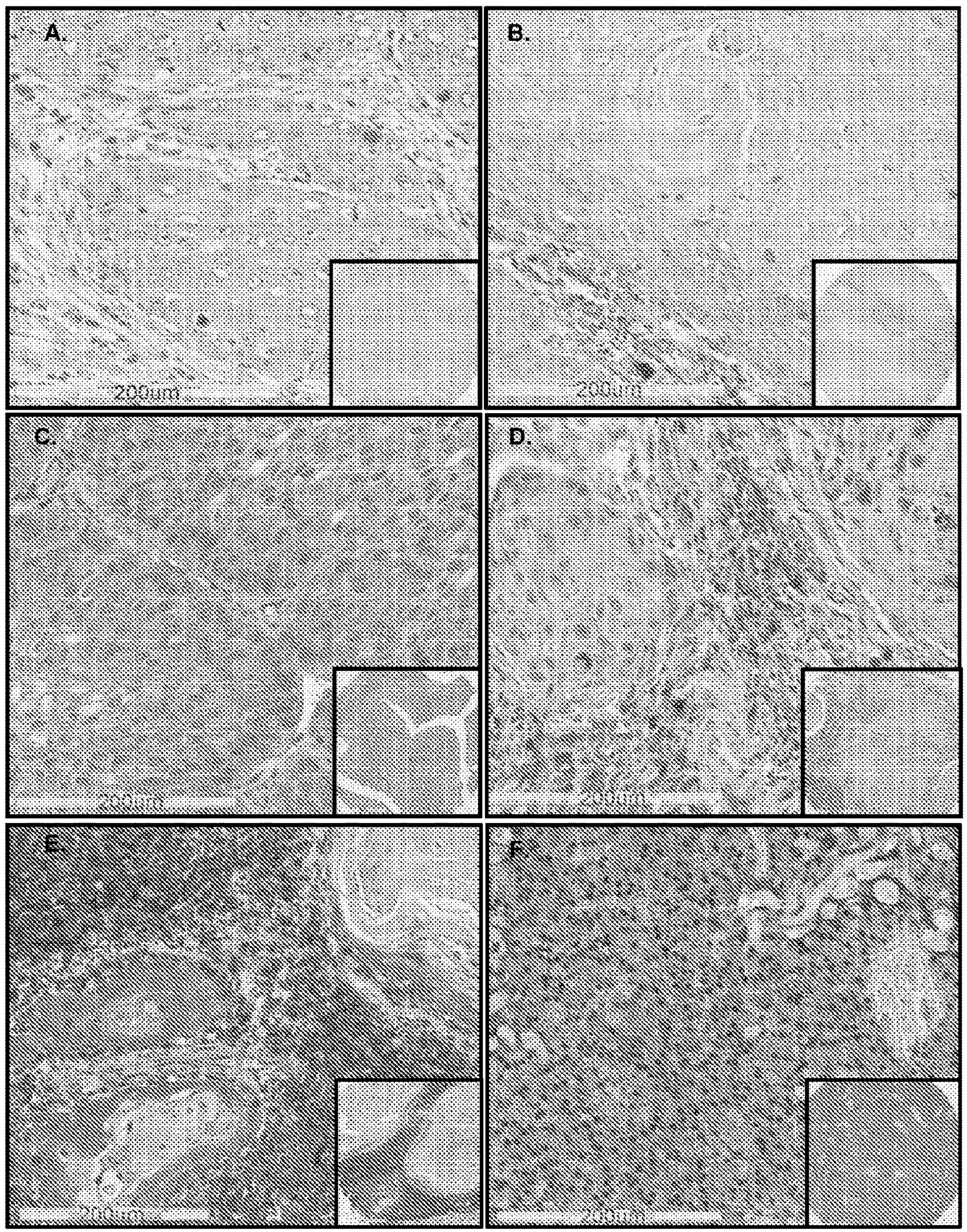
FIG. 12. Sema4D expression in HNC tumor cells in different clinical stages and metastases. (A) IHC shows Sema4D$^{-ve/low}$ expression in tumor cells of a stage I SCC of the nasal cavity. (B) Sema4D$^{-ve/low}$ expression in tumor cells of Stage II SCC of the larynx. Moderate stromal infiltration with Sema4D$^{+ve/low}$ TAIs. (C) Sema4D$^{+ve/high}$ expression in tumor cells of a stage III SCC of the upper Jaw. (D) Sema4D$^{-ve/high}$ expression in tumor cells of stage IV SCC of the gingiva with the peri-tumoral stroma showing heavy infiltration of Sema4D$^{+ve/high}$ TAIs. (E) Metastatic SCC to the lymph nodes. Tumor cells show strong Sema4D$^{+ve/high}$ expression as well as the inflammatory cells of the lymph node. (F) Metastatic acinic cell carcinoma to the lymph nodes, showing Sema4D$^{+ve/high}$ expression. (20×; 200 um scale, inset: 40×).
Figure 21:
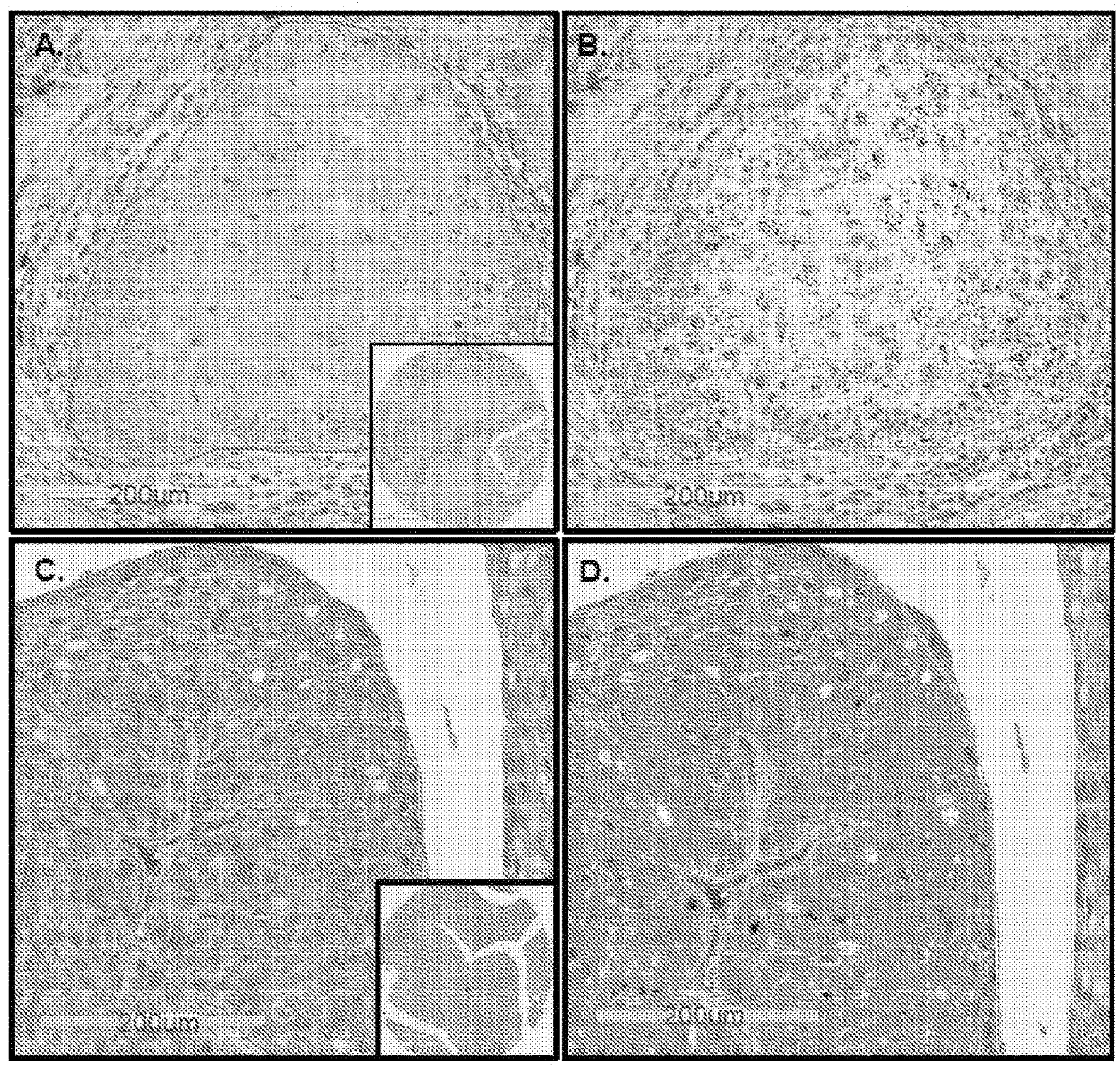
FIG. 21. Standardization of Sema4D expression in tumor islands. (A) Stage I SCC of the lip showing $^{-ve/low}$ expression of Sema4D in the annotated tumor island. (B) Digital analysis of Sema4D staining in (A) showing low expression (yellow), in the tumor cells with low level of strong positive pixel intensity of $1.5\times10^5$. (C) Stage III SCC of the left upper jaw, showing diffuse Sema4D$^{+ve/high}$ expression, with annotation set for digital analysis. (D) Digital analysis of Sema4D expression in (C) showed high level of strong positive pixel intensity of $1.1\times10^6$. The total intensity of strong positive pixels was calculated as the mean of three different annotations representative of the whole tumor, each annotation was analyzed under 200× magnification in an area of ~0.2 mm$^2$ (20×; 200 um scale, inset: 40×).

Sema4D$^{+ve/high}$ expression was observed in in 47 (34.5%) cases out of the 136 primary and metastatic malignancies (Table 5). The cut off value to consider Sema4D$^{+ve/high}$ in tumor cells was $5\times10^5$ strong pixel intensity as guided by the standardized digital analysis (FIG. 21). Sema4D$^{+ve/high}$ expression in tumor cells correlated significantly with stage III HNC (p=0.014), (Table 1). Tumor cells were generally Sema4D$^{-ve/low}$ for expression in stage I and II, Sema4D$^{+ve/high}$ in stage III and Sema4D$^{-ve/low}$ expression in stage IV tumor cells (FIG. 12A-D). A positive association between Sema4D expression in tumor cells and nodal metastasis was observed, specifically patients with nodal metastasis had higher levels of Sema4D staining in the primary tumor (p=0.117) (Table 1). Only one out of four metastatic SCC to lymph nodes had Sema4D$^{+ve/high}$ expression in the tumor cells, while the others were Sema4D$^{-ve/low}$ (FIG. 12E). There was no association detected between the Sema4D expression in tumor cells and the demographic variables of the tested individuals or the histological grade of SCC (Table 6). Out of the limited number of SGA cases studied, Sema4D$^{+ve/high}$ expression was observed in 7 (77%) out of the 9 primary and 3 out of 4 metastatic SGA to lymph nodes (Table 6) (FIG. 12F).

Figure 13:
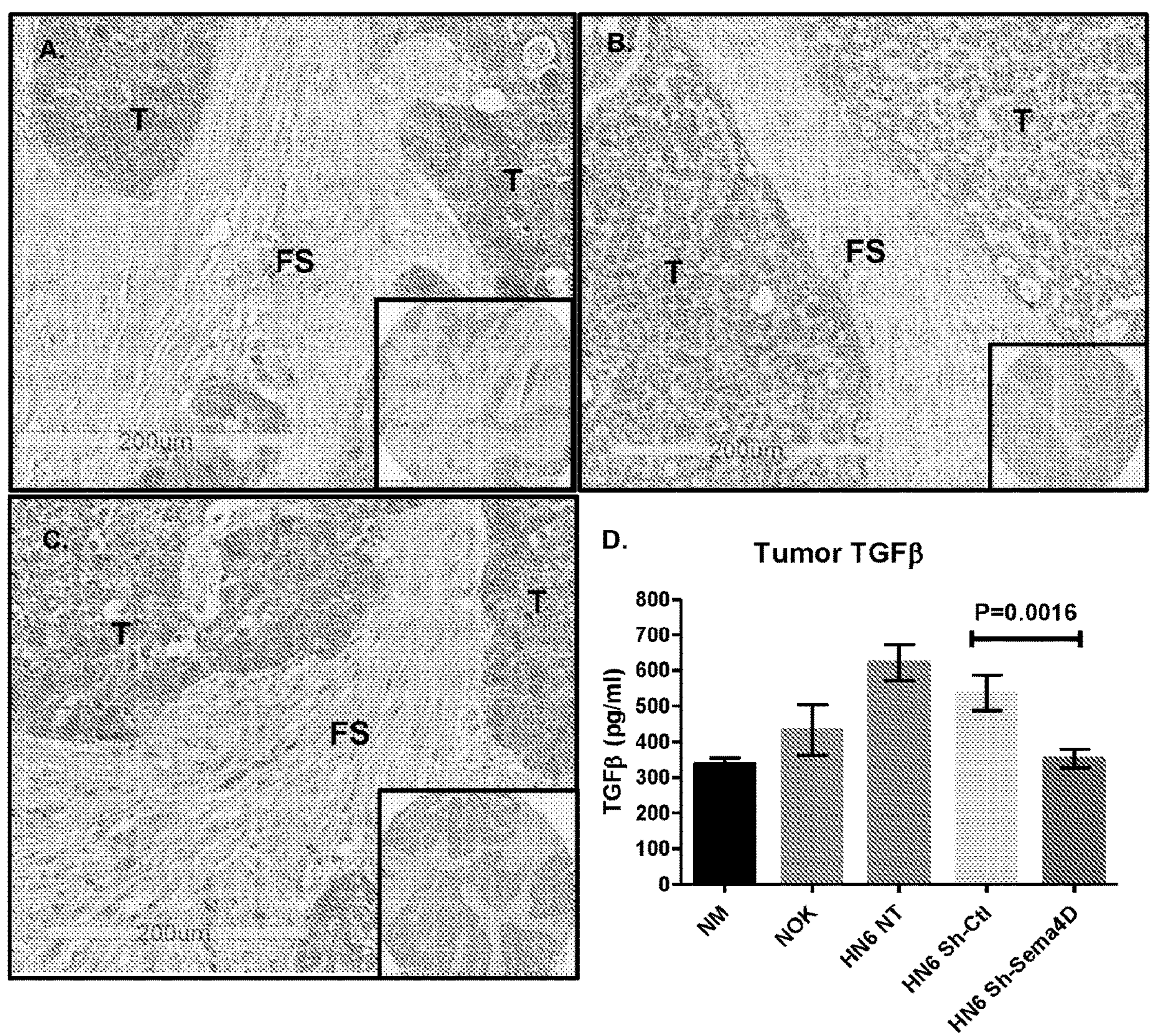
FIG. 13. Sema4D high expression in tumor cells correlates directly with fibrosis and TGF-β1 production. (A) IHC shows Sema4D$^{+ve/high}$ expression in tumor islands with surrounding dense fibrotic stroma in a stage I SCC of the maxillary sinus. (B) Sema4D$^{+ve/high}$ expression in tumor islands of a stage II Adenoid Cystic Carcinoma of minor salivary glands arising in the tongue, associated with dense fibrotic stroma. (C) Sema4D$^{+ve/high}$ expression in stage III SCC of the larynx and surrounding dense fibrotic stroma. (D) Detection of TGF-β1 in CM of stage III HNC cell line. Sema4D knockdown in HN6 cell line using sh-RNA lentivirus shows downregulation of TGF-β1 production in the CM as detected by ELISA, compared to transfection control (Ctl), non-transfected (NT), normal oral keratinocytes (NOK) and Normal media (NM). CM; conditioned medium. T; Tumor, FS; fibrotic stroma, (20×; 200 um scale, inset: 40×).

Sema4D Expression by Tumor Cells Correlates with a Dense Fibrotic Peri-Tumoral Stroma The peri-tumoral-stroma is a very important reflection of the complexity of the tumor (Hanahan D and Weinberg R A. *Cell.* 2011; 144(5):646-674; Pietras K and Ostman A. *Exp Cell Res.* 2010; 316(8):1324-1331). To determine whether Sema4D has a role in modulating the immune response within the tumor microenvironment, we examined the stroma in all of the provided specimens. Sema4D$^{+}$ve/high expression by HNC tumor cells of the primary malignancies correlated with a dense fibrotic peri-tumoral stroma representing 23% of the total cohort (FIG. 13 A-C) (p=0.0001) (Table 1). The data showed 77% of the cases with dense peri-tumoral stroma to be Sema4D$^{+ve/high}$. We previously showed that inhibition of Sema4D in HNC cell lines can downregulate TGF-β1 production by myeloid cells (Younis R H et al. *J Immunol.* 2016; 196(3):1419-1429). These data led us to further investigate whether Sema4D can directly induce HNC cells to produce the potent fibroblast chemoattractant; TGF-β1, and conversely if inhibition of Sema4D would affect the production of TGF-β1 by tumor cells. Sema4D expression was highest in stage III tumors (Table 1), therefore we generated stable Sema4D knockdown and controls using the WSU-HN6 cell line, derived from a stage III SCC of the base of the tongue (Morikawa et al., *Cold Spring Harb Perspect Biol.* 2016; 8(5); Prud'homme et al., *Lab Invest.* 2007; 87(11): 1077-1091; Jeon et al., *Int J Cancer.* 2004; 112(2):249-258).

As shown in FIG. 13D, WSC-HN6 cells produce high levels of TGF-β1 in the culture medium, compared to controls normal oral keratinocytes (NOK). Inhibition of Sema4D in WSC-HN6 cells using shRNA, significantly reduced TGF-β1 production by the tumor cells to levels comparable to NOK and to that present in normal cell culture media (FIG. 13D).

Sema4D Expression by Tumor Associated Inflammatory Cells (TAIs)

Figure 14:
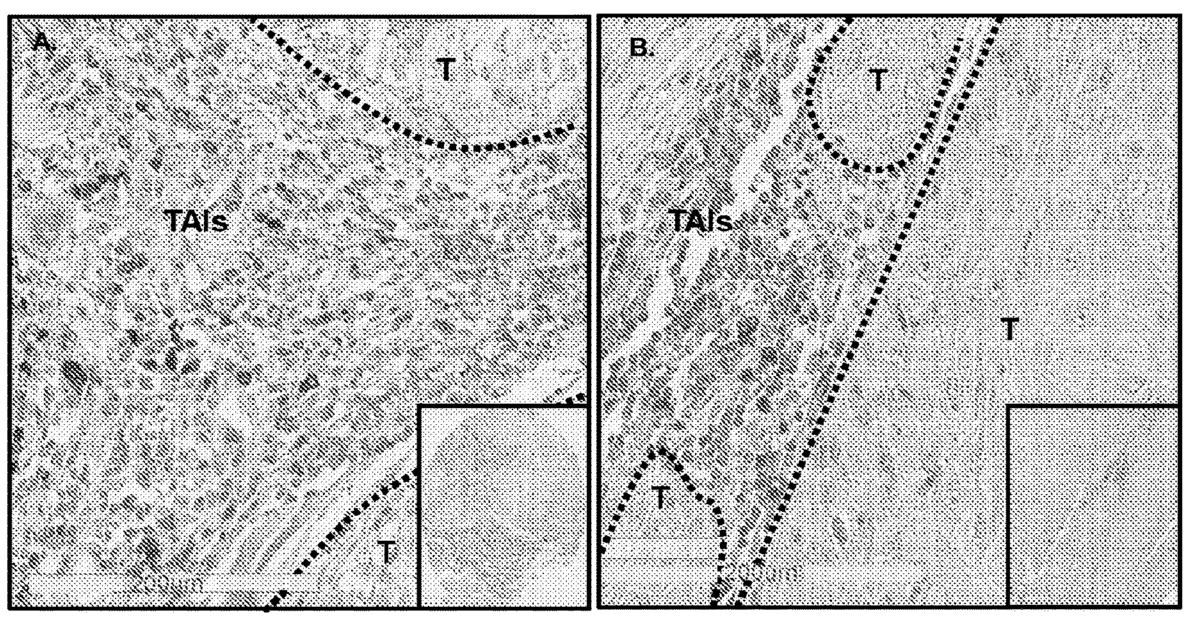
FIG. 14. Sema4D$^{+ve/high}$ expression in stromal infiltrating TAIs correlates inversely with its expression in tumor cells. (A) Sema4D$^{+ve/high}$ expression in TAIs corresponded to negative Sema4D expression in tumor cells of stage IV SCC of the larynx. (B) Sema4D$^{+ve/high}$ expression in TAIs corresponded to negative Sema4D expression in tumor cells of stage IV SCC of gingiva. TAIs; tumor associated inflammatory cells, T; Tumor. (20×; 200 um scale, inset: 40×).
Figure 22:
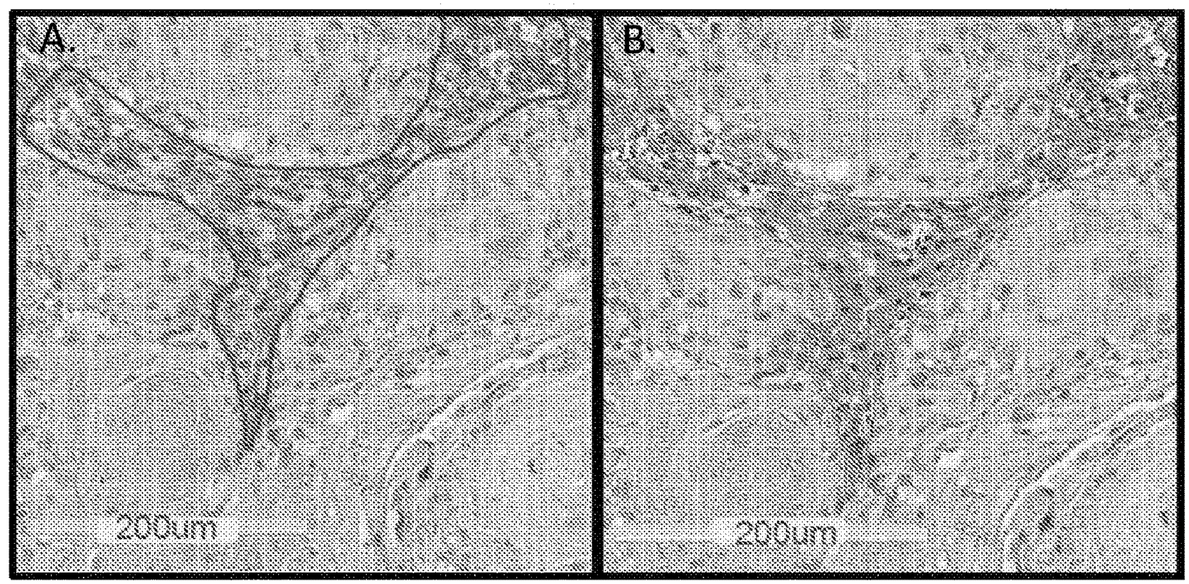
FIG. 22. Sema4D$^{+ve/high}$ TAIs. (A) TAIs infiltrating the stroma of stage II SCC of the right palate were Sema4D$^{+ve/high}$. (B) Digital analysis shows high Sema4D expression (red) in the TAIs with $1.3\times10^6$ strong positive pixel intensity (20×; 200 um scale).

Te peri-tumoral stroma was further investigated for the extent of inflammation. When infiltrating TAIs were present, almost all of them showed positivity for Sema4D (Sema4D$^{+ve/high}$ TAIs). The stroma in Stage I and II HNC tumors showed mild to moderate infiltrate of Sema4D$^{+ve/high}$ TAIs (FIGS. 12A and 12B) (FIG. 22). Stage III HNC tumors were generally moderately inflamed, with considerable overall increase in TAIs infiltration compared to stage I and II, with almost all TAIs staining strongly positive for Sema4D. Stage IV tumors showed prominent increase of Sema4D$^{+ve/high}$ TAIs infiltration in most of the specimens, compared to stages I, II and III, (FIG. 12D and FIG. 14A-14B). Sema4D$^{+ve/high}$ TAIs were statistically negatively associated with Sema4D expression in tumor cells (p=0.0006), where Sema4D$^{-ve/low}$ expression in tumor cells correlated with increased infiltration of Sema4D$^{+ve/high}$ TAIs in the peri-tumoral stroma (Table 1). Sema4D$^{+ve/high}$ TAIs correlated generally with malignancy (p=0.043) and specifically with SCC phenotype (p=0.0004) (Table 7). Inflammatory cells in the lymph nodes with metastatic SCC generally showed strong Sema4D expression (FIG. 12E).

HNC Stratification According to Sema4D and PD-L1 Expression

Programmed death-ligand 1 (PD-L1) expression has been linked to poor patients' prognosis (Lin et al., *PLoS One.* 2015; 10(11): e0142656.; Chen et al., *Oral Oncol.* 2015; 51(11):1004-1010; Mukaigawa et al., *J Surg Oncol.* 2016; 114(1):36-43). The inhibition of PD-1/PD-L1 pathway had shown promising overall response rate in many clinical studies. Yet patients' response had been linked to the initial presence of an inflamed tumor microenvironment (Cho et al., *Oral Oncol.* 2011; 47(12): 1148-1153; Zandberg et al., *Oral Oncol.* 2014; 50(7):627-632; Kirilovsky et al., *Int Immunol.* 2016; 28(8):373-382; Ferris et al., *J Natl Cancer*

Figure 15:
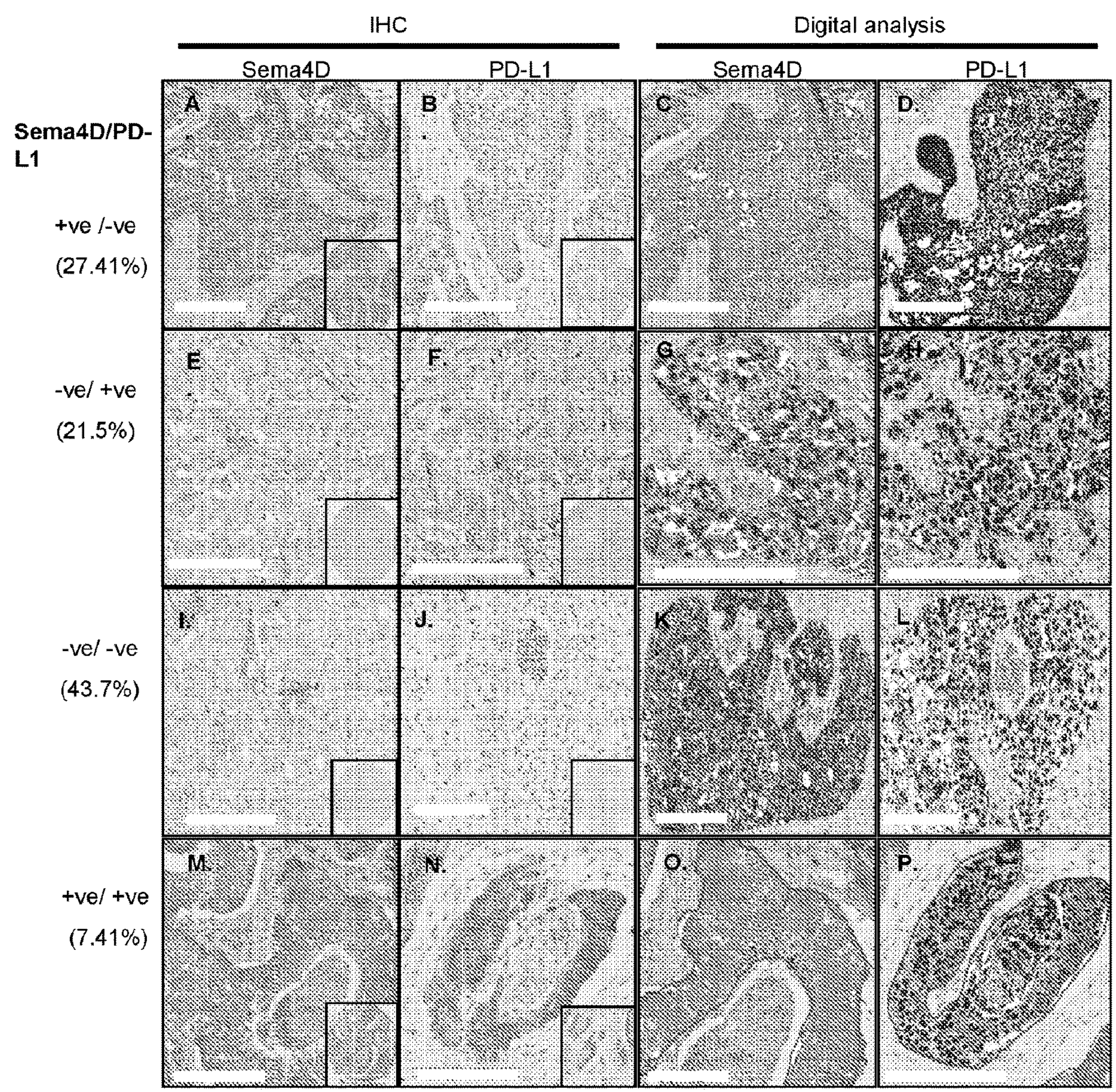
FIG. 15. Stratification of HNC tumors into 4 subtypes according to Sema4D and PD-L1 expression. A-D. Sema4D$^{+ve/high}$/PD-L1$^{-ve/low}$ tumor subtype. (A) A stage III SCC of the larynx with Sema4D$^{+ve/high}$ tumor cells surrounded with fibrotic peri-tumoral stroma. (B) The same tumor as in (A) showed PD-L1$^{-ve/low}$ expression. (C) Total strong pixel intensity for Sema4D stain in (A) ~2×10$^6$. (D) Total strong pixel intensity for PD-L1 stain in (B) <10$^4$. E-H. Sema4D$^{-ve/low}$PD-L1$^{+ve/high}$ tumor subtype. (E) A stage IV SCC of the lip showed Sema4D$^{-ve/low}$ tumor cells with Sema4D$^{+ve/high}$ TAIs in the peri-tumoral stroma. (F) Same tumor as in (E) showed PD-L1$^{+ve/high}$ tumor cells, TAIs were PD-L1$^{-ve/low}$. (G) Total strong pixel intensity of Sema4D stain in (E) of ~1.5×10$^5$. (H) Total strong pixel intensity for PD-L1 stain in (F) ~5.3×10$^6$. I-L. Sema4D$^{-ve/low}$/PD-L1$^{-ve/low}$ tumor subtype. (I) Tumor cells of a stage III SCC of the larynx were Sema4D$^{-ve/low}$, TAIs were Sema4D$^{-ve/high}$. (J) The same tumor as in (I), PD-L1–$^{ve/low}$ for tumor cells and TAIs. (K) Total strong pixel intensity for tumor stain in (I) <10$^4$. (L) Total strong pixel intensity for PD-L1 (J) ~10$^4$. M-P. Sema4D$^{+ve/high}$/PD-L1$^{+ve/high}$ tumor subtype. (M) A sta$_g$e III SCC of the larynx, with tumor cells Sema4D$^{+ve/high}$ with peri-tumoral fibrotic stroma showing focal Sema4D$^{+ve/high}$ TAIs. (N) PD-L1$^{+ve/high}$ in same tumor as in (M) TAIs were PD-L1 negative. (O) Total strong pixel intensity for Sema4D stain in (M) 1.5×10$^6$. (P) Total strong pixel intensity for PD-L1 stain in (N) ~4×10$^6$. (20×; 200 um scale, inset: 40×, pixel intensity was calculated as the mean of 3 annotation layers per tumor core taken at 20×; at area 0.2 mm$^2$. Cut off value for positive is 5×10$^5$).
Figure 23:
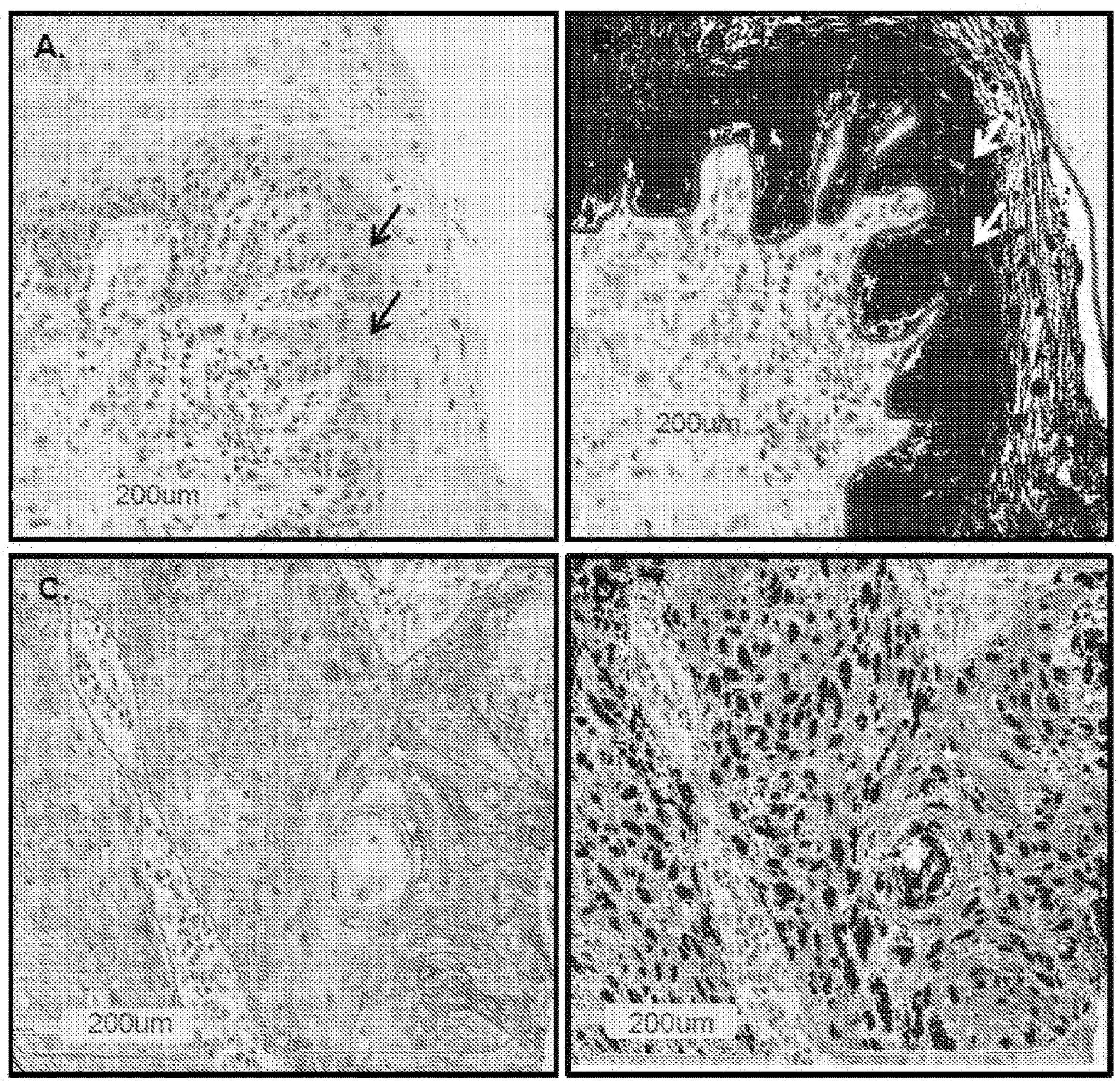
FIG. 23. PD-L1 expression in epithelial tissue adjacent to tumor margin and in tumor cells. (A) PD-L1 is negative in tissue adjacent to tumor margin with a focal positive area (arrows). (B) Digital analysis shows negative expression (blue) with focal positivity (arrows) (20×; 200 um scale). (C) Tumor cells of stage II SCC of the right palate shows PD-L1$^{+ve/high}$ expression in tumor cells, TAIs are PD-L1 negative. (D) PD-L1 staining in (C) showed high level of strong positive pixel intensity of $5.5\times10^6$ (20×; 200 um scale).
Figure 24A:
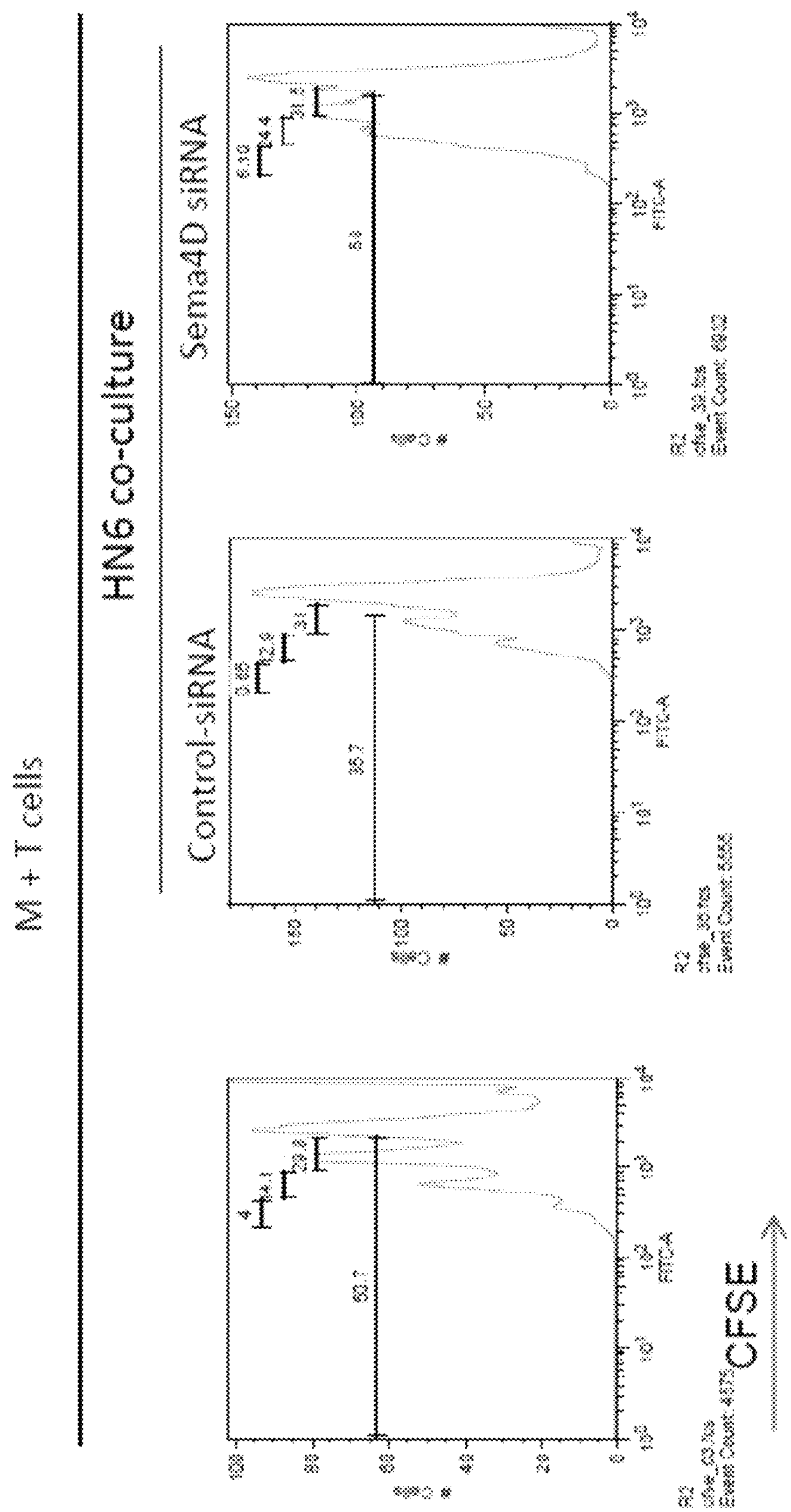
FIG. 24. Sema4D inhibition in HN6 cells recovers T cell proliferation and IFN-γ production in Normoxic and hypoxic conditions. Sema4D inhibition using siRNA in HN6 cell lines for 24 hrs cultured in a trans well with T cells or T cells +Myeloid cells (M:T, 2:1). The siRNA target sequence is CAAGACGCTGCAGTTCGTTAA (SEQ ID NO:7). (A-D). Normoxic conditions. (A) Flowcytometry analysis for tracking T cell proliferation using CFSE. (B) Western blot showing Sema4D knock down in HN6 cells using siRNA. (C) Graphical representation of T cell proliferation detected in A using Flowcytometry analysis. (D) IFN-γ levels upon inhibition of Sema4D detected using ELISA and read using spectrophotometer (E-G). Recapitulating the tumor hypoxic conditions, incubating in 2% Oxygen in hypoxia chambers. CFSE stained T cells activated using anti-CD3, CD28 beads, proliferation detected using flow cytometry. (E) Flowcytometry analysis for tracking T cell proliferation using CF SE under hypoxia. (F) Graphical representation of T cell proliferation detected in E using Flowcytometry analysis. (G) IFN-γ levels upon inhibition of Sema4D under hypoxia, detected using ELISA and read using spectrophotometer
Figure 24B:
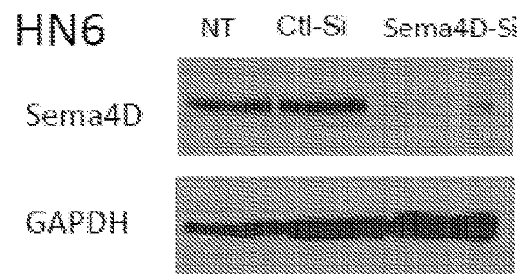
Figure 24C:
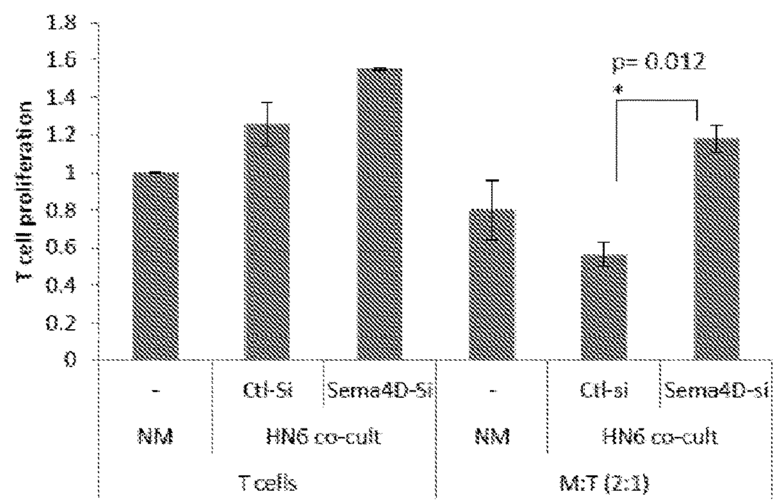
Figure 24D:
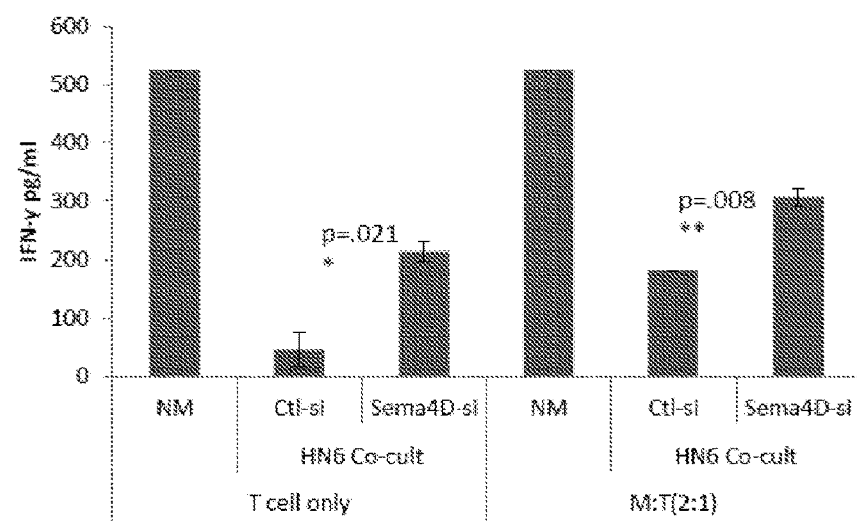
Figure 24E:
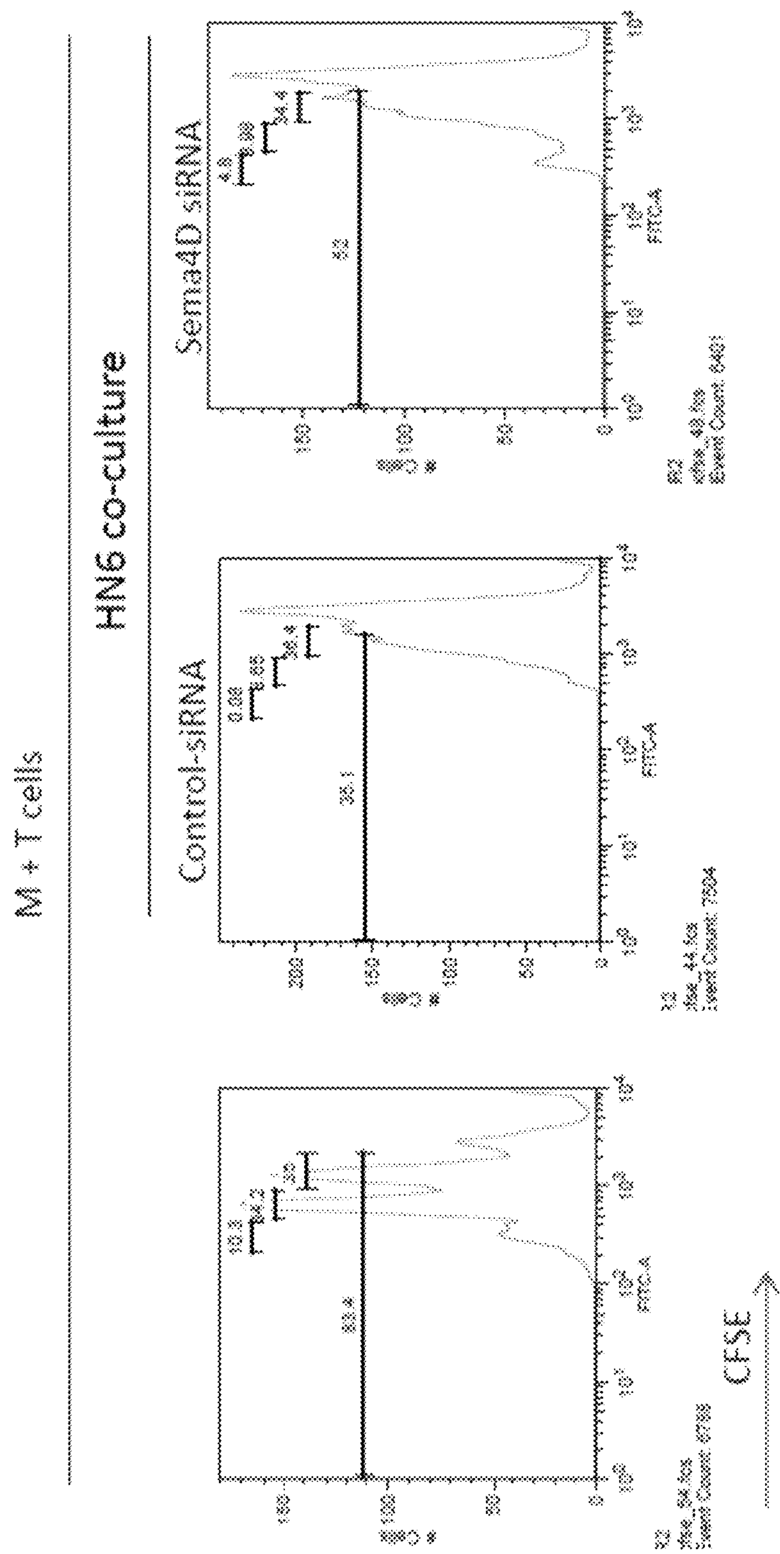
Figure 24F:
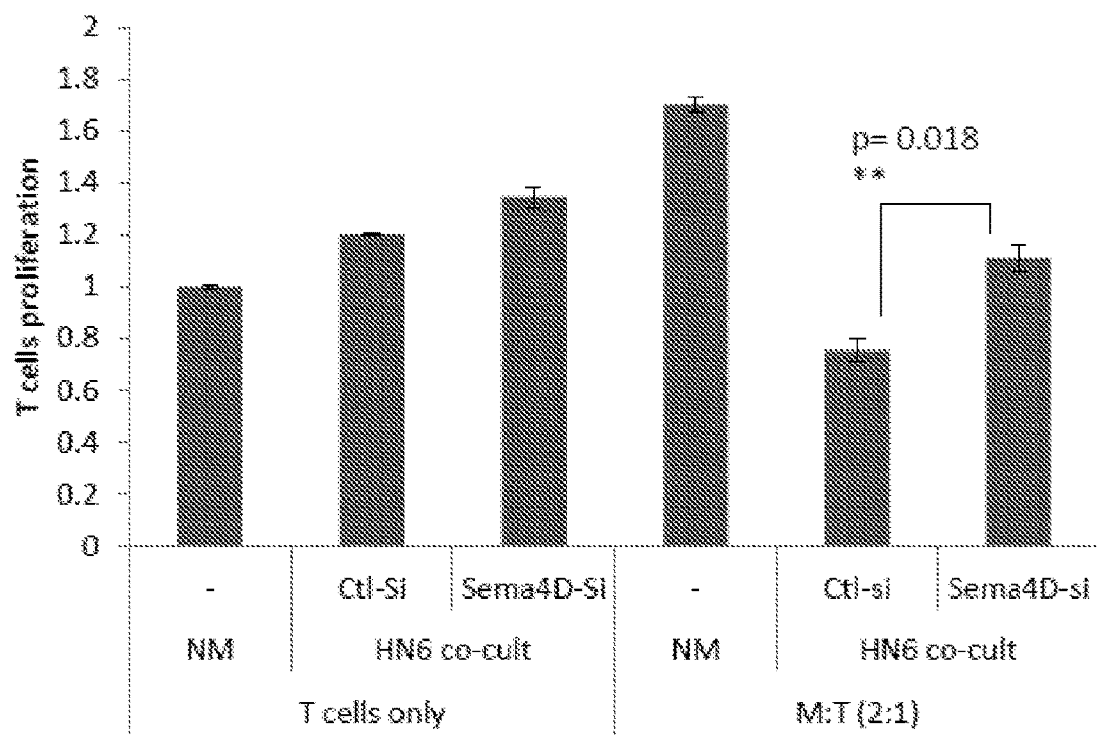
Figure 24G:
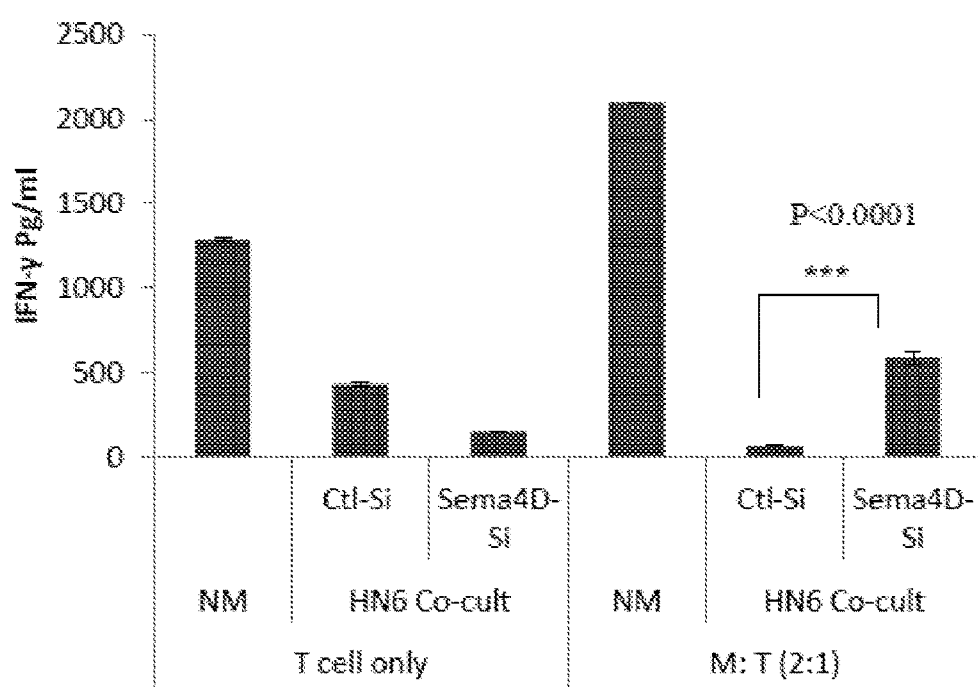

*Inst.* 2016; 108(8)). Our findings that tumor cells expressing Sema4D$^{ve/high}$ correlated positively with a dense fibrotic stroma and inversely with Sema4D$^{+ve/high}$ TAIs, triggered the question; if HNC tumors expressing high Sema4D represent a distinct tumor phenotype other than the inflamed, PD-L1 positive tumors. To investigate the Sema4D/PD-L1 differential expression, we stained the same HNC tumor set studied for Sema4D with PD-L1. The specimens from the normal epithelium, normal salivary glands and epiglottis, were negative for PD-L1 as well as the normal epithelium from the tumor margin (FIG. 23A-23B). When present, PD-L1 expression in tumor cells, was mainly membranous, and was often high and associated with positive cytoplasmic staining. PD-L1$^{-ve/high}$ tumor cells were observed in 31 (23%) cases out of the 136 primary and metastatic malignancies (Table 2) (Table 9). PD-L1 expression in tumor cells did not correlate with tumor staging (p=0.815) or lymph node metastasis (p=0.273) (Table 9), but interestingly, correlated inversely with peri-tumoral stromal fibrosis (p=0.067) and directly with Sema4D$^{+ve/high}$ TAIs (p=0.0139) (Table 3). Sema4D expression was analyzed in correlation to combined PD-L1 expression in both tumor cells and TAIs. In this context, 79% out of the Sema4D$^{+ve/high}$ tumor cells were PD-L1$^{-ve/low}$, and 38.5% out of the PD-L1$^{-ve/low}$ cases were Sema4D$^{+ve/high}$ tumor cells. Most of the PD-L1 and Sema4D negative cases (double negative) showed Sema4D$^{+ve/high}$ TAIs. Only 10 cases (7.4%) out of the total cohort were Sema4D/PD-L1 double positive (FIG. 15, Table 2).

Materials and Methods

HNC Tissue Microarray

Formalin-fixed, paraffin-embedded tissues of HNC tissue microarray (HN802 and HN803c) was obtained from US Biomax (Rockville, Md.). The tissue microarray of hundred and sixty cases of head and neck cancer with normal tissue included demographic data, TNM system, clinical stage, and pathologic grade. The hematoxylin and eosin sections were examined by an oral and maxillofacial (OMF) pathologist to verify histopathological diagnosis prior to immunohistochemical (IHC) staining.

Serum Samples

The patient specimens were collected under an approved protocol by the Institutional Review Board at the University of Maryland School of Medicine. Banked HNC patient samples were obtained from patients with their written and informed consent. Healthy donor sera were purchased from Innovative research (Novi, Mich.).

Immunohistochemistry

For Sema4D staining, the avidin-biotin complex (ABC) technique was used following Vectastain elite ABC kit (PK-6102) mouse IgG (Vector Laboratories, CA). Briefly, tissue sections were deparaffinized in xylene, rehydrated in graded ethanol, treated with Tris-EDTA buffer for antigen retrieval, and quenched in hydrogen peroxide to block endogenous peroxidase. Tissue sections were blocked with 2.5% normal serum, incubated overnight at 4 degrees C. with anti-Sema4D antibody 1:200, (clone 30/CD100; BD Transduction Laboratories), followed by biotinylated secondary antibody (catalog no. BA-9200) and then the ABC reagent. Diaminobenzidine (SK-4105) was used as chromogen and counterstained with Mayer's hematoxylin (Sigma-Aldrich Corp.). The Sema4D labeling index (LI) reflecting the intensity and extent of staining in the tumor cells was defined semiquantitatively as (0, 1, 2, and 3) and digitally using the Aperio software (Positive Pixel count v9) Blue, yellow, orange and red. Where (0) was negative (Blue digitally), (1) was diffuse weak staining (yellow digitally), (2) diffuse weak positivity with scattered strong positive <25% (yellow with scattered orange digitally), and (3) was for diffuse strong positivity or focal strong positive >25% (orange and red digitally). Since Sema4D showed negative to weak expression with focal strong positivity in some normal epithelium (FIG. 19), the cut off value semi quantitatively for Sema4D$^{+ve/high}$ in tumor cells was the score (3), and digitally was total strong pixel intensity of $\geq 5\times 10^5$ (diffuse orange to red), calculated as the median value between Sema4D$^{-ve/low}$ and Sema4D$^{+ve/high}$ expression (FIG. 21). For PD-L1 staining, PD-L1 primary antibody clone SP142 (Roche/Ventana medical system, Inc) was used following the vendor recommended assay. Since PD-L1 was negative in normal epithelium, the cut off value for PD-L1$^{+ve/high}$ was strong focal expression ≥1% in tumor cells or in TAIs or both, and using the same cutoff value digitally as with Sema4D (Madore et al., *Clin Cancer Res.* 2016; 22(15):3915-3923). The strong pixel intensity for all the stains was calculated as the mean of three representative annotation layers of ~0.2 mm$^2$ area at 20× magnification, 200 um scale.

Stromal analysis for fibrosis or TAIs infiltrate was carried out by OMP pathologist on the H&E and IHC stained sections under light microscopy. For analysis of fibrosis in the tumor stroma, delicately fibrous stroma (+), moderately fibrotic (++) and densely fibrotic (+++) parameters were used. For the analysis of the tumor associated inflammatory cells (TAIs), (0, 1, 2, and 3) LI was used to reflect the extent of infiltrate of Sema4D$^{+ve/high}$ TAIs in the peri-tumoral stroma. Where (0) was stroma completely negative, (1) was mild, (2) moderate and (3) for heavy infiltrate. The cut off value for the extent of infiltrate of Sema4D$^{+ve/high}$ TAIs was the score (2). Photos were taken using the Aperio ScanScope and Image Scope software.

Sema4D ELISA

The serum concentration of Sema4D was determined by ELISA. Immulon 4 HBX microtiter plates (Thermo Scientific, Waltham, Mass.) were coated with 50 microliters of undiluted serum, washed, then incubated with anti-human CD100 antibody (clone: 133-1C6; Novus Biologicals). Goat anti-mouse IgM-HRP (catalog no. M31507; Life Technologies) was added followed by detection with TMB (Pierce). The serum concentrations of Sema4D were calculated using the standard curve established for recombinant Sema4D (catalog no. 310-29) (Peprotech, RockyHill, N.J.). The detection limit was 3.1 ng/mL. For detection of TGF-β1 by WSU-HN6 tumor cells, Human ELISA TGF-β1 total (catalog no. 436707) was purchased from BioLegend (San Diego, Calif.). Conditioned medium was run in triplicate and plates were read using a BioTek Epoch microplate spectrophotometer at 450 nm wavelength.

Cell Lines, Sema4D shRNA and Lentivirus Infections

The cell lines, normal oral keratinocytes (NOK) and oral squamous cell carcinoma WSU-HN6, derived from a stage III (T3N2bM0) primary malignancy of the base of the tongue, were DNA authenticated at (Johns Hopkins Genetic Resources Core Facility, Baltimore, Md.) to ensure consistency in cell identity in comparison with their source (Jeon et al., *Int J Cancer.* 2004; 112(2):249-258). To detect TGF-β1 production by tumor cells in response to Sema4D, Sema4D knockdown using shRNA lentivirus system was used. The lentivirus and shRNA system were a gift of Dr.

John R. Basile (University of Maryland, Baltimore) (Basile et al., *Proc Natl Acad Sci USA*. 2006; 103(24):9017-9022). In brief, the shRNA sequences for human Sema4D were obtained from Cold Spring Harbor Laboratory's RNAi library (RNAi Codex; http:katahdin.cshl.org: 9331_homepage_portal_scripts_main2.pl). The oligonucleotides (Invitrogen, Grand Island, N.Y.) used to knockdown Sema4D protein levels were 5'-GGCCTGAGGACCTTGCAGAAGA-3' (SEQ ID NO:3). The Sema4D shRNA oligonucleotides were cloned into lentiviral expression vector pWPI GW as previously described (Basile et al., *Proc Natl Acad Sci USA*. 2006; 103(24):9017-9022). pWPI (empty) vector was used as negative control. Transductions were performed using FuGENE HD transfection reagent (catalog no. E2311; Promega).

Statistical Analysis

The primary outcome variable, staining status of Sema4D in tumor tissue, was defined as Sema4D$^{+ve/high}$ (score=3) and Sema4D$^{-ve/low}$ (score=0, 1, 2); and the secondary outcome variable, PD-L1, defined as PD-L1$^{+ve/high}$ (≥1%) and negative low (<1%). The independent variables are tumor clinical stage coded as (I+II, III, and IV), Nodal metastasis (yes/no), Sema4D$^{+ve/high}$ TAIs infiltrate (moderate to heavy are scores 2, 3), negative to low are 0, 1) and fibrotic tumor microenvironment as (+,++,+++). Other factors included patient characteristics such as age (<45, 45-54, 55-64, 65+), sex, organ category (Oral cavity, Salivary glands, Larynx-Pharynx-Nose, Lymph node), histological grade (1, 2, 3), Pathology (SCC, SGA) and type of tissue (normal or malignant). The associations of two categorical variables were evaluated using two-sided Fisher Exact test or Chi-square test and the association of a continuous variable and a categorical variable were evaluated using two sample t-test or ANOVA F test for the categorical variable having more than two levels. P-values <0.05 were considered statistically significant. If at least one categorical variable had more than two levels and the overall test p-value <0.05, Post Hoc pairwise comparisons were performed. Bonferroni corrections were used for adjusting the p-values of the post hoc tests for multiple comparisons (Dunn). All the analyses were conducted using SAS 9.3.2 software. In addition, the associations of Sema4D levels by ELISA were analyzed using Graph pad Prism software, with age, sex, tumor stage etc. were evaluated by two sample t-test or ANOVA F test.

Sema4D Detection in Sera of HNC Patients

Figure 16:
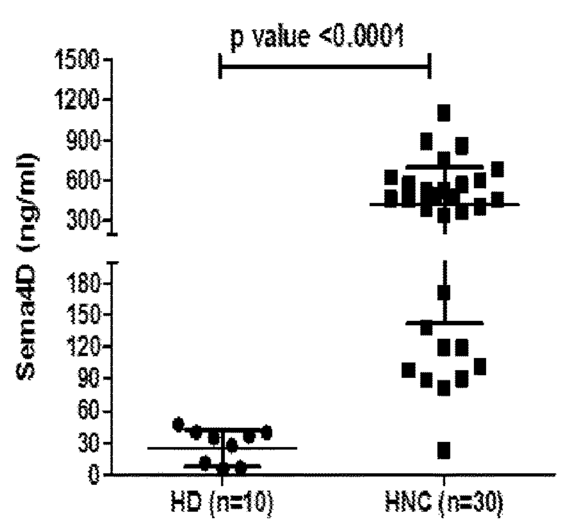
FIG. 16. Analysis of Sema4D in sera of HNC patients. (A) ELISA assay of Sema4D in sera of HNC patients compared to HD ($p<0.0001$). Two ranges of Sema4D level were detected, a low range group and a higher range group. (B) Sema4D in the sera of HNC patients showed highest distribution in stage III ($p=0.055$). HD; Healthy donors, HN; Head and Neck cancer patients.
Figure 16:
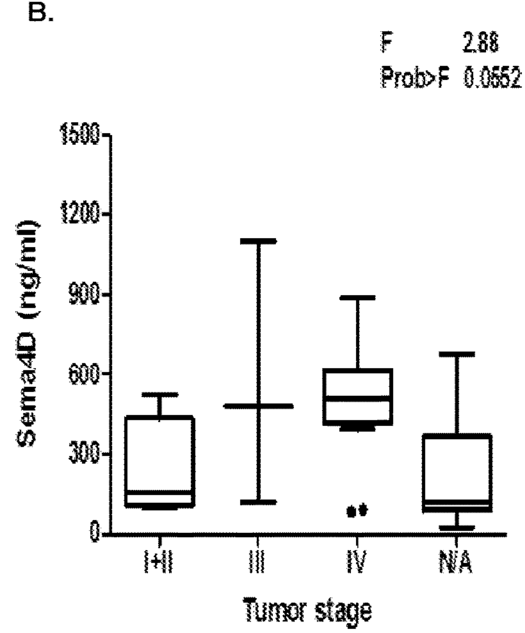
Figure 17:
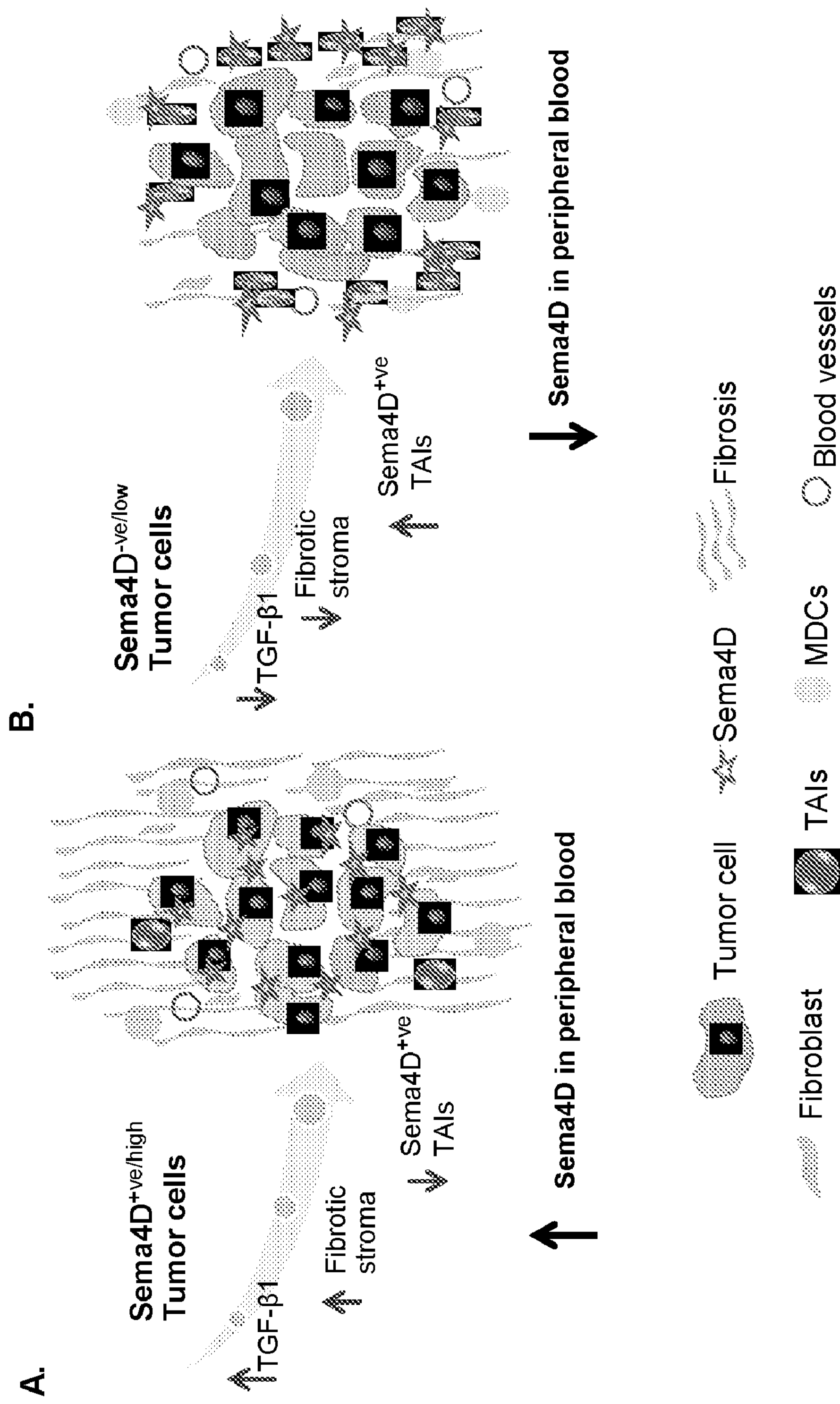
FIG. 17. A model for Sema4D$^{+ve/high}$ tumor cells with a fibrotic peri-tumoral stromal phenotype. (A) Sema4D$^{+ve/high}$ tumor cells induce increased production of TGF-β1 which increases deposition of ECM and collagen fibers. This model is suggestive of high Sema4D levels in peripheral blood. (B) Sema4D$^{-ve/low}$ tumor cells with inflamed stroma. Sema4D$^{-ve/low}$ tumors has decreased level of TGF-β1 production, less fibrotic and more into the loose peri-tumoral stroma with increased infiltrate of Sema4D$^{+ve/high}$ TAIs. This model is suggestive of low Sema4D levels in peripheral blood. MDSC: Myeloid derived suppressor cells. TAIs: Tumor Associated Inflammatory cells.

The current findings of Sema4D expression in tumor cells and in TAIs, in addition to previous in vitro study showing that HNC cells can produce soluble Sema4D in the tumor-conditioned medium, led to an investigation of whether soluble Sema4D can be detected in patient's peripheral blood. ELISA was used to assess Sema4D levels in 10 healthy donors (HD) and 30 HNC patients' specimens. In the 10 HD, serum Sema4D levels were 24.6±17.3 ng/mL. There was a statistically insignificant gender difference: levels of sera Sema4D in men (27.3±15.9 ng/mL, n=9) were higher than that in women (not detectable, n=1). The demographics of the 30 HNC patients in this study are summarized in Table 4. The levels of Sema4D in the HNC sera (418.2±276.8 ng/mL) were significantly higher than those in HD (27.3±15.9 ng/mL) (p<0.0001) (FIG. 16A). The data showed Sema4D levels clustered into two groups; notably both were significantly higher than in HD (FIG. 16A). One cluster showed lower values with a mean of 114.68 ng/ml, while the other tumor cluster had higher values with a mean of 575.8 ng/ml. in contrast to HD, there were higher Sema4D levels in the sera of female compared to male patients (393±258 ng/mL in males n=27 vs. 642±398 ng/mL in females, n=3) (Table 4). The expression of Sema4D in the blood seemed to correlate significantly with stage III tumors (FIG. 16B). There was no correlation between lymph node metastasis and soluble Sema4D levels (Table 4). Importantly, these data demonstrate the prognostic potential a Sema4D in peripheral blood of HNC patients.

TABLE 1

Sema4D expression in HNC tumor cells in correlation to tumor progression, peri-tumoral stromal fibrosis and Sema4D$^{+ve/high}$ TAIs.

| | Sema4D expression in tumor cells | | | |
|---|---|---|---|---|
| | −ve/low No (%) | +ve/high No (%) | Total | P-value |
| Tumor stage | | | | |
| I + II | 41 (73.21) | 15 (26.79) | 56 | 0.0141 |
| III | 16 (45.71) | 19 (54.29) | 35 | |
| IV | 25 (73.53) | 9 (26.47) | 34 | |
| Total | 82 (65.6) | 43 (34.4) | 125 | |
| Lymph nodal metastasis | | | | |
| Yes | 26 (56.62) | 20 (43.48) | 46 | 0.117 |
| No | 63 (70) | 27 (30) | 90 | |
| Total | 89 (65.4) | 47 (34.6) | 136 | |
| Stromal Fibrosis * | | | | |
| Delicate | 37 (82.22) | 8 (17.78) | 45 | 0.0001 |
| Moderate | 20 (76.92) | 6 (23.08) | 26 | |
| Dense | 7 (23.33) | 23 (76.67) | 30 | |
| Total | 64 (63.3) | 37 (36.6) | 101 | |
| Sema4D$^{+ve/high}$ TAIs infiltrate | | | | |
| No/low | 28 (50.91) | 27 (49.09) | 55 | 0.0006 |
| Yes/high | 56 (80) | 14 (20) | 70 | |
| Total | 89 (71.2) | 41 (32.8) | 125 | |

* 24 specimens were excluded from the analysis of the fibrosis category, due to dominating tumor islands with no abundant surrounding stroma to be assessed.

TABLE 2

Differential expression of Sema4D and PD-L1 in HNC.

| Sema4D in tumor cells | PD-L1 in tumor cells −ve/low | PD-L1 in tumor cells +ve/high | Total | P-value |
|---|---|---|---|---|
| −ve/low | 65 (48%) | 23 (17%) | 88 (65%) | 0.23 |
| +ve/high | 39 (29%) | 8 (6%) | 47 (35%) | |
| Total | 104 (77%) | 31 (23%) | 135 (100%) | |

| Sema4D in tumor cells | PD-L1 in tumor cells and TAIs −ve/low | PD-L1 in tumor cells and TAIs +ve/high | Total | P-value |
|---|---|---|---|---|
| −ve/low | 59 (43.7%) | 29 (21.5%) | 88 (65.2%) | 0.153 |
| +ve/high | 37 (27.4%) | 10 (7.4%) | 47 (34.8) | |
| Total | 96 (72%) | 39 (28%) | 135 (100%) | |

TABLE 3

PD-L1 expression in relation to peri-tumoral fibrosis and Sema4D expressing TAIs.

| | PD-L1 expression in tumor cells | | | |
|---|---|---|---|---|
| | −ve/low | +ve/high | Total | P-value |
| Stromal fibrosis | | | | |
| Delicate | 30 (66.67%) | 15 (33.33%) | 45 | 0.06 |
| Moderate | 18 (72.00%) | 7 (28.00%) | 25 | |
| Dense | 27 (90.00%) | 3 (10.00%) | 30 | |
| Total | 75 | 25 | 100 | |
| Sema4D$^{+ve/high}$ TAIs infiltrate | | | | |
| No (0, 1) | 48 (87.27%) | 7 (12.73%) | 55 | 0.01 |
| Yes (2, 3) | 48 (68.57%) | 22 (31.43%) | 70 | |
| Total | 96 | 29 | 125 | |

TABLE 4

Sema4D analysis in the sera of HNC patients in relation to demographics and clinical characteristics

| Characteristics | Number of patients | Sema4D (ng/ml) | P-value |
|---|---|---|---|
| Mean age ± SD | | | |
| (year) | 30 | 57.7 ± 11.6 | |
| Race | | | |
| White | 26 | 390.6 ± 279 | 0.4 |
| Black | 3 | 511.6 ± 115 | |
| Asian | 1 | 854 | |
| Sex | | | |
| Male | 27 | 393 ± 258 | 0.142 |
| Female | 3 | 642 ± 398 | |
| Stage | | | |
| I | 1 | 97.7 | 0.055 |
| II | 3 | 277.7 ± 123 | |
| III | 3 | 566 ± 286 | |
| IV | 16 | 512.5 ± 55 | |
| N/A | 7 | 245.5 ± 87 | |
| Location | | | |
| Oral | 13 | 466 ± 95 | 0.5 |
| OP & BOT & tonsils | 15 | 395 ± 57 | |
| Supra/trans glottic | 2 | 600 ± 79 | |
| LN status | | | |
| N0 | 5 | 406 ± 423 | 0.559 |
| N1/N2/N3 | 18 | 488 ± 228 | |

TABLE 5

Descriptive analysis of Sema4D staining according to tissue type.

| | Sema4D expression in tumor cells and normal tissue | | | | |
|---|---|---|---|---|---|
| Type | −ve/low | +ve/high | N/A | Total | Net |
| *Primary Malignancy | 85 (66.4%) | 43 (33.6%) | 3 | 131 | 128 (82.1%) |
| #Metastatic | 4 (50.0%) | 4 (50%) | 0 | 8 | 8 (5.1%) |
| ##Normal/NAT | 11 (55%) | 9 (45%) | 1 | 21 | 20 (12.8%) |
| Total | 100 (52.6%) | 56 (35.9%) | 4 | 160 | 156 (100%) |

*Primary malignancies had 119 SCC (76.3%), 9 (5.7%) SGA.

4 SCC (2.5%) and 4 SGA (2.5%), metastatic to lymph nodes.

Normal tissue: 11 Tongue, 2 normal tissue adjacent to tumor margin (NAT), 3 Salivary gland tissue, and 4 epiglottis.

TABLE 6

Sema4D expression in tumor cells in correlation to Patient's demographics and histological grading.

| | Sema4D expression in tumor cells | | | |
|---|---|---|---|---|
| | −ve/low No (%) | +ve/high No (%) | Total | P value |
| Age | No (%) | No (%) | | |
| <45 | 14 (70) | 6 (30) | 20 | 0.745 |
| 45-54 | 29 (61.7) | 18 (38.3) | 47 | |
| 55-64 | 21 (61.76) | 13 (38.24) | 34 | |
| 65+ | 25 (71.43) | 10 (28.57) | 35 | |
| Total | 89 | 47 | 136 | |
| Gender | | | | |
| F | 46 (66.67) | 23 (33.33) | 69 | 0.76 |
| M | 43 (64.18) | 24 (35.82) | 67 | |
| Total | 89 | 47 | 136 | |
| Organ | | | | |
| Oral cavity and salivary glands | 34 (70.83) | 14 (29.17) | 48 | 0.458 |
| larynx, pharynx and nasal cavity | 51 (63.75) | 29 (36.25) | 80 | |
| metastatic to lymph node | 4 (50%) | 4 (50%) | 8 | |
| Total | 89 | 47 | 136 | |
| Pathological Diagnosis | | | | |
| Normal | 11 (55) | 9 (45) | 20 | 0.0024 |
| SCC | 86 (69.67) | 37 (30.33) | 123 | |
| SGA | 3 (23.08) | 10 (76.92) | 13 | |
| Total | 100 | 56 | 156 | |
| SCC Hist grade | | | | |
| 1 | 28 (71.79) | 11 (28.21) | 36 | 0.513 |
| 2 | 35 (64.81) | 19 (35.19) | 54 | |
| 3 | 20 (76.92) | 6 (23.08) | 26 | |
| | 83 | 36 | 119 | |

TABLE 7

| Sema4D$^{+ve/high}$ TAIs in correlation to malignancy, pathological diagnosis and clinical staging | | | | |
|---|---|---|---|---|
| | TAIs expressing Sema4D | | | |
| | No (0, 1) N (%) | Yes (2, 3) N (%) | Total | P value |
| Malignancy | | | | |
| Normal | 13 (68.42) | 6 (31.58) | 19 | 0.043 |
| Malignant | 55 (43.65) | 71 (56.35) | 126 | |
| Total | 68 | 77 | 145 | |
| Pathological Diagnosis | | | | |
| SCC | 46 (39.32) | 71 (60.68) | 117 | 0.0004 |
| SGA | 9 (100) | 0 (0) | 9 | |
| Total | 55 | 71 | 126 | |
| Tumor stage | | | | |
| I + II | 26 (47.27) | 29 (52.73) | 55 | 0.79 |
| III | 15 (44.12) | 18 (55.88) | 33 | |
| IV | 14 (40.00) | 21 (60.00) | 35 | |
| Total | 55 | 68 | 123 | |

TABLE 8

| Descriptive analysis of PD-L1 staining according to tissue type | | | | | |
|---|---|---|---|---|---|
| | PD-L1 expression in malignant tissue and normal cells | | | | |
| Type | −ve/low | +ve/high | N/A | Total | Net (%) |
| Primary Malignancy | 98 (74.81%) | 30 (22.90%) | 3 (2.29%) | 131 | 128 (82.1%) |
| Metastasis | 7 (87.50%) | 1 (12.50%) | 0 (0.00%) | 8 | 8 (5.1%) |

TABLE 8-continued

| Descriptive analysis of PD-L1 staining according to tissue type | | | | | |
|---|---|---|---|---|---|
| | PD-L1 expression in malignant tissue and normal cells | | | | |
| Type | −ve/low | +ve/high | N/A | Total | Net (%) |
| Normal/NAT | 21 (100%) | 0 0.00 | 0 (0.0%) | 21 | 21 (12.8%) |
| Total | 126 | 31 | 3 | 160 | 157 (100%) |

TABLE 9

| PD-L1 expression in correlation to tumor progression | | | | |
|---|---|---|---|---|
| | PD-L1 expression in tumor tissue | | | |
| | −ve/low | +ve/high | Total | P value |
| Tumor Stage | | | | |
| I + II | 44 (80%) | 11 (20%) | 55 | 0.816 |
| III | 27 (77.1%) | 8 (22.9%) | 35 | |
| IV | 26 (74.3%) | 9 (25.7%) | 35 | |
| Total | 97 | 28 | 125 | |
| Nodal metastasis | | | | |
| No (0, 1) | 72 (80%) | 18 (20%) | 55 | 0.277 |
| Yes (2, 3) | 33 (71.7%) | 13 (28.3%) | 70 | |
| Total | 105 | 31 | 136 | |

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

I claim:

1. A method of inhibiting tumor-mediated immunosuppression in a subject, comprising administering to the subject a therapeutically effective amount of an agent that inhibits the activity of Semaphorin 4D, wherein the agent comprises a nucleic acid molecule that comprises a nucleotide sequence that binds to at least a portion of a nucleotide sequence of Semaphorin 4D, wherein the nucleotide sequence of Semaphorin 4D is SEQ ID NO:2, wherein a portion of the nucleic acid molecule is 100% complementary to SEQ ID NO:4.

2. The method of claim 1, wherein the agent decreases the expression level of Semaphorin 4D.

3. The method of claim 1, wherein the subject has a cancer selected from head and neck cancer and lymphoma.

4. The method of claim 1, wherein the inhibition of Semaphorin 4D decreases the level of myeloid-derived suppressor cells in the tumor microenvironment.

5. The method of claim 4, wherein the myeloid-derived suppressor cells have a phenotype that is $CD33^+$, $CD11b^+$, and $HLA\text{-}DR^{-/low}$.

6. The method of claim 1, wherein the inhibition of Semaphorin 4D results in one or more of the following effects:

i) an increase in T cell proliferation;

ii) an increase in IFN-γ levels;

iii) a decrease in IL-4 levels;

iv) a decrease in arginase-1 production by $CD33^+$ myeloid cells;

v) a decrease in NO production by $CD33^+$ myeloid cells;

vi) a decrease in IL-10 by $CD33^+$ myeloid cells;

vii) a decrease in TGF-β1 production by $CD33^+$ myeloid cells;

viii) a decrease in TGF-β1 production by tumor cells;

ix) an increase in effector Th1 T cells ($CD4^+Tbet^+$);

x) an increase in cytotoxic T cells ($CD8^+Tbet^+$); and xi) a decrease in Tregs cells ($CD4^+CD25^+FoxP3^+$).

7. The method of claim 1, wherein the agent comprises a DNA molecule or an RNA molecule.

8. The method of claim 7, wherein the agent comprises an anti-sense DNA molecule or an anti-sense RNA molecule.

9. The method of claim 7, wherein the agent comprises a small interfering RNA (siRNA) molecule.

10. The method of claim 1, wherein the agent comprises a small hairpin RNA (shRNA) molecule.

11. The method of claim 1, wherein the method further comprises administering to the subject an effective amount of an immunotherapeutic anti-cancer agent.

12. A method of inhibiting tumor-mediated immunosuppression in a subject, comprising administering to the subject a therapeutically effective amount of an agent that inhibits the activity of Semaphorin 4D, wherein the agent comprises a nucleic acid molecule that comprises a nucleotide sequence that binds to at least a portion of a nucleotide sequence of Semaphorin 4D, wherein the agent comprises a small interfering RNA (siRNA) molecule, wherein the siRNA molecule targets the sequence SEQ ID NO:7.

13. A method of inhibiting tumor-mediated immunosuppression in a subject, comprising administering to the subject a therapeutically effective amount of an agent that inhibits the activity of Semaphorin 4D, wherein the agent comprises a small hairpin RNA (shRNA) molecule, wherein the agent comprises an expression vector comprising SEQ ID NO:3.

* * * * *

SEQUENCE LISTING

```
<160> NUMBER OF SEQ ID NOS: 7

<210> SEQ ID NO 1
<211> LENGTH: 862
<212> TYPE: PRT
<213> ORGANISM: Homo sapiens

<400> SEQUENCE: 1

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60
```

```
Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125

Asn Ala Phe Gln Pro Ala Cys Asp His Leu Asn Leu Thr Ser Phe Lys
    130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
    210                 215                 220

Asp Gly Glu Asp Asp Arg Val Tyr Phe Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Arg Pro Asp Ser Gly Leu
        275                 280                 285

Val Phe Asn Val Leu Arg Asp Val Phe Val Leu Arg Ser Pro Gly Leu
    290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Thr Val Glu Gln Ser His
            340                 345                 350

Thr Lys Trp Val Arg Tyr Asn Gly Pro Val Pro Lys Pro Arg Pro Gly
        355                 360                 365

Ala Cys Ile Asp Ser Glu Ala Arg Ala Ala Asn Tyr Thr Ser Ser Leu
    370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
            420                 425                 430

Gly Thr Val Tyr Asp Val Met Phe Val Ser Thr Asp Arg Gly Ala Leu
        435                 440                 445

His Lys Ala Ile Ser Leu Glu His Ala Val His Ile Ile Glu Glu Thr
    450                 455                 460

Gln Leu Phe Gln Asp Phe Glu Pro Val Gln Thr Leu Leu Leu Ser Ser
465                 470                 475                 480

Lys Lys Gly Asn Arg Phe Val Tyr Ala Gly Ser Asn Ser Gly Val Val
```

```
                485                 490                 495

Gln Ala Pro Leu Ala Phe Cys Gly Lys His Gly Thr Cys Glu Asp Cys
            500                 505                 510

Val Leu Ala Arg Asp Pro Tyr Cys Ala Trp Ser Pro Pro Thr Ala Thr
        515                 520                 525

Cys Val Ala Leu His Gln Thr Glu Ser Pro Ser Arg Gly Leu Ile Gln
    530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Gly Thr Ala Glu Leu Lys Cys
                565                 570                 575

Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
        595                 600                 605

Leu Leu Ile Phe Asn Leu Ser Glu Gly Asp Ser Gly Val Tyr Gln Cys
    610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Val Ala Pro
                645                 650                 655

Thr Leu Ser Val Val Gln Thr Glu Gly Ser Arg Ile Ala Thr Lys Val
            660                 665                 670

Leu Val Ala Ser Thr Gln Gly Ser Ser Pro Pro Thr Pro Ala Val Gln
        675                 680                 685

Ala Thr Ser Ser Gly Ala Ile Thr Leu Pro Pro Lys Pro Ala Pro Thr
    690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Phe Phe Phe Val Leu Phe Leu Cys Leu Phe Phe
            740                 745                 750

Tyr Asn Cys Tyr Lys Gly Tyr Leu Pro Arg Gln Cys Leu Lys Phe Arg
        755                 760                 765

Ser Ala Leu Leu Ile Gly Lys Lys Lys Pro Lys Ser Asp Phe Cys Asp
    770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
                805                 810                 815

Thr Glu Gln Asp Thr Ile Thr Ser Lys Val Pro Thr Asp Arg Glu Asp
            820                 825                 830

Ser Gln Arg Ile Asp Asp Leu Ser Ala Arg Asp Lys Pro Phe Asp Val
        835                 840                 845

Lys Cys Glu Leu Lys Phe Ala Asp Ser Asp Ala Asp Gly Asp
    850                 855                 860


<210> SEQ ID NO 2
<211> LENGTH: 4157
<212> TYPE: DNA
<213> ORGANISM: Homo sapiens

<400> SEQUENCE: 2
```

```
ctgagccgca tctgcaatag cacacttgcc cggccacctg ctgccgtgag cctttgctgc     60
tgaagcccct ggggtcgcct ctacctgatg aggatgtgca cccccattag gggggctgctc   120
atggcccttg cagtgatgtt tgggacagcg atggcatttg cacccatacc ccggatcacc    180
tgggagcaca gagaggtgca cctggtgcag tttcatgagc cagacatcta caactactca    240
gccttgctgc tgagcgagga caaggacacc ttgtacatag gtgcccggga ggcggtcttc    300
gctgtgaacg cactcaacat ctccgagaag cagcatgagg tgtattggaa ggtctcagaa    360
gacaaaaaag caaaatgtgc agaaaagggg aaatcaaaac agacagagtg cctcaactac    420
atccgggtgc tgcagccact cagcgccact tccctttacg tgtgtgggac caacgcattc    480
cagccggcct gtgaccacct gaacttaaca tcctttaagt ttctggggaa aaatgaagat    540
ggcaaaggaa gatgtccctt tgacccagca cacagctaca catccgtcat ggttgatgga    600
gaactttatt cggggacgtc gtataatttt ttgggaagtg aacccatcat ctcccgaaat    660
tcttcccaca gtcctctgag gacagaatat gcaatccctt ggctgaacga gcctagtttc    720
gtgtttgctg acgtgatccg aaaaagccca gacagccccg acggcgagga tgacagggtc    780
tacttcttct tcacggaggt gtctgtggag tatgagtttg tgttcagggt gctgatccca    840
cggatagcaa gagtgtgcaa gggggaccag ggcggcctga ggaccttgca gaagaaatgg    900
acctccttcc tgaaagcccg actcatctgc tcccggccag acagcggctt ggtcttcaat    960
gtgctgcggg atgtcttcgt gctcaggtcc ccgggcctga aggtgcctgt gttctatgca   1020
ctcttcaccc cacagctgaa caacgtgggg ctgtcggcag tgtgcgccta caacctgtcc   1080
acagccgagg aggtcttctc ccacgggaag tacatgcaga gcaccacagt ggagcagtcc   1140
cacaccaagt gggtgcgcta taatggcccg gtacccaagc cgcggcctgg agcgtgcatc   1200
gacagcgagg cacgggccgc caactacacc agctccttga atttgccaga caagacgctg   1260
cagttcgtta aagaccaccc tttgatggat gactcggtaa ccccaataga caacaggccc   1320
aggttaatca agaaagatgt gaactacacc cagatcgtgg tggaccggac ccaggccctg   1380
gatgggactg tctatgatgt catgtttgtc agcacagacc ggggagctct gcacaaagcc   1440
atcagcctcg agcacgctgt tcacatcatc gaggagaccc agctcttcca ggactttgag   1500
ccagtccaga ccctgctgct gtcttcaaag aagggcaaca ggtttgtcta tgctggctct   1560
aactcgggcg tggtccaggc cccgctggcc ttctgtggga agcacggcac ctgcgaggac   1620
tgtgtgctgg cgcgggaccc ctactgcgcc tggagcccgc ccacagcgac ctgcgtggct   1680
ctgcaccaga ccgagagccc cagcaggggt ttgattcagg agatgagcgg cgatgcttct   1740
gtgtgcccgg ataaaagtaa aggaagttac cggcagcatt ttttcaagca cggtggcaca   1800
gcggaactga aatgctccca aaaatccaac ctggcccggg tcttttggaa gttccagaat   1860
ggcgtgttga aggccgagag ccccaagtac ggtcttatgg gcagaaaaaa cttgctcatc   1920
ttcaacttgt cagaaggaga cagtggggtg taccagtgcc tgtcagagga gagggttaag   1980
aacaaaaacgg tcttccaagt ggtcgccaag cacgtcctgg aagtgaaggt ggttccaaag   2040
cccgtagtgg cccccacctt gtcagttgtt cagacagaag gtagtaggat tgccaccaaa   2100
gtgttggtgg catccaccca agggtcttct cccccaaccc cagccgtgca ggccacctcc   2160
tccggggcca tcacccttcc tcccaagcct gcgcccaccg gcacatcctg cgaaccaaag   2220
atcgtcatca acacggtccc ccagctccac tcggagaaaa ccatgtatct taagtccagc   2280
gacaaccgcc tcctcatgtc cctcttcctc ttcttctttg ttctcttcct ctgcctcttt   2340
ttctacaact gctataaggg atacctgccc agacagtgct tgaaattccg ctcggcccta   2400
```

```
ctaattggga agaagaagcc caagtcagat ttctgtgacc gtgagcagag cctgaaggag   2460

acgttagtag agccagggag cttctcccag cagaatgggg agcaccccaa gccagccctg   2520

gacaccggct atgagaccga gcaagacacc atcaccagca aagtccccac ggatagggag   2580

gactcacaga ggatcgacga cctttctgcc agggacaagc cctttgacgt caagtgtgag   2640

ctgaagttcg ctgactcaga cgcagatgga gactgaggcc ggctgtgcat ccccgctggt   2700

gcctcggctg cgacgtgtcc aggcgtggag agttttgtgt ttctcctgtt cagtatccga   2760

gtctcgtgca gtgctgcgta ggttagcccg catcgtgcag acaacctcag tcctcttgtc   2820

tattttctct tgggttgagc ctgtgacttg gtttctcttt gtccttttgg aaaaatgaca   2880

agcattgcat cccagtcttg tgttccgaag tcagtcggag tacttgaaga aggcccacgg   2940

gcggcacgga gttcctgagc cctttctgta gtgggggaaa ggtggctgga cctctgttgg   3000

ctgagaagag catcccttca gcttcccctc cccgtagcag ccactaaaag attatttaat   3060

tccagattgg aaatgacatt ttagtttatc agattggtaa cttatcgcct gttgtccaga   3120

ttggcacgaa ccttttcttc cacttaatta ttttttagg attttgcttt gattgtgttt   3180

atgtcatggg tcattttttt ttagttacag aagcagttgt gttaatattt agaagaagat   3240

gtatatcttc cagattttgt tatatatttg gcataaaata cggcttacgt tgcttaagat   3300

tctcagggat aaacttcctt ttgctaaatg cattctttct gcttttagaa atgtagacat   3360

aaacactccc cggagcccac tcaccttttt tctttttctt tttttttttt taactttatt   3420

ccttgaggga agcattgttt ttggagagat tttctttctg tacttcgttt tacttttctt   3480

ttttttaac ttttactctc tcgaagaaga ggaccttccc acatccacga ggtgggtttt   3540

gagcaaggga aggtagcctg gatgagctga gtggagccag gctggcccag agctgagatg   3600

ggagtgcggt acaatctgga gcccacagct gtcggtcaga acctcctgtg agacagatgg   3660

aaccttcaca agggcgcctt tggttctctg aacatctcct ttctcttctt gcttcaattg   3720

cttacccact gcctgcccag actttctatc cagcctcact gagctgccca ctactggaag   3780

ggaactgggc ctcggtggcc ggggccgcga gctgtgacca cagcaccctc aagcatacgg   3840

cgctgttcct gccactgtcc tgaagatgtg aatgggtggt acgatttcaa cactggttaa   3900

tttcacactc catctccccg ctttgtaaat acccatcggg aagagacttt ttttccatgg   3960

tgaagagcaa taaactctgg atgtttgtgc gcgtgtgtgg acagtcttat cttccagcat   4020

gataggattt gaccattttg gtgtaaacat ttgtgtttta taagatttac cttgttttta   4080

tttttctact ttgaattgta tacatttgga aagtacccaa ataaatgaga agcttctatc   4140

cttaaaaaaa aaaaaaa                                                  4157
```

<210> SEQ ID NO 3
<211> LENGTH: 22
<212> TYPE: DNA
<213> ORGANISM: artificial sequence
<220> FEATURE:
<223> OTHER INFORMATION: shRNA

<400> SEQUENCE: 3

```
ggcctgagga ccttgcagaa ga                                               22
```

<210> SEQ ID NO 4
<211> LENGTH: 22
<212> TYPE: DNA
<213> ORGANISM: Artificial sequence
<220> FEATURE:

```
<223> OTHER INFORMATION: portion of Semaphorin 4D sequence

<400> SEQUENCE: 4

ggcctgagga ccttgcagaa ga                                              22


<210> SEQ ID NO 5
<211> LENGTH: 4642
<212> TYPE: DNA
<213> ORGANISM: Homo sapiens

<400> SEQUENCE: 5

gctgtaacac tcaccgtgaa ggtctgcagc ttcactcccg agccagcgag accacgaacc     60

caccagaagg aagaaactct gaacacatct gaacatcaga agggacagac tccagacgcg    120

ccaccactct gctaacacca gatagtggaa agaaaccatg tgctgaaatg tttgacgaca    180

ctgatggttt gactctgcta actggaatgg cttattgtgc aagaaagtac acctggtcgg    240

gtcctggggc tcatctctag caccagcaaa gatttctgaa gacgtctttc tagaaatgac    300

tggaaagttt caagaggcat aagatacagc atttcttctg aggccctgaa gaagtatcaa    360

gtgggctttg acattgcggt ggtgagagcg acccctcctc acctggagaa ctgggaaatg    420

tggattctca gggaccgcgc tgttcacgag ctccaggctg tgctgctggc cctggtcctg    480

gggcgctgag ccgcatctgc aatagcacac ttgcccggcc acctgctgcc gtgagccttt    540

gctgctgaag cccctggggt cgcctctacc tgatgaggat gtgcaccccc attagggggc    600

tgctcatggc ccttgcagtg atgtttggga cagcgatggc atttgcaccc ataccccgga    660

tcacctggga gcacagagag gtgcacctgg tgcagtttca tgagccagac atctacaact    720

actcagcctt gctgctgagc gaggacaagg acaccttgta cataggtgcc cgggaggcgg    780

tcttcgctgt gaacgcactc aacatctccg agaagcagca tgaggtgtat tggaaggtct    840

cagaagacaa aaaagcaaaa tgtgcagaaa aggggaaatc aaaacagaca gagtgcctca    900

actacatccg ggtgctgcag ccactcagcg ccacttccct ttacgtgtgt gggaccaacg    960

cattccagcc ggcctgtgac cacctgaact taacatcctt taagtttctg ggaaaaaatg   1020

aagatggcaa aggaagatgt ccctttgacc cagcacacag ctacacatcc gtcatggttg   1080

atggagaact ttattcgggg acgtcgtata atttttttggg aagtgaaccc atcatctccc   1140

gaaattcttc ccacagtcct ctgaggacag aatatgcaat cccttggctg aacgagccta   1200

gtttcgtgtt tgctgacgtg atccgaaaaa gcccagacag ccccgacggc gaggatgaca   1260

gggtctactt cttcttcacg gaggtgtctg tggagtatga gtttgtgttc agggtgctga   1320

tcccacggat agcaagagtg tgcaaggggg accagggcgg cctgaggacc ttgcagaaga   1380

aatggacctc cttcctgaaa gcccgactca tctgctcccg gccagacagc ggcttggtct   1440

tcaatgtgct gcgggatgtc ttcgtgctca ggtccccggg cctgaaggtg cctgtgttct   1500

atgcactctt caccccacag ctgaacaacg tggggctgtc ggcagtgtgc gcctacaacc   1560

tgtccacagc cgaggaggtc ttctcccacg ggaagtacat gcagagcacc acagtggagc   1620

agtcccacac caagtgggtg cgctataatg gcccggtacc caagccgcgg cctggagcgt   1680

gcatcgacag cgaggcacgg gccgccaact acaccagctc cttgaatttg ccagacaaga   1740

cgctgcagtt cgttaaagac caccctttga tggatgactc ggtaacccca atagacaaca   1800

ggcccaggtt aatcaagaaa gatgtgaact acacccagat cgtggtggac cggacccagg   1860

ccctggatgg gactgtctat gatgtcatgt ttgtcagcac agaccgggga gctctgcaca   1920

aagccatcag cctcgagcac gctgttcaca tcatcgagga gacccagctc ttccaggact   1980
```

```
ttgagccagt ccagaccctg ctgctgtctt caaagaaggg caacaggttt gtctatgctg   2040
gctctaactc gggcgtggtc caggccccgc tggccttctg tgggaagcac ggcacctgcg   2100
aggactgtgt gctggcgcgg gacccctact gcgcctggag cccgcccaca gcgacctgcg   2160
tggctctgca ccagaccgag agccccagca ggggtttgat tcaggagatg agcggcgatg   2220
cttctgtgtg cccggataaa agtaaaggaa gttaccggca gcatttttc aagcacggtg    2280
gcacagcgga actgaaatgc tcccaaaaat ccaacctggc ccgggtcttt tggaagttcc   2340
agaatggcgt gttgaaggcc gagagcccca agtacggtct tatgggcaga aaaaacttgc   2400
tcatcttcaa cttgtcagaa ggagacagtg ggtgtacca gtgcctgtca gaggagaggg    2460
ttaagaacaa aacggtcttc caagtggtcg ccaagcacgt cctggaagtg aaggtggttc   2520
caaagcccgt agtggccccc accttgtcag ttgttcagac agaaggtagt aggattgcca   2580
ccaaagtgtt ggtggcatcc acccaagggt cttctccccc aaccccagcc gtgcaggcca   2640
cctcctccgg ggccatcacc cttcctccca agcctgcgcc caccggcaca tcctgcgaac   2700
caaagatcgt catcaacacg gtcccccagc tccactcgga gaaaaccatg tatcttaagt   2760
ccagcgacaa ccgcctcctc atgtccctct tcctcttctt ctttgttctc ttcctctgcc   2820
tctttttcta caactgctat aagggatacc tgcccagaca gtgcttgaaa ttccgctcgg   2880
ccctactaat tgggaagaag aagcccaagt cagatttctg tgaccgtgag cagagcctga   2940
aggagacgtt agtagagcca gggagcttct cccagcagaa tggggagcac cccaagccag   3000
ccctggacac cggctatgag accgagcaag acaccatcac cagcaaagtc cccacggata   3060
gggaggactc acagaggatc gacgaccttt ctgccaggga caagcccttt gacgtcaagt   3120
gtgagctgaa gttcgctgac tcagacgcag atggagactg aggccggctg tgcatccccg   3180
ctggtgcctc ggctgcgacg tgtccaggcg tggagagttt tgtgtttctc ctgttcagta   3240
tccgagtctc gtgcagtgct gcgtaggtta gcccgcatcg tgcagacaac ctcagtcctc   3300
ttgtctattt tctcttgggt tgagcctgtg acttggtttc tctttgtcct tttggaaaaa   3360
tgacaagcat tgcatcccag tcttgtgttc cgaagtcagt cggagtactt gaagaaggcc   3420
cacgggcggc acggagttcc tgagcccttt ctgtagtggg ggaaaggtgg ctggacctct   3480
gttggctgag aagagcatcc cttcagcttc ccctccccgt agcagccact aaaagattat   3540
ttaattccag attggaaatg acattttagt ttatcagatt ggtaacttat cgcctgttgt   3600
ccagattggc acgaaccttt tcttccactt aattattttt ttaggatttt gctttgattg   3660
tgtttatgtc atgggtcatt ttttttagt tacagaagca gttgtgttaa tatttagaag    3720
aagatgtata tcttccagat tttgttatat atttggcata aaatacggct tacgttgctt   3780
aagattctca gggataaact tccttttgct aaatgcattc tttctgcttt tagaaatgta   3840
gacataaaca ctccccggag cccactcacc tttttctttt ttctttttt tttttaact     3900
ttattccttg agggaagcat tgtttttgga gagattttct ttctgtactt cgttttactt   3960
ttcttttttt ttaactttta ctctctcgaa gaagaggacc ttcccacatc cacgaggtgg   4020
gttttgagca agggaaggta gcctggatga gctgagtgga gccaggctgg cccagagctg   4080
agatgggagt gcggtacaat ctggagccca cagctgtcgg tcagaacctc ctgtgagaca   4140
gatggaacct tcacaagggc gcctttggtt ctctgaacat ctcctttctc ttcttgcttc   4200
aattgcttac ccactgcctg cccagacttt ctatccagcc tcactgagct gcccactact   4260
ggaagggaac tgggcctcgg tggccggggc cgcgagctgt gaccacagca ccctcaagca   4320
```

```
tacggcgctg ttcctgccac tgtcctgaag atgtgaatgg gtggtacgat ttcaacactg   4380

gttaatttca cactccatct ccccgctttg taaataccca tcgggaagag acttttttttc   4440

catggtgaag agcaataaac tctggatgtt tgtgcgcgtg tgtggacagt cttatcttcc   4500

agcatgatag gatttgacca ttttggtgta aacatttgtg ttttataaga tttaccttgt   4560

ttttattttt ctactttgaa ttgtatacat ttggaaagta cccaaataaa tgagaagctt   4620

ctatccttaa aaaaaaaaaa aa                                            4642


<210> SEQ ID NO 6
<211> LENGTH: 4417
<212> TYPE: DNA
<213> ORGANISM: Homo sapiens

<400> SEQUENCE: 6

gctgtaacac tcaccgtgaa ggtctgcagc ttcactcccg agccagcgag accacgaacc     60

caccagaagg aagaaactct gaacacatct gaacatcaga agggacagac tccagacgcg    120

ccaccactct gctaacacca gatagtggaa agaaaccatg tgctgaaatg tttgacgaca    180

ctgatggttt gactctgcta actggaatgg cttattgtgc aagaaagtac acctggtcgg    240

gtcctggggc tcatctctag caccagcaaa gatttctgaa gacgtctttc tagaaatgac    300

tggaaagttt caagaggcat aagatacagc atttcttctg aggccctgaa gaagtatcaa    360

gtgggctttg acattgcggt ggtgagagcg accccctcctc acctggagaa ctgggaaatg    420

tggattctca gggaccgcgc tgttcacgag ctccaggctg tgctgctggc cctggtcctg    480

gggcgctgag ccgcatctgc aatagcacac ttgcccggcc acctgctgcc gtgagccttt    540

gctgctgaag cccctggggt cgcctctacc tgatgaggat gtgcaccccc attagggggc    600

tgctcatggc ccttgcagtg atgtttggga cagcgatggc atttgcaccc ataccccgga    660

tcacctggga gcacagagag gtgcacctgg tgcagtttca tgagccagac atctacaact    720

actcagcctt gctgctgagc gaggacaagg acaccttgta cataggtgcc cgggaggcgg    780

tcttcgctgt gaacgcactc aacatctccg agaagcagca tgaggtgtat tggaaggtct    840

cagaagacaa aaaagcaaaa tgtgcagaaa aggggaaatc aaaacagaca gagtgcctca    900

actacatccg ggtgctgcag ccactcagcg ccacttccct ttacgtgtgt gggaccaacg    960

cattccagcc ggcctgtgac cacctgaact taacatcctt taagtttctg ggaaaaaatg   1020

aagatggcaa aggaagatgt cccctttgacc cagcacacag ctacacatcc gtcatggttg   1080

atggagaact ttattcgggg acgtcgtata attttttggg aagtgaaccc atcatctccc   1140

gaaattcttc ccacagtcct ctgaggacag aatatgcaat cccttggctg aacgagccta   1200

gtttcgtgtt tgctgacgtg atccgaaaaa gcccagacag ccccgacggc gaggatgaca   1260

gggtctactt cttcttcacg gaggtgtctg tggagtatga gtttgtgttc agggtgctga   1320

tcccacggat agcaagagtg tgcaaggggg accagggcgg cctgaggacc ttgcagaaga   1380

aatggacctc cttcctgaaa gcccgactca tctgctcccg gccagacagc ggcttggtct   1440

tcaatgtgct gcgggatgtc ttcgtgctca ggtccccggg cctgaaggtg cctgtgttct   1500

atgcactctt caccccacag ctgaacaacg tggggctgtc ggcagtgtgc gcctacaacc   1560

tgtccacagc cgaggaggtc ttctcccacg ggaagtacat gcagagcacc acagtggagc   1620

agtcccacac caagtgggtg cgctataatg gcccggtacc caagccgcgg cctggagcgt   1680

gcatcgacag cgaggcacgg gccgccaact acaccagctc cttgaatttg ccagacaaga   1740

cgctgcagtt cgttaaagac cacccctttga tggatgactc ggtaacccca atagacaaca   1800
```

```
ggcccaggtt aatcaagaaa gatgtgaact acacccagat cgtggtggac cggacccagg   1860
ccctggatgg gactgtctat gatgtcatgt ttgtcagcac agaccgggga gctctgcaca   1920
aagccatcag cctcgagcac gctgttcaca tcatcgagga gacccagctc ttccaggact   1980
ttgagccagt ccagaccctg ctgctgtctt caaagaaggg caacaggttt gtctatgctg   2040
gctctaactc gggcgtggtc caggccccgc tggccttctg tgggaagcac ggcacctgcg   2100
aggactgtgt gctggcgcgg gacccctact gcgcctggag cccgcccaca gcgacctgcg   2160
tggctctgca ccagaccgag agccccagca ggggtttgat tcaggagatg agcggcgatg   2220
cttctgtgtg cccggcctcg tctcctaagc cctccctcc tcctggctcc tcttccctgt    2280
cctgtctggg ccatgtgggg gacaggaggc tttcctctcc ctggaccccc tggccagcct   2340
cgggtgcggg gcccgacagc agctcgaggg tctccttgct gccgcccttc ctgagtgacc   2400
aggcacagca cgtgcacgcc ctggggaact tctacctctt ctgccaggcc acaggtcctg   2460
cagacattcg ctttgtctgg gagaagaatg ggcgagctct ggagacctgt gtccctgtgc   2520
agacccatgc actgcccgat ggcagggccc atgcactcag ctggctgcag gacgccatca   2580
gggaaagcgc tgagtatcgc tgctctgtcc tctcctcagc agggaacaag acttcgaagg   2640
tgcaggttgc tgtgatgaga cctgaagtga cccaccagga gaggtggacc agagagctct   2700
ctgcctggag ggctgtggct ggggagcacg accggatgat gcagagctgg aggaaggcgt   2760
gggaaagctg tagcaaggac accctgtagc caccaggaag gagtccctga caccgacctc   2820
aaccccaaca agaccctgct gccactgacc acagccaccc ccggagaagg cctggtcccc   2880
cacaactgtg aactgtcttg cccaagcctg ctctgaacac agccattggg ccaccacctg   2940
atgggcagag gcgggacagt ggagaagcct ggaacccaag tgggcctgtg acaggaacta   3000
agacttaaaa aattaggtgc ttacctggga cagtaagttc tgtctggcac aagcaggtaa   3060
ccaggatggc taacaggctt tgatagctgc tcgtgaacta aaacagcagg gtgtgtgcag   3120
gttcctcctc tacggtcagg cagcaggctc tgaaggctga tcctacaccg tcccagtgac   3180
tccccttgac agagtgcccc cacccctaa tagccaacag ggttagcatg gccagcacag    3240
atcgctgctt ttattgatgc aaatcaagcc tgctgcttct cctccctgca gacttagcca   3300
aggaactcca agatgcatga ctgggacaag aaaaggtgag actccacatg gaaatgcctt   3360
gccctaaacc ttgaatgact gtgagatgcg atctgggagt gcatctgtca agtctttgtg   3420
ttttcttcac taacctcaga atactgggct ctattttatc aagcgctgca gtttatgcct   3480
ctgtcccgtc aatgctcagc ttctgcaaca ggacaccaaa cttgatgcag aaagccaaat   3540
aggtcaatta tgcaaatctc ctggtgccat attaaatttc ttgacgatgg aatgagtctc   3600
atgagtgttt tgttctacct gctttcaagt ctctaattat taaagctgta tctctgaaga   3660
ctgtgtcact gtgtgtgtga acttgtccta aagctactca gcctttaatc ttacacacac   3720
gtctcttctt gtctgttgaa tgacagtttt catgtctatc ataaaaccaa agcctctgtt   3780
aaaagtcaag ccgcacccct ctggtgatcc tagcaaatac tgagtgtctt cccagcagtg   3840
tgacaatgac ctgttttgca tcccctcttt ctggagctgg acaaattctc taccagcctt   3900
tgtgtgggat cagcatacat cgcctgctaa ttccttcagg atccatcaca acaggtgtcc   3960
tgaagatgct ggagacaccc tggttgtctc cacacgttcc ccctccgcac cccaagtcga   4020
gaggcccagc tgcctgtgag gtgtgtgctt gcccatccag ccaaggatgc cagtcttgct   4080
cacggaacca tcacatactc ataacctgaa gttttcctgt aaaatatcca tcagctcact   4140
```

-continued

```
gtggttcttg ctttgggtgt ggcttcaacc actacaaact gatgagtgaa atgctatggg   4200

ctttaggctt atattcttgg tgctgttttc tgtctcttct cctgaagtct ggatttcaag   4260

cactttcaca cttaacaaaa taattacata cttgaagttt tcgtaatgtg gagtgttcta   4320

ctgggaaatg gagttatgag gatgaatttc tgagtctttc tttgctctgc tggaaaaaat   4380

aaaaatagag ttgtacattg aaaaaaaaaa aaaaaaa                            4417


<210> SEQ ID NO 7
<211> LENGTH: 21
<212> TYPE: DNA
<213> ORGANISM: Artificial sequence
<220> FEATURE:
<223> OTHER INFORMATION: portion of Semaphorin 4D

<400> SEQUENCE: 7

caagacgctg cagttcgtta a                                               21
```